(12) United States Patent
Brekken et al.

(10) Patent No.: US 10,370,360 B2
(45) Date of Patent: Aug. 6, 2019

(54) SMALL-MOLECULE INHIBITORS TARGETING DISCOIDIN DOMAIN RECEPTOR 1 AND USES THEREOF

(71) Applicants: The Board of Regents of the University of Texas System, Austin, TX (US); Guangzhou Institutes of Biomedicine and Health, Chinese Academy of Sciences, Guangzhou (CN)

(72) Inventors: Rolf A. Brekken, Dallas, TX (US); Ke Ding, Guangzhou (CN); Xiaomei Ren, Guangzhou (CN); Zhengchao Tu, Guangzhou (CN); Zhen Wang, Guangzhou (CN); Kristina Y. Aguilera, Dallas, TX (US)

(73) Assignees: The Board of Regents of the University of Texas System, Austin, TX (US); Guangzhou Institutes of Biomedicine and Health, Chinese Academy of Sciences, Guangzhou (CN)

( * ) Notice: Subject to any disclaimer, the term of this patent is extended or adjusted under 35 U.S.C. 154(b) by 30 days.

(21) Appl. No.: 15/521,107

(22) PCT Filed: Oct. 21, 2015

(86) PCT No.: PCT/US2015/056611
§ 371 (c)(1),
(2) Date: Apr. 21, 2017

(87) PCT Pub. No.: WO2016/064970
PCT Pub. Date: Apr. 28, 2016

(65) Prior Publication Data
US 2018/0022730 A1 Jan. 25, 2018

Related U.S. Application Data

(60) Provisional application No. 62/204,176, filed on Aug. 12, 2015, provisional application No. 62/067,070, filed on Oct. 22, 2014.

(51) Int. Cl.
| | | |
|---|---|---|
| A61K 31/337 | (2006.01) |
| A61K 31/4725 | (2006.01) |
| A61K 31/7068 | (2006.01) |
| A61K 45/06 | (2006.01) |
| C07D 401/04 | (2006.01) |
| C07D 401/14 | (2006.01) |

(52) U.S. Cl.
CPC .......... *C07D 401/14* (2013.01); *A61K 31/337* (2013.01); *A61K 31/4725* (2013.01); *A61K 31/7068* (2013.01); *A61K 45/06* (2013.01); *C07D 401/04* (2013.01); *A61K 2300/00* (2013.01)

(58) Field of Classification Search
CPC combination set(s) only.
See application file for complete search history.

(56) References Cited

U.S. PATENT DOCUMENTS

| | | | |
|---|---|---|---|
| 6,121,283 A | 9/2000 | Chang et al. | |
| 7,268,142 B2 * | 9/2007 | Allen | C07D 401/04 514/266.21 |
| 2007/0054916 A1 | 3/2007 | Patel et al. | |
| 2013/0059838 A1 | 3/2013 | Gao et al. | |

FOREIGN PATENT DOCUMENTS

| | | |
|---|---|---|
| WO | WO 1998/043968 | 10/1998 |
| WO | WO 2005/082883 | 9/2005 |
| WO | WO 2010/093419 | 8/2010 |

OTHER PUBLICATIONS

Beeby et al. "Synthesis and properties of 2,7-disubstituted 1,2,3,4-tetrahydroisoquinolines" J. Chem. Soc. 1949, 1799-1803. (Year: 1949).*
Li et al. "Small Molecule Discoidin Domain Receptor Kinase Inhibitors and Potential Medical Applications" J. Med. Chem. 2015, 58, 3287-3301. (Year: 2015).*
Aguilera et al., "Abstract 182: SPARC as a regulator of collagen signaling in pancreatic cancer," *Proceedings: American Association for Cancer Research Annual Meeting*, San Diego, CA, Apr. 2014.
Ambrogio et al., "Combined inhibition of DDR1 and Notch signaling is a therapeutic strategy for KRAS-driven lung adenocarcinoma," *Nat Med.*, 22(3):270-277, 2016.
Das et al., "Discoidin domain receptor 1 receptor tyrosine kinase induces cyclooxygenase-2 and promotes chemoresistance through nuclear factor-kappaB pathway activation," Cancer Res, 66(16):8123-8130, 2006.
Extended European Search Report issued in European Application No. 15852998.2, dated Mar. 2, 2018.
Gao et al., "Discovery and optimization of 3-(2-(Pyrazolo[1,5-a]pyrimidin-6-yl)ethynyl)benzamides as novel selective and orally bioavailable discoidin domain receptor 1 (DDR1) inhibitors," J Med Chem, 56(8):3281-3295, 2013.

(Continued)

*Primary Examiner* — Amanda L Aguirre
(74) *Attorney, Agent, or Firm* — Parker Highlander PLLC

(57) ABSTRACT

Compounds of formula (I), their pharmaceutically acceptable salts and stereoisomers thereof, as well as application in effectively inhibiting the enzymatic activity of discoidin domain receptor 1 and can be used as new therapeutic agents for preventing and treating e.g. inflammation, liver fibrosis, kidney fibrosis, lung fibrosis, skin scar, atherosclerosis, and cancer. The compound of formula I is: wherein the variables are as defined herein.

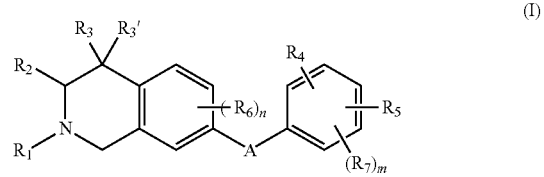

(I)

19 Claims, 38 Drawing Sheets
Specification includes a Sequence Listing.

(56) References Cited

OTHER PUBLICATIONS

Gao et al., "Integrative analysis of complex cancer genomics and clinical profiles using the cBioPortal," Sci Signal, 6(269):pl1, 2013.
Kim et al., "DDR1 receptor tyrosine kinase promotes prosurvival pathway through Notch1 activation," J Biol Chem, 286(20):17672-17681, 2011.
Li et al., "Small molecule discoidin domain receptor kinase inhibitors and potential medical applications—Miniperspective," *J. Med. Chem*, 58(8):3287-3301, 2015.
Miao et al., "Discoidin domain receptor 1 is associated with poor prognosis of non-small cell lung cancer and promotes cell invasion via epithelial-to-mesenchymal transition," Med Oncol, 30(3):626, 2013.
PCT International Preliminary Report on Patentability issued in International Application No. PCT/US2015/056611, dated May 4, 2017.
PCT International Search Report and Written Opinion issued in International Application No. PCT/US2015/056611, dated Feb. 23, 2016.
Shintani et al., "Collagen I-mediated up-regulation of N-cadherin requires cooperative signals from integrins and discoidin domain receptor 1," J Cell Biol, 180(6):1277-1289, 2008.
Valencia et al., "Inhibition of collagen receptor discoidin domain receptor-1 (DDR1) reduces cell survival, homing, and colonization in lung cancer bone metastasis," Clin Cancer Res, 18(4):969-980, 2012.

* cited by examiner

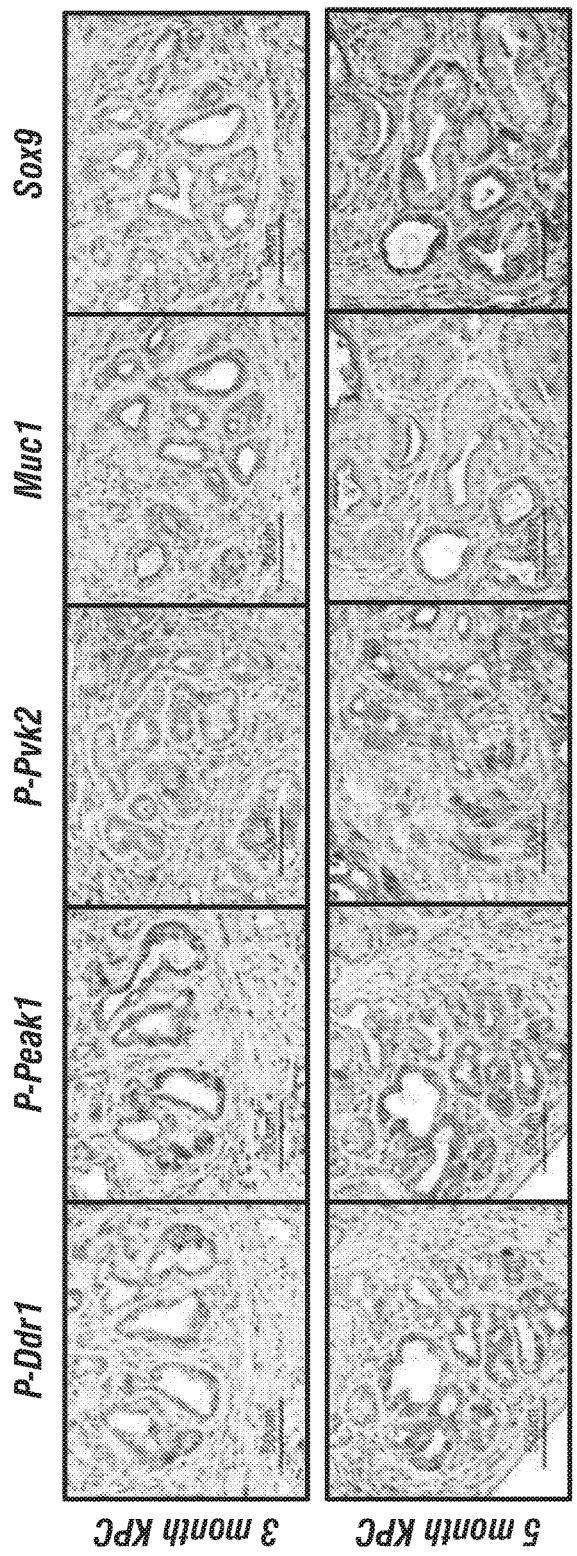
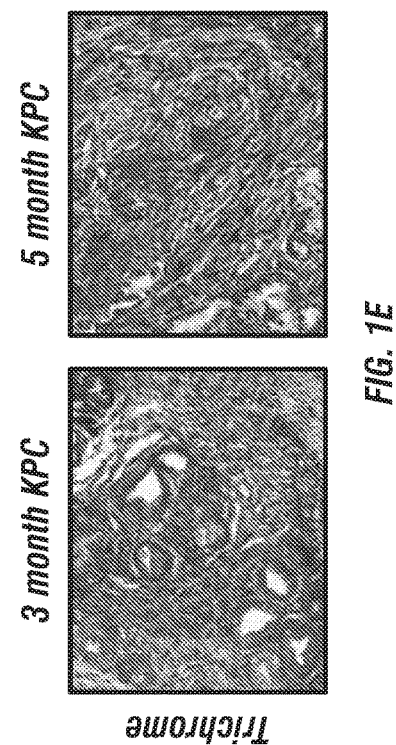
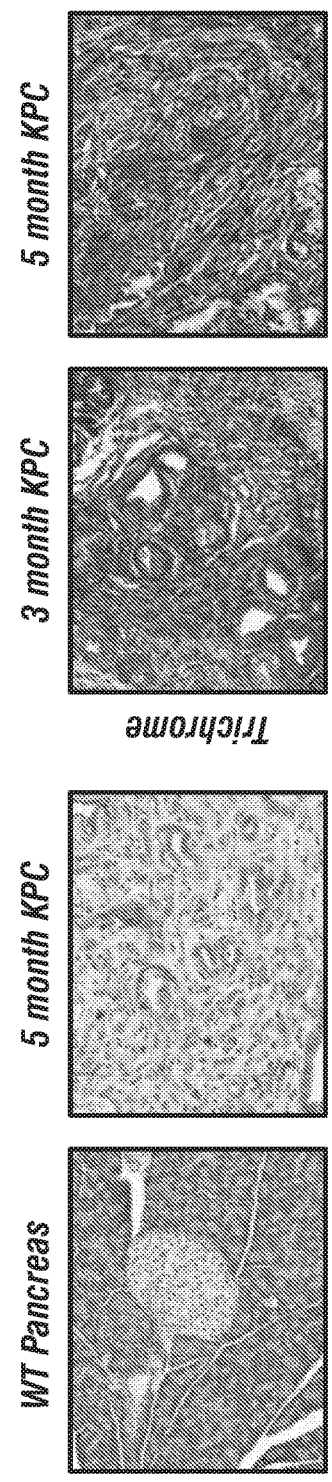
FIG. 1C
FIG. 1D
FIG. 1E

| Score | Phospho-DDR1 | | | | Phospho-PEAK1 | | | |
|---|---|---|---|---|---|---|---|---|
| | 0-1 | 2 | 3 | 4 | 0-1 | 2 | 3 | 4 |
| Human (%) | 0 | 31.25 | 37.5 | 31.25 | 3.61 | 43.7 | 38.25 | 14.45 |
| PATX (%) | 6.25 | 53.125 | 34.38 | 6.25 | 13.4 | 36.5 | 36.5 | 13.65 |

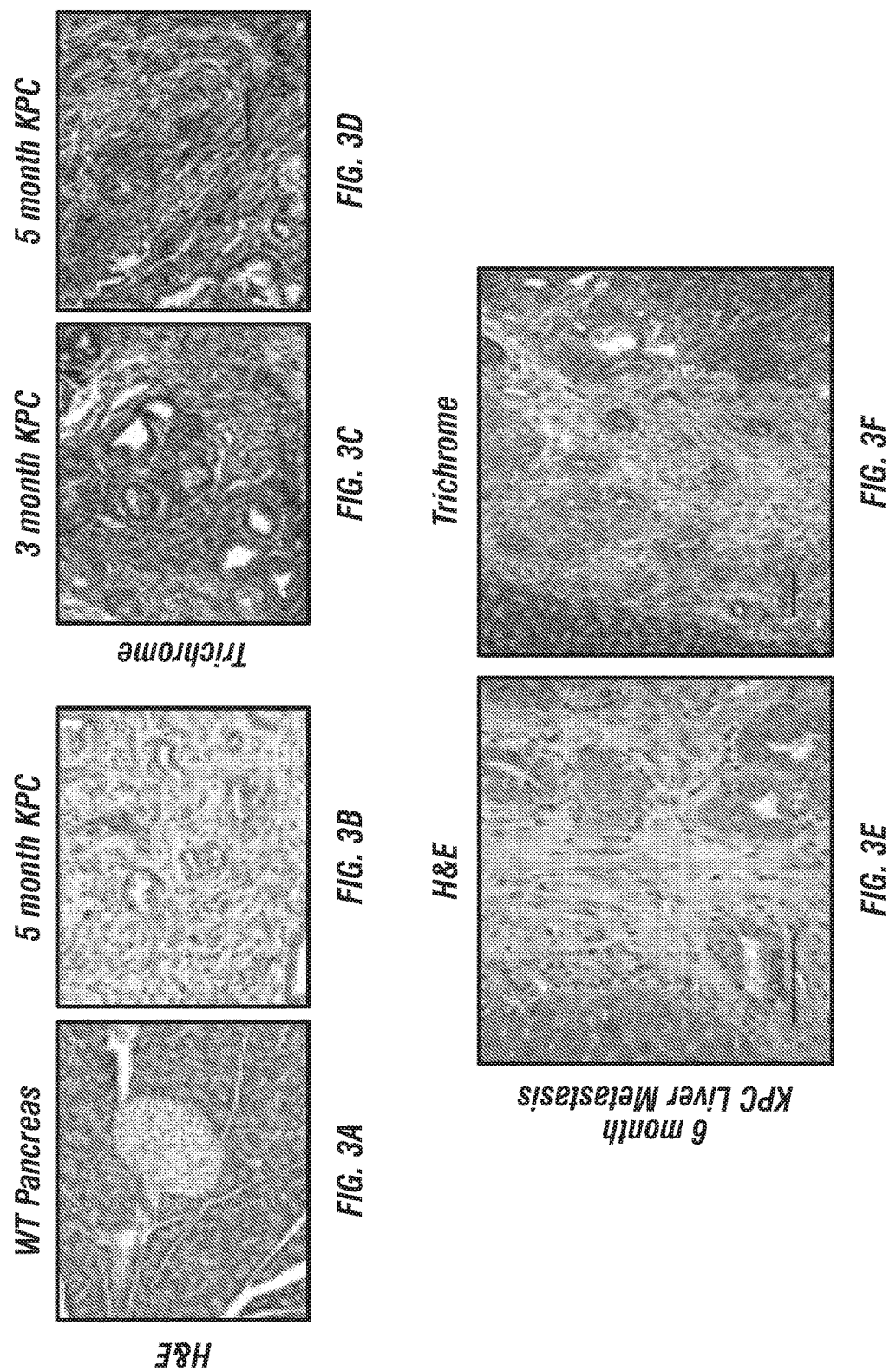

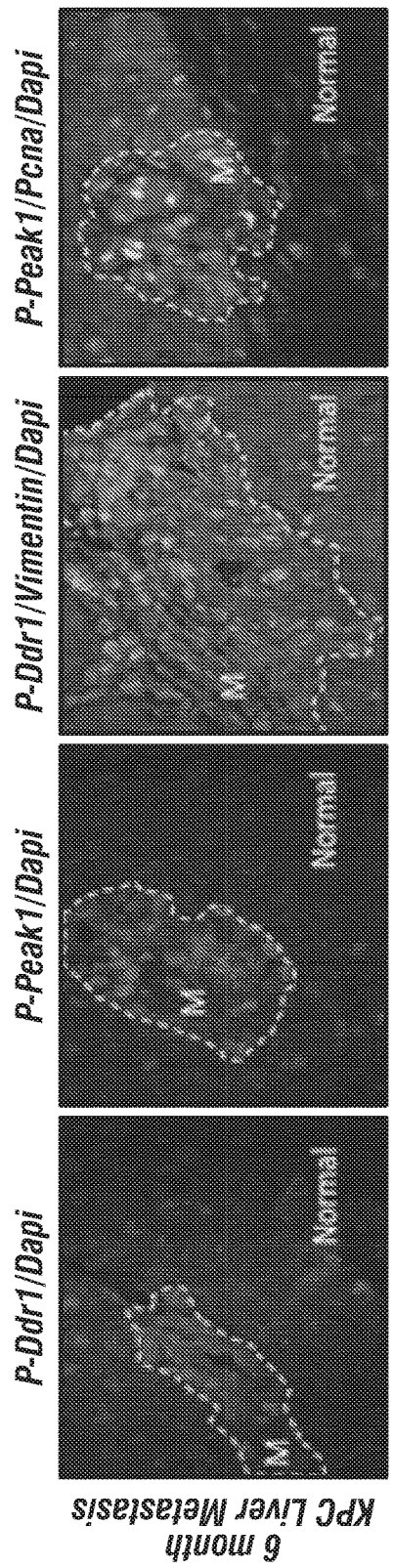
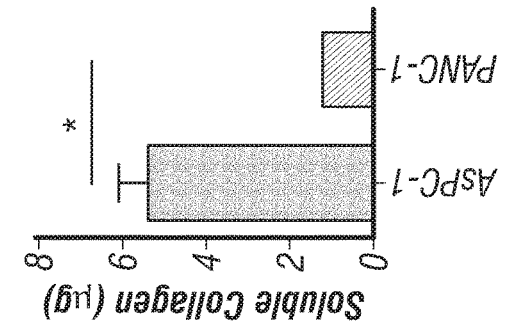
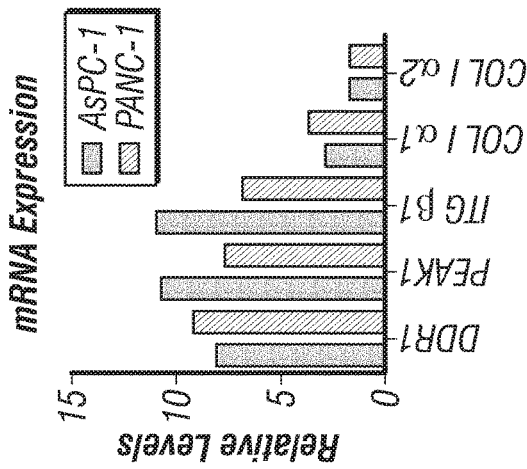
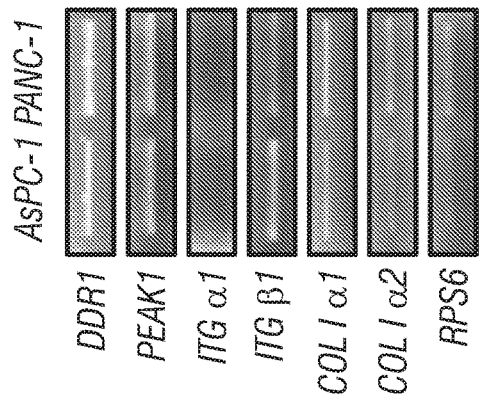
FIG. 3G, FIG. 3H, FIG. 3I, FIG. 3J, FIG. 4A, FIG. 4B

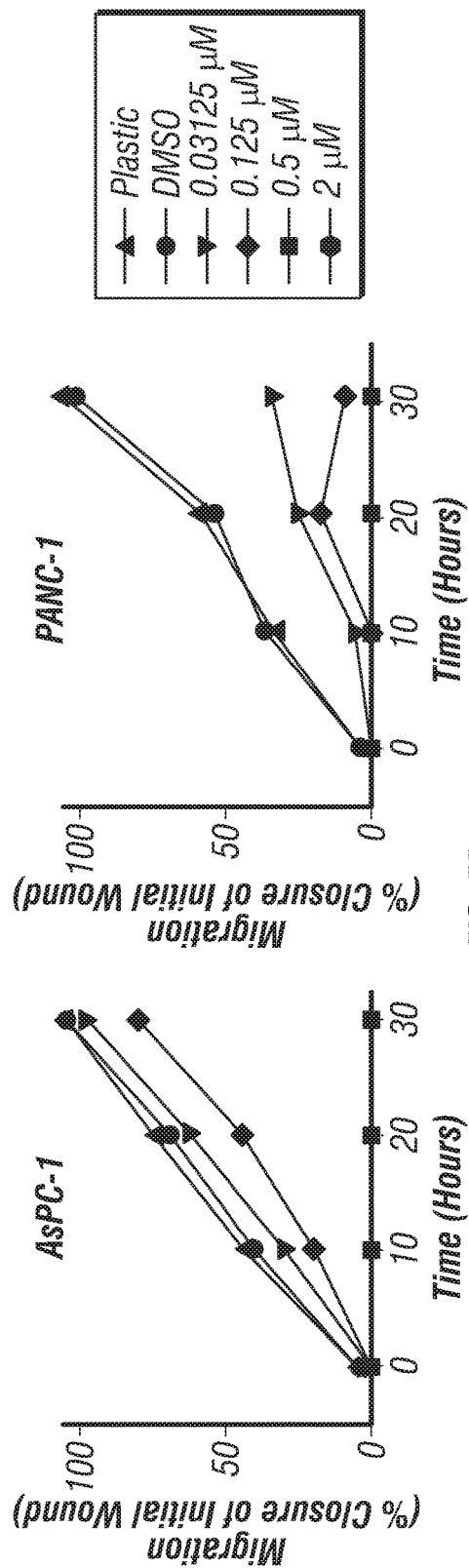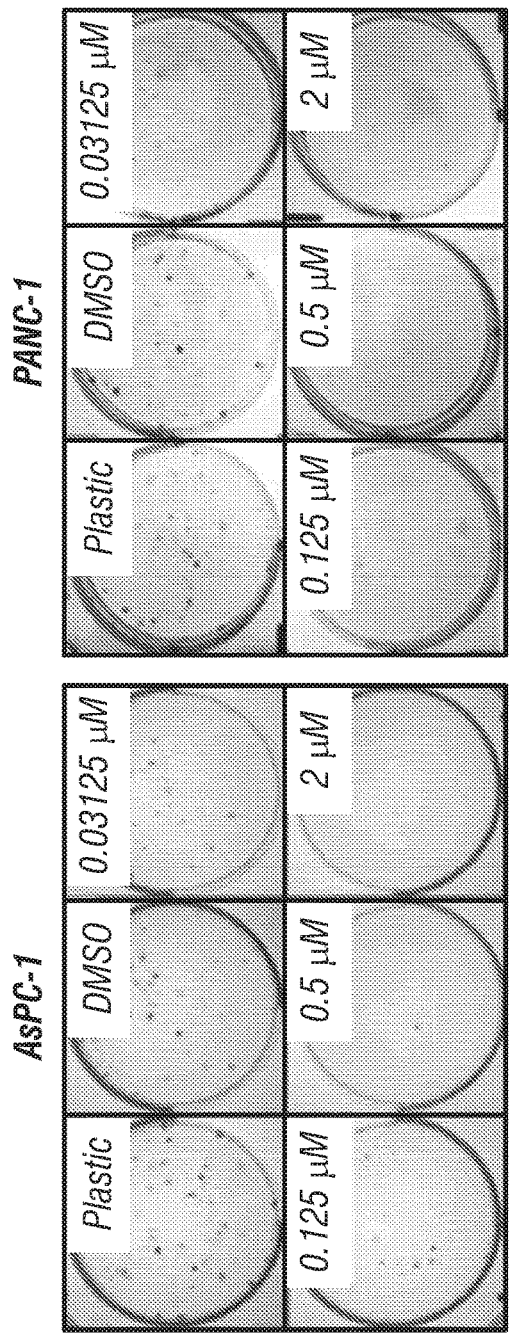
FIG. 5B
FIG. 5C

|  | AsPC-1 | PANC-1 |
|---|---|---|
| 7rh (nM) Avg $IC_{50}$ | 490 (6) | 380 (4) |
| Gemcitabine (nM) Avg $IC_{50}$ | 2000 (3) | 2000 (4) |
| 250 nM 7rh + Gem Avg $IC_{50}$ | 1725 (3) | 16.4 (3) |
| 500 nM 7rh + Gem Avg $IC_{50}$ | 2.05 (2) | 0.035 (3) |

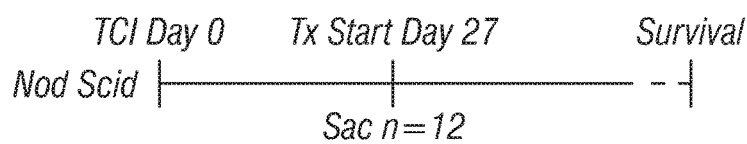
FIG. 11A
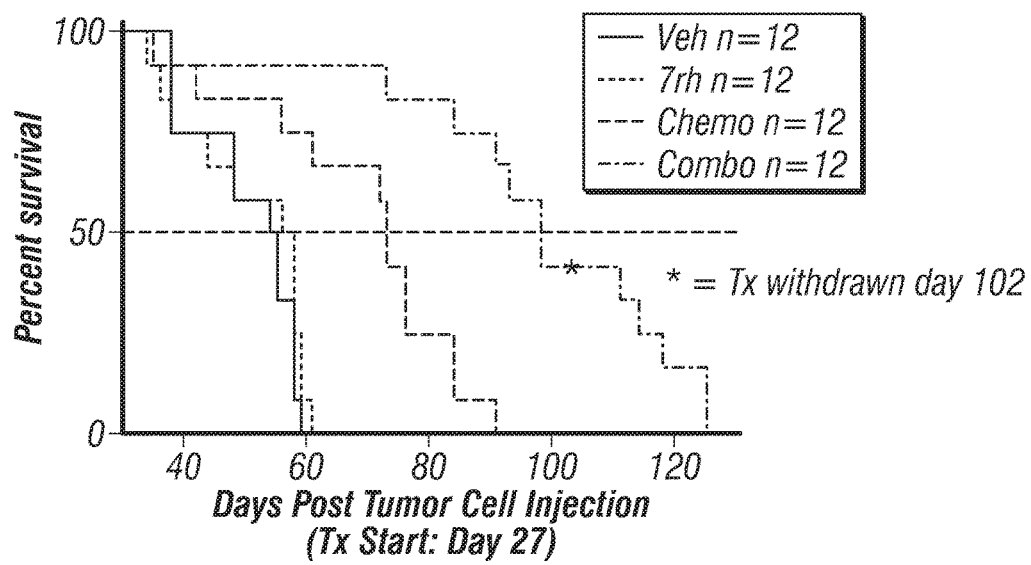
FIG. 11B
| Group | n | Median survival | p value vs vehicle | p value vs combo |
|---|---|---|---|---|
| 7rh | 12 | 57 | none | 0.0011 |
| Chemo | 12 | 73 | 0.0006 | <0.0001 |
| Combo | 12 | 98 | <0.0001 | |
FIG. 11C

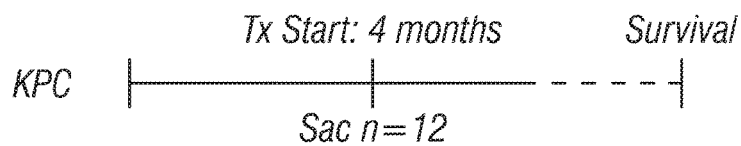
FIG. 13A
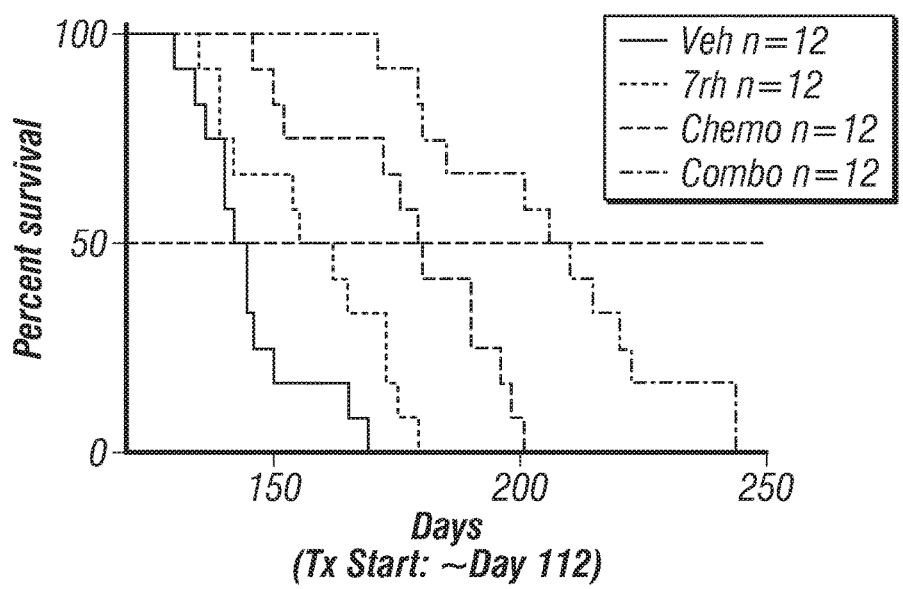
FIG. 13B
| Group | n | Median survival | p value vs vehicle | p value vs combo |
|---|---|---|---|---|
| 7rh | 12 | 159 | none | <0.0001 |
| Chemo | 12 | 180 | <0.0001 | 0.0012 |
| Combo | 12 | 208 | <0.0001 | |
FIG. 13C

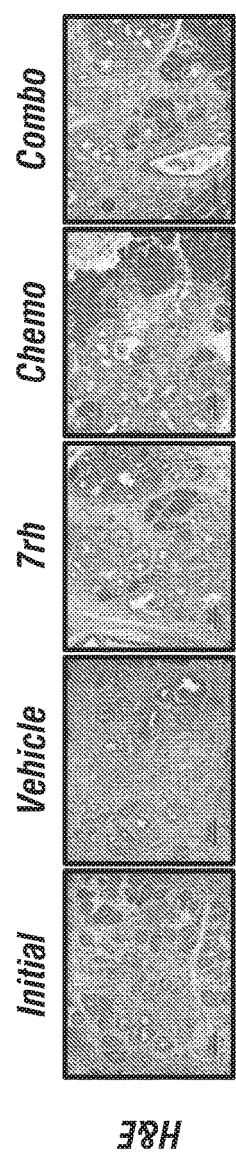
FIG. 13D
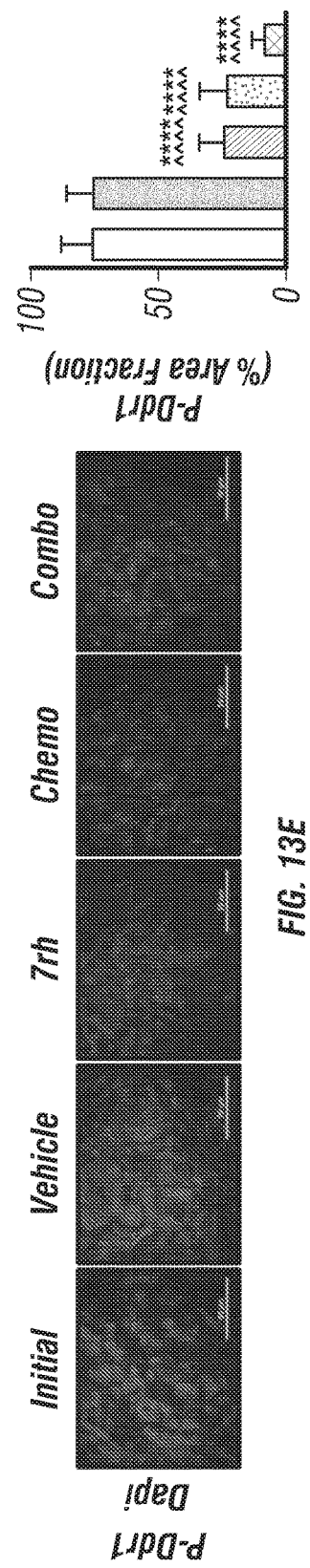
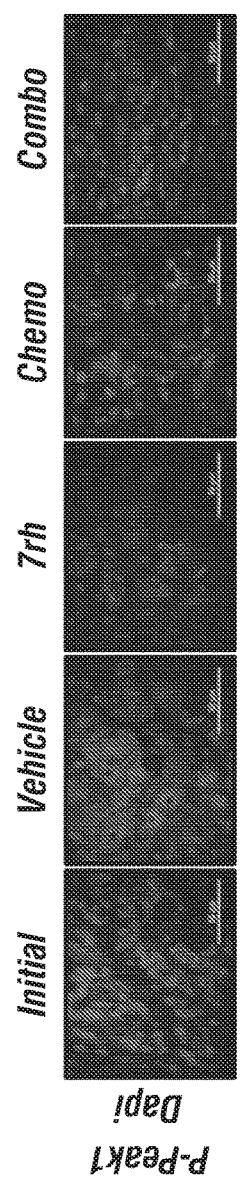
FIG. 13E
FIG. 13F

SEQUENCE LISTING

```
<160> NUMBER OF SEQ ID NOS: 22

<210> SEQ ID NO 1
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 1
gucuuguagc uagaacuucu cuaag                                              25

<210> SEQ ID NO 2
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 2
gucagaacau cgaucuugaa gagauuc                                            27

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
gcacuaggca gguaauaaua aaggt                                              25

<210> SEQ ID NO 4
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 4
```

```
gacgugaucc guccauuauu auuucca                                27
```

<210> SEQ ID NO 5
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 5

```
acacuaauau auggaccuag auuga                                  25
```

<210> SEQ ID NO 6
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 6

```
aaugugauua uauaccugga ucgaacu                                27
```

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7

```
cctctttgca ggtccttggt t                                      21
```

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8

```
agctccaagc tgctgaagtt g                                      21
```

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9

```
aagctgggag aaggccagtt                                        20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10

```
aggctggttg gcactgacat                                        20
```

<210> SEQ ID NO 11
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 11
gacgccatca aggtctactg                                                  20

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
acgggaatcc atcggtca                                                    18

<210> SEQ ID NO 13
<211> LENGTH: 19
<212> TYPE: DNA
<213> ORGANISM: Artificial Sequence
<220> FEATURE:
<223> OTHER INFORMATION: Synthetic primer

<400> SEQUENCE: 13
ggagggaacg gtccacgat                                                   19

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
gagtccgcgg tatccacaa                                                   19

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tgggtgctta ttggttctcc                                                  20

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
cctcctttct tgctgtgtct at                                               22

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
gaagctcaag ccagaggata tt                                               22
```

```
<210> SEQ ID NO 18
<211> LENGTH: 22
<212> TYPE: DNA
<213> ORGANISM: Artificial Sequence
<220> FEATURE:
<223> OTHER INFORMATION: Synthetic primer

<400> SEQUENCE: 18
ctggacaagg tgagcaatag aa                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
gttggagtag cctcccatta tc                                              22

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
gacgcttagt aggacccaaa g                                               21

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
gagcgttctc aacttggtta ttg                                             23

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
gtgctttggt cctaggtttc t                                               21
```

SMALL-MOLECULE INHIBITORS TARGETING DISCOIDIN DOMAIN RECEPTOR 1 AND USES THEREOF

PRIORITY CLAIM

This application is a national phase application under 35 U.S.C. § 371 of International Application No. PCT/US2015/056611, filed Oct. 21, 2015, which claims benefit of priority to U.S. Provisional Application Ser. No. 62/067,070, filed Oct. 22, 2014, and U.S. Provisional Application Ser. No. 62/204,176, filed Aug. 12, 2015, the entire contents of each of which are hereby incorporated by reference.

FEDERAL GRANT SUPPORT

This invention was made with government support under Grant Numbers R01 CA118240 and F31 CA168350 awarded by the National Institutes of Health. The government has certain rights in the invention.

BACKGROUND

A. Field

The present disclosure belongs to the field of medicinal chemistry. In some aspects, it relates to inhibitors of discoidin domain receptors and methods of use thereof.

B. Related Art

Discoidin domain receptors (DDRs), including DDR1 and DDR2, are members of transmembrane receptor tyrosine kinases (RTKs) discovered in the early 1990s. Unlike other RTKs, DDRs contain two discoidin domains in the extracellular region. DDRs are activated by a number of triple-helical collagens which are most abundant components of the extracellular matrix (ECM). DDR1 is widely expressed in epithelial cells in lung, kidney, colon, brain, whereas DDR2 is primarily expressed in mesenchymal cells including fibroblasts, myofibroblasts, smooth muscle, and skeletal in kidney, skin, lung, heart, and connective tissues. Studies have demonstrated that both DDR1 and DDR2 play crucial roles in fundamental cellular processes, such as proliferation, survival, differentiation, adhesion, and matrix remodeling. Deregulation of DDRs has been implicated in a number of human diseases, including fibrotic disorders, atherosclerosis, and cancer.

A number of other well-characterized kinase inhibitors, imatinib, nilotinib, dasatinib, bafetinib, ponatinib, sorafinib, pazopanib, foretinib, BIRB-796, and LCB 03-0110, are reported to be potent inhibitors of both DDR1 and DDR2. However, all these inhibitors also potently target many other kinases and cannot be utilized as good pharmacological probes of DDR1. Recently, DDR1 inhibitors, 7rh and DDR1-IN-1, have been disclosed which show increased selectivity for DDR1 and show potential promise as therapeutic agents. Given the potential therapeutic utility of DDR1 inhibitors, the development of additional inhibitors, including inhibitors with a unique pharmacore, is of therapeutic importance.

SUMMARY

In some aspects, the present disclosure provides compounds which may be used to inhibit discoidin domain receptor 1 (DDR1) and other discoidin domain receptors and/or used in the treatment of inflammatory disease and cancer.

In some aspects, the present disclosure provides compounds of the formula:

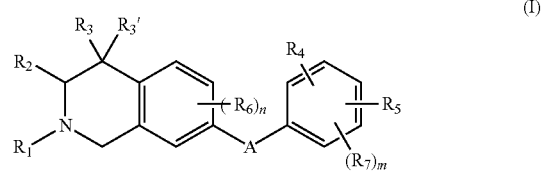

wherein:
  A is —NR$_8$C(O)— or —C(O)NR$_8$—; wherein:
    R$_8$ is hydrogen, alkyl$_{(C \leq 6)}$, or substituted alkyl$_{(C \leq 6)}$;
  R$_1$ is aryl$_{(C \leq 12)}$, heteroaryl$_{(C \leq 12)}$, or a substituted version of either of these groups;
  R$_2$, R$_3$, and R$_3$' are each independently hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$;
  R$_4$ is hydrogen, alkyl$_{(C \leq 12)}$, cycloalkyl$_{(C \leq 12)}$, aryl$_{(C \leq 12)}$, substituted alkyl$_{(C \leq 12)}$, substituted cycloalkyl$_{(C \leq 12)}$, or substituted aryl$_{(C \leq 12)}$;
  R$_5$ is hydrogen, heteroaryl$_{(C \leq 12)}$, —X—R$_9$, wherein:
    X is a covalent bond, alkanediyl$_{(C \leq 8)}$, or substituted alkanediyl$_{(C \leq 8)}$;
    R$_9$ is amino or heterocycloalkyl$_{(C \leq 12)}$, heteroaryl$_{(C \leq 12)}$, alkylamino$_{(C \leq 12)}$, dialkylamino$_{(C \leq 12)}$, or a substituted version of any of these groups; or a group of the formula:

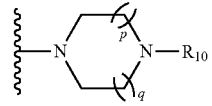

wherein:
    R$_{10}$ is hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and
    p and q are each 0, 1, or 2;
  R$_6$ and R$_7$ are each independently amino, cyano, halo, hydroxy, hydroxysulfonyl, nitro, sulfonamide; or alkyl$_{(C \leq 8)}$, acyl$_{(C \leq 8)}$, alkoxy$_{(C \leq 8)}$, amido$_{(C \leq 8)}$, acyloxy$_{(C \leq 8)}$, alkylamino$_{(C \leq 8)}$, or dialkylamino$_{(C \leq 8)}$; and
  m and n are each independently 0, 1, 2, or 3;
or a pharmaceutically acceptable salt thereof. In some embodiments, the compounds are further defined as:

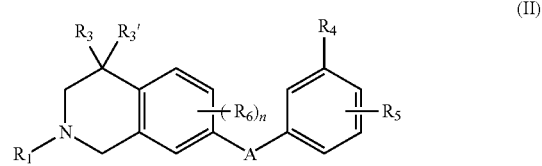

wherein: A, R$_1$, R$_3$, R$_3$', R$_4$, R$_5$, R$_6$, and n are as defined above; or a pharmaceutically acceptable salt thereof. In some embodiments, the compounds are further defined as:

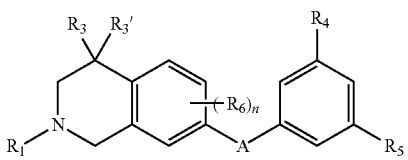

(III)

wherein: A, $R_1$, $R_3$, $R_3'$, $R_4$, $R_5$, $R_6$, and n are as defined above; or a pharmaceutically acceptable salt thereof.

In some embodiments, $R_1$ is heteroaryl$_{(C≤12)}$. In some embodiments, $R_1$ is 5-pyrimidinyl. In some embodiments, $R_3$ is alkyl$_{(C≤12)}$. In some embodiments, $R_3$ is methyl or ethyl. In other embodiments, $R_3$ is hydrogen. In some embodiments, $R_3'$ is hydrogen.

In some embodiments, $R_4$ is alkyl$_{(C≤12)}$ or substituted alkyl$_{(C≤12)}$. In some embodiments, $R_4$ is alkyl$_{(C≤12)}$. In some embodiments, $R_4$ is methyl, ethyl, or isopropyl. In other embodiments, $R_4$ is substituted alkyl$_{(C≤12)}$. In some embodiments, $R_4$ is trifluoromethyl. In other embodiments, $R_4$ is cycloalkyl$_{(C≤12)}$ or substituted cycloalkyl$_{(C≤12)}$. In some embodiments, $R_4$ is cycloalkyl$_{(C≤12)}$. In some embodiments, $R_4$ is cyclopropyl, cyclopentyl, or cyclohexyl. In other embodiments, $R_4$ is aryl$_{(C≤12)}$. In some embodiments, $R_4$ is phenyl.

In some embodiments, $R_5$ is hydrogen. In other embodiments, $R_5$ is heteroaryl$_{(C≤12)}$. In some embodiments, $R_5$ is 4-methylimidazolyl. In other embodiments, $R_5$ is —X—$R_9$, wherein:

X is a covalent bond, alkanediyl$_{(C≤8)}$, or substituted alkanediyl$_{(C≤8)}$;

$R_9$ is amino or heterocycloalkyl$_{(C≤12)}$, heteroaryl$_{(C≤12)}$, alkylamino$_{(C≤12)}$, dialkylamino$_{(C≤12)}$, or a substituted version of any of these groups; or a group of the formula:

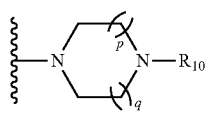

wherein:

$R_{10}$ is hydrogen, alkyl$_{(C≤12)}$, cycloalkyl$_{(C≤12)}$, substituted alkyl$_{(C≤12)}$, or substituted cycloalkyl$_{(C≤12)}$; and p and q are each 0, 1, or 2.

In some embodiments, X is alkanediyl$_{(C≤8)}$. In some embodiments, X is —$CH_2$— or —$CH_2CH_2$—. In some embodiments, $R_9$ is heterocycloalkyl$_{(C≤12)}$ or a substituted heterocycloalkyl$_{(C≤12)}$. In some embodiments, $R_9$ is N-1,4-thiazinanyl, N-morpholinyl, N-piperidinyl, N-pyrrolidinyl, or N-3-dimethylaminopyrrolidinyl. In other embodiments, $R_9$ is dialkylamino$_{(C≤12)}$ or substituted dialkylamino$_{(C≤12)}$. In some embodiments, $R_9$ is —$N(CH_3)CH_2CH_2N(CH_3)_2$. In other embodiments, $R_9$ is:

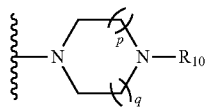

wherein:

$R_{10}$ is hydrogen, alkyl$_{(C≤12)}$, cycloalkyl$_{(C≤12)}$, substituted alkyl$_{(C≤12)}$, or substituted cycloalkyl$_{(C≤12)}$; and p and q are each 0, 1, or 2.

In some embodiments, $R_{10}$ is alkyl$_{(C≤12)}$ or substituted alkyl$_{(C≤12)}$. In some embodiments, $R_{10}$ is methyl or ethyl. In other embodiments, $R_{10}$ is cycloalkyl$_{(C≤12)}$ or substituted cycloalkyl$_{(C≤12)}$. In some embodiments, $R_{10}$ is cyclohexyl. In some embodiments, p is 1. In some embodiments, q is 1. In other embodiments, q is 2. In some embodiments, m is 0. In other embodiments, m is 1.

In some embodiments, $R_7$ is alkyl$_{(C≤8)}$ or substituted alkyl$_{(C≤8)}$. In some embodiments, $R_7$ is methyl. In other embodiments, $R_7$ is halo. In some embodiments, $R_7$ is fluoro or chloro.

In some embodiments, the compounds are further defined as:

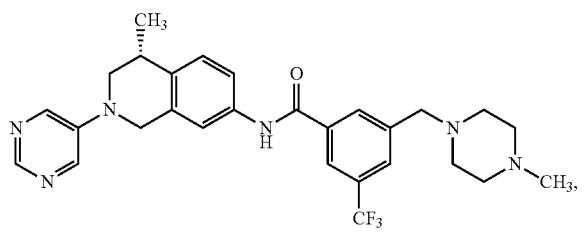

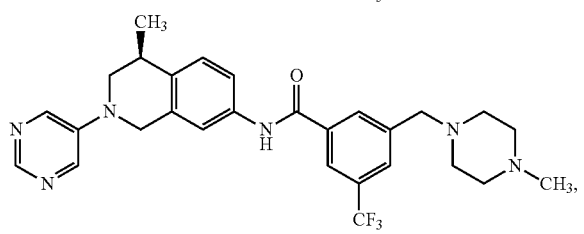

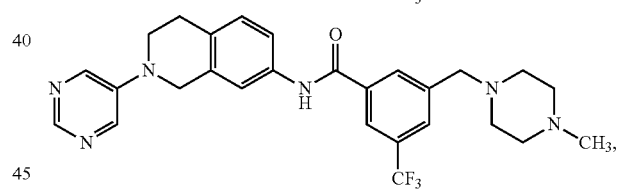

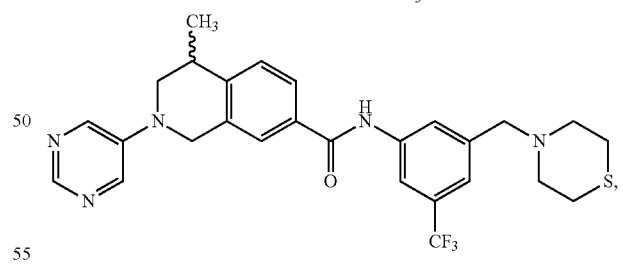

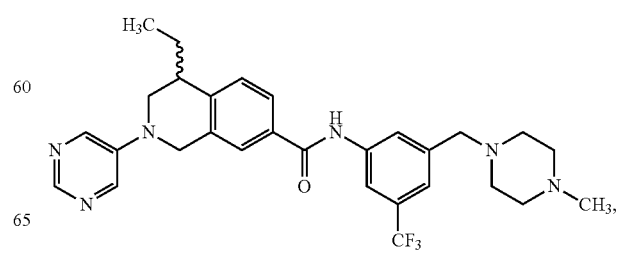

-continued
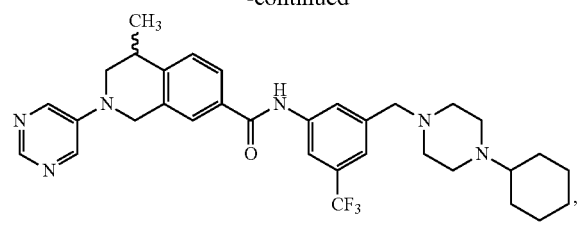
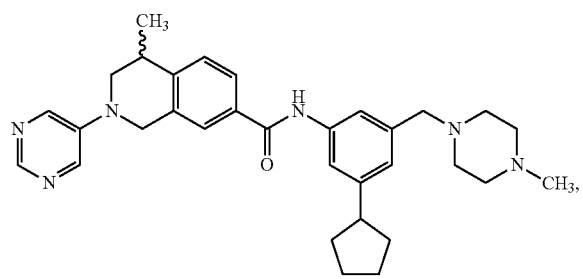
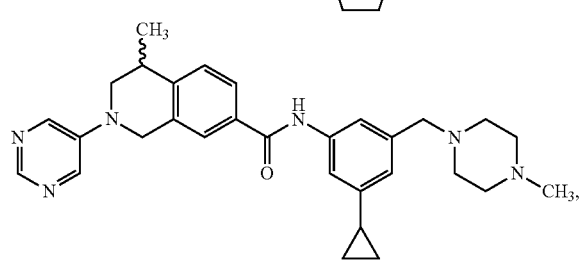
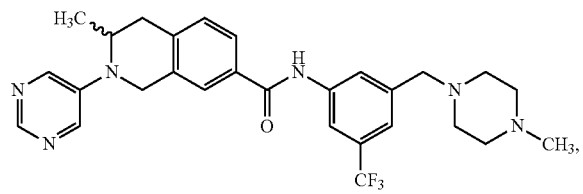
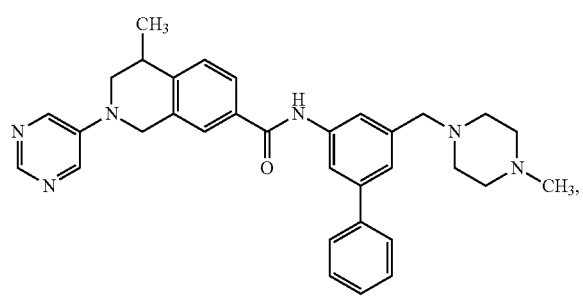
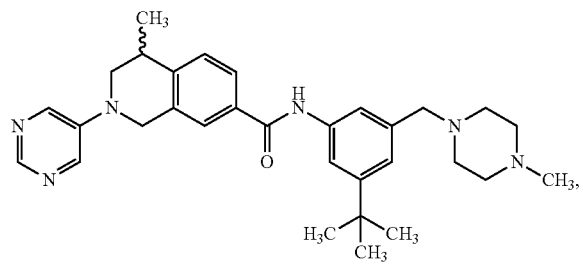
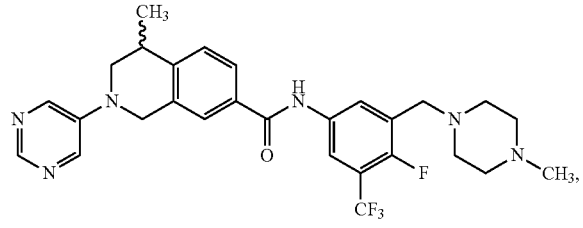
-continued
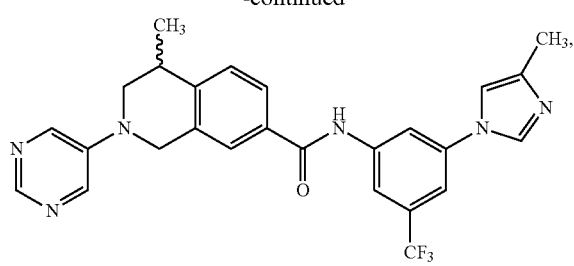
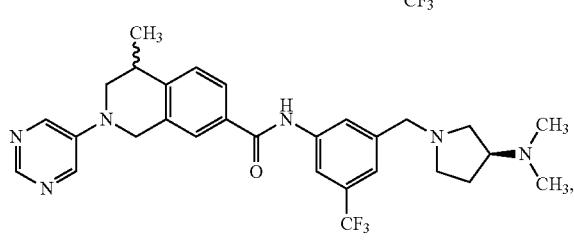
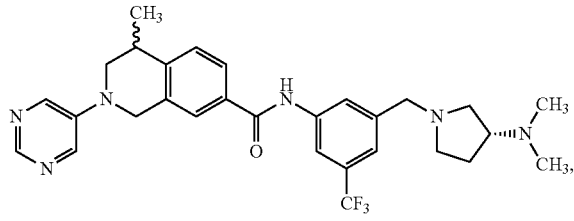
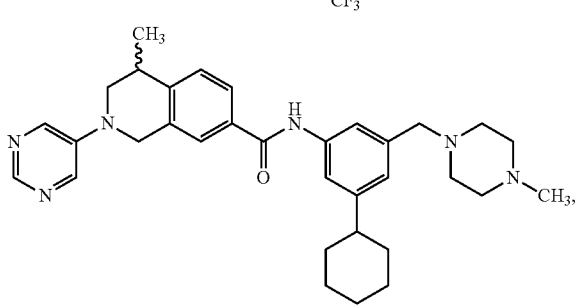
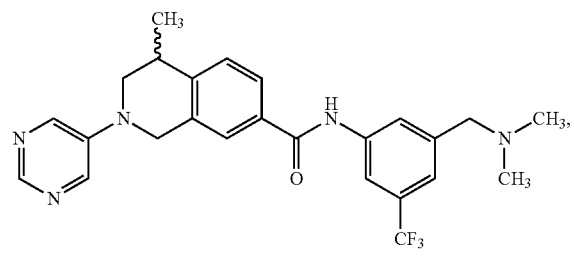
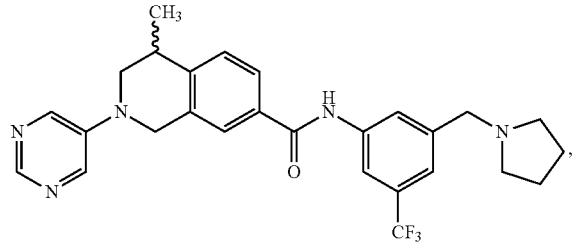

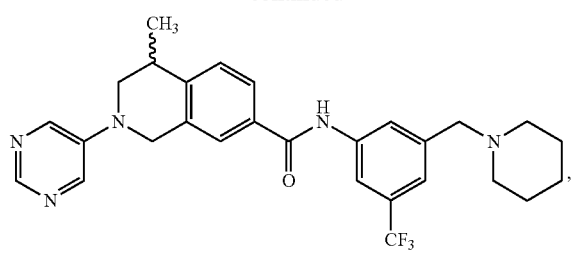
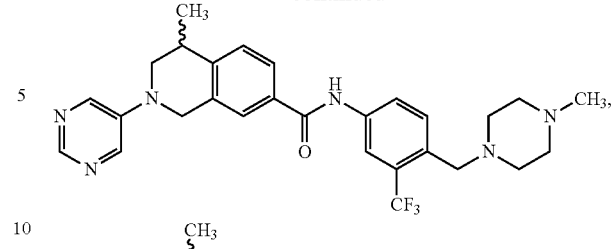
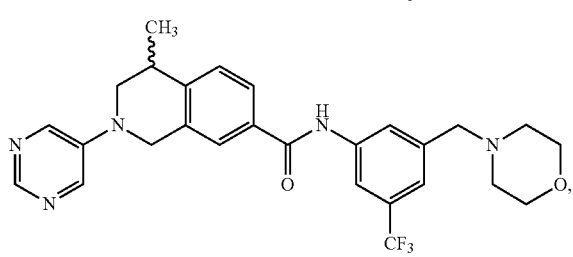
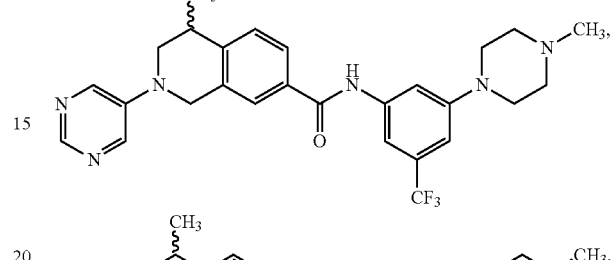
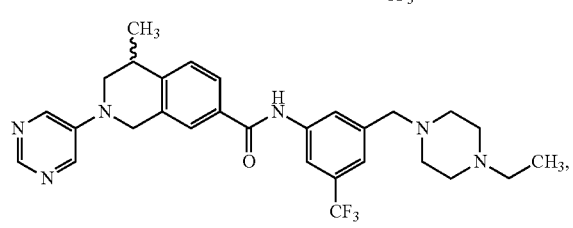
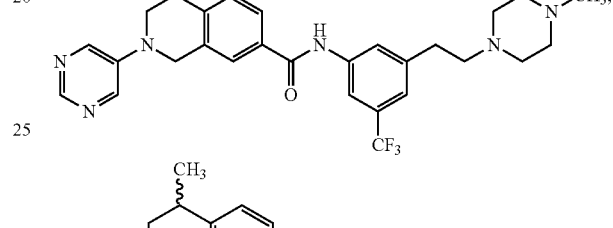
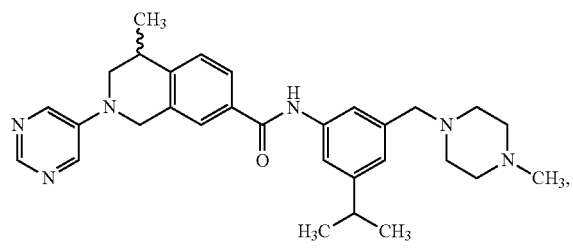
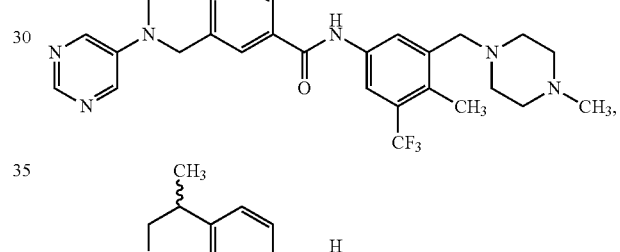
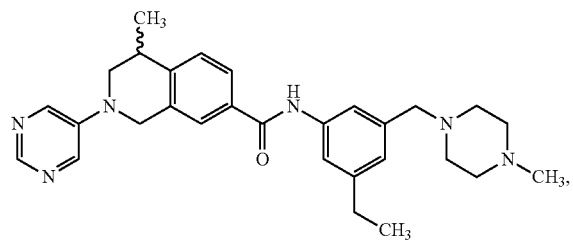
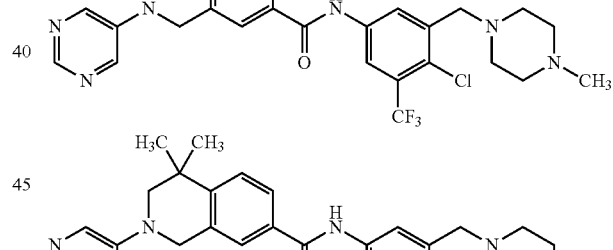
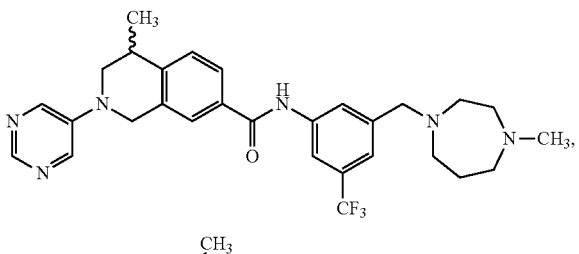
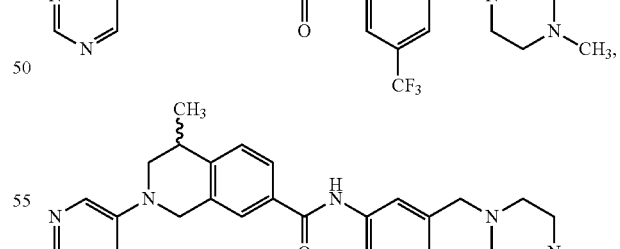
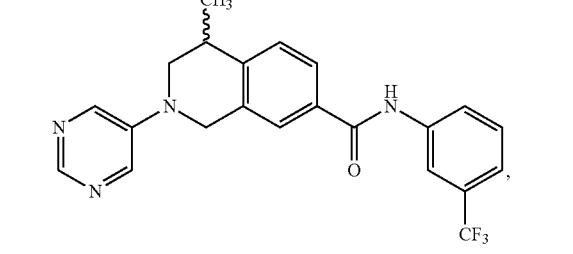
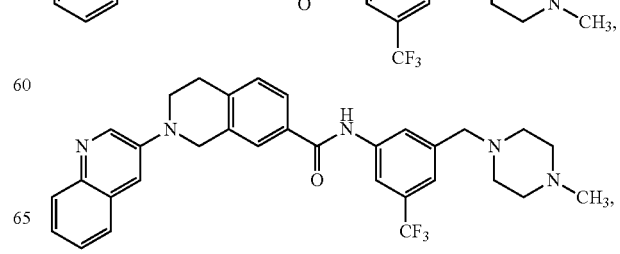

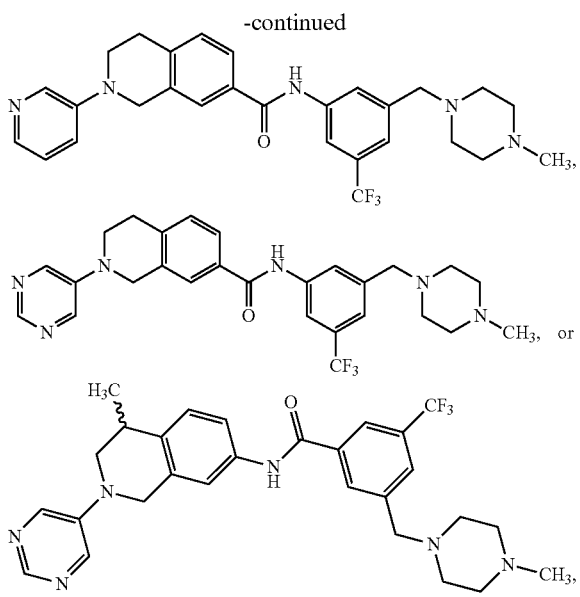

or a pharmaceutically acceptable salt thereof.

In still another aspect, the present disclosure provides compounds of the formula:

4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide;
N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(3-((4-methylpiperazin-1-yl)methyl)-5-(trifluoromethyl)phenyl)-2-(pyridin-3-yl)-1,2,3,4-tetrahydroisoquinoline-7-carboxamide;
N-(3-((4-methylpiperazin-1-yl)methyl)-5-(trifluoromethyl)phenyl)-2-(quinolin-3-yl)-1,2,3,4-tetrahydroisoquinoline-7-carboxamide;
4-methyl-N-(3-((4-methylpiperazin-1-yl)methyl)-5-(trifluoromethyl)phenyl)-2-(pyridin-3-yl)-1,2,3,4-tetrahydroisoquinoline-7-carboxamide;
4,4-dimethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(4-chloro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide;
4-methyl-N-(4-methyl-3-((4-methylpiperazin-1-yl)methyl)-5-(trifluoromethyl)phenyl)-2-(pyrimidin-5-yl)-1,2,3,4-tetrahydroisoquinoline-7-carboxamide;
4-methyl-N-(3-(2-(4-methylpiperazin-1-yl)ethyl)-5-(trifluoromethyl)phenyl)-2-(pyrimidin-5-yl)-1,2,3,4-tetrahydroisoquinoline-7-carboxamide;
4-methyl-N-(3-(4-methylpiperazin-1-yl)-5-(trifluoromethyl)phenyl)-2-(pyrimidin-5-yl)-1,2,3,4-tetrahydroisoquinoline-7-carboxamide;
4-methyl-N-(4-((4-methylpiperazin-1-yl)methyl)-3-(trifluoromethyl)phenyl)-2-(pyrimidin-5-yl)-1,2,3,4-tetrahydroisoquinoline-7-carboxamide;
4-methyl-2-(pyrimidin-5-yl)-N-(3-(trifluoromethyl)phenyl)-1,2,3,4-tetrahydroisoquinoline-7-carboxamide;
4-methyl-N-(3-((4-methyl-1,4-diazepan-1-yl)methyl)-5-(trifluoromethyl)phenyl)-2-(pyrimidin-5-yl)-1,2,3,4-tetrahydroisoquinoline-7-carboxamide;
N-(3-ethyl-5-((4-methylpiperazin-1-yl)methyl)phenyl)-4-methyl-2-(pyrimidin-5-yl)-1,2,3,4-tetrahydroisoquinoline-7-carboxamide;
N-(3-isopropyl-5-((4-methylpiperazin-1-yl)methyl)phenyl)-4-methyl-2-(pyrimidin-5-yl)-1,2,3,4-tetrahydroisoquinoline-7-carboxamide;
N-(3-((4-ethylpiperazin-1-yl)methyl)-5-(trifluoromethyl)phenyl)-4-methyl-2-(pyrimidin-5-yl)-1,2,3,4-tetrahydroisoquinoline-7-carboxamide;
4-methyl-N-(3-(morpholinomethyl)-5-(trifluoromethyl)phenyl)-2-(pyrimidin-5-yl)-1,2,3,4-tetrahydroisoquinoline-7-carboxamide;
4-methyl-N-(3-(piperidin-1-ylmethyl)-5-(trifluoromethyl)phenyl)-2-(pyrimidin-5-yl)-1,2,3,4-tetrahydroisoquinoline-7-carboxamide;
4-methyl-2-(pyrimidin-5-yl)-N-(3-(pyrrolidin-1-ylmethyl)-5-(trifluoromethyl)phenyl)-1,2,3,4-tetrahydroisoquinoline-7-carboxamide;
N-(3-((dimethylamino)methyl)-5-(trifluoromethyl)phenyl)-4-methyl-2-(pyrimidin-5-yl)-1,2,3,4-tetrahydroisoquinoline-7-carboxamide;
N-(3-cyclohexyl-5-((4-methylpiperazin-1-yl)methyl)phenyl)-4-methyl-2-(pyrimidin-5-yl)-1,2,3,4-tetrahydroisoquinoline-7-carboxamide;
N-(3-(((2-(dimethylamino)ethyl)(methyl)amino)methyl)-5-(trifluoromethyl)phenyl)-4-methyl-2-(pyrimidin-5-yl)-1,2,3,4-tetrahydroisoquinoline-7-carboxamide;
N-(3-(((R)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide;
N-(3-(((S)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide;
4-methyl-N-(3-(4-methyl-1H-imidazol-1-yl)-5-(trifluoromethyl)phenyl)-2-(pyrimidin-5-yl)-1,2,3,4-tetrahydroisoquinoline-7-carboxamide;
N-(4-fluoro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide;
N-(3-tert-butyl-5-((4-methylpiperazin-1-yl)methyl)phenyl)-4-methyl-2-(pyrimidin-5-yl)-1,2,3,4-tetrahydroisoquinoline-7-carboxamide;
4-methyl-N-(5-((4-methylpiperazin-1-yl)methyl)biphenyl-3-yl)-2-(pyrimidin-5-yl)-1,2,3,4-tetrahydroisoquinoline-7-carboxamide;
3-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(3-cyclopropyl-5-((4-methylpiperazin-1-yl)methyl)phenyl)-4-methyl-2-(pyrimidin-5-yl)-1,2,3,4-tetrahydroisoquinoline-7-carboxamide;
N-(3-cyclopentyl-5-((4-methylpiperazin-1-yl)methyl)phenyl)-4-methyl-2-(pyrimidin-5-yl)-1,2,3,4-tetrahydroisoquinoline-7-carboxamide;
N-(3-((4-cyclohexylpiperazin-1-yl)methyl)-5-(trifluoromethyl)phenyl)-4-methyl-2-(pyrimidin-5-yl)-1,2,3,4-tetrahydroisoquinoline-7-carboxamide;
4-ethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
4-methyl-2-(pyrimidin-5-yl)-N-(3-(thiomorpholinomethyl)-5-(trifluoromethyl)phenyl)-1,2,3,4-tetrahydroisoquinoline-7-carboxamide;
3-((4-methylpiperazin-1-yl)methyl)-N-(2-(pyrimidin-5-yl)-1,2,3,4-tetrahydroisoquinolin-7-yl)-5-(trifluoromethyl)benzamide;

(S)-4-methyl-N-(3-((4-methylpiperazin-1-yl)methyl)-5-(tri-fluoromethyl)phenyl)-2-(pyrimidin-5-yl)-1,2,3,4-tetrahy-droisoquinoline-7-carboxamide;

(R)-4-methyl-N-(3-((4-methylpiperazin-1-yl)methyl)-5-(tri-fluoromethyl)phenyl)-2-(pyrimidin-5-yl)-1,2,3,4-tetrahy-droisoquinoline-7-carboxamide;

(S)—N-(4-methyl-2-(pyrimidin-5-yl)-1,2,3,4-tetrahydroiso-quinolin-7-yl)-3-((4-methylpiperazin-1-yl)methyl)-5-(tri-fluoromethyl)benzamide;

(R)—N-(4-methyl-2-(pyrimidin-5-yl)-1,2,3,4-tetrahy-droisoquinolin-7-yl)-3-((4-methylpiperazin-1-yl)methyl)-5-(trifluoromethyl)benzamide;

or a pharmaceutically acceptable salt thereof.

In still yet another aspect, the present disclosure provides pharmaceutical composition comprising:

(a) a compound described herein; and (b) a pharmaceutically acceptable carrier.

In some embodiments, the pharmaceutical compositions further comprise a second chemotherapeutic compound. In some embodiments, the second chemotherapeutic compound is a nucleoside analog chemotherapeutic compound. In some embodiments, the nucleoside analog chemotherapeutic compound is gemcitabine. In other embodiments, the second chemotherapeutic compound is a taxane. In some embodiments, the second chemotherapeutic compound is paclitaxel. In some embodiments, the pharmaceutical composition is formulated for administration: orally, intraadi-posally, intraarterially, intraarticularly, intracranially, intra-dermally, intralesionally, intramuscularly, intranasally, intraocularly, intrapericardially, intraperitoneally, intrapleu-rally, intraprostatically, intrarectally, intrathecally, intratra-cheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, trans-dermally, vaginally, in crèmes, in lipid compositions, via a catheter, via a lavage, via continuous infusion, via infusion, via inhalation, via injection, via local delivery, or via local-ized perfusion. In some embodiments, the pharmaceutical composition is formulated for oral administration. In some embodiments, the pharmaceutical composition is formulated as a unit dose.

In still yet another aspect, the present disclosure provides pharmaceutical compositions comprising:

(a) a compound of the formula:

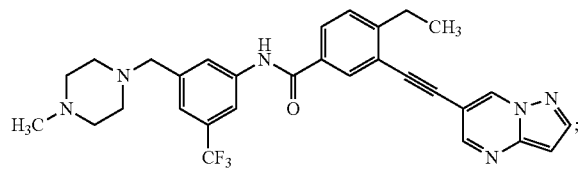 [SMILES: CCc1ccc(C(=O)Nc2cc(CN3CCN(C)CC3)cc(C(F)(F)F)c2)cc1C#Cc1cnc2ccnn2c1]

and (b) a second chemotherapeutic compound.

In some embodiments, the pharmaceutical composition further comprises a pharmaceutically acceptable carrier. In some embodiments, the pharmaceutical composition is for-mulated for oral administration. In some embodiments, the second chemotherapeutic compound is a nucleoside analog. In some embodiments, the second chemotherapeutic com-pound is gemcitabine. In other embodiments, the second chemotherapeutic compound is a taxane. In some embodi-ments, the second chemotherapeutic compound is paclitaxel. In some embodiments, the composition is formulated as a unit dose.

In still yet another aspect, the present disclosure provides methods of treating a disease or disorder in a patient in need thereof comprising administering to the patient a therapeu-tically effective amount of a compound or composition described herein. In some embodiments, the disease or disorder is related to inflammation. In some embodiments, the disease or disorder is kidney fibrosis, liver fibrosis, lung fibrosis, skin scars, or atherosclerosis. In other embodi-ments, the disease or disorder is cancer. In some embodi-ments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gas-trointestinal tract, genitalia, genitourinary tract, head, kid-ney, larynx, liver, lung, muscle tissue, neck, oral or nasal mucosa, ovary, pancreas, prostate, skin, spleen, small intes-tine, large intestine, stomach, testicle, or thyroid. In some embodiments, the cancer is a cancer of the lung, breast, brain, ovary, head and neck, liver, pancreas, or prostate. In some embodiments, the cancer is a cancer of the pancreas. In some embodiments, the cancer is pancreatic ductal adeno-carcinoma. In some embodiments, the compound is admin-istered to the patient once. In other embodiments, the compound is administered to the patient two or more times. In some embodiments, the methods further comprise a second therapy. In some embodiments, the second therapy is one or more therapeutic agents, a surgery, a radiotherapy, or an immunotherapy. In some embodiments, the second therapy is a chemotherapeutic agent. In some embodiments, the second therapy is a nucleoside analog chemotherapeutic agent. In some embodiments, the nucleoside analog chemo-therapeutic agent is gemcitabine. In other embodiments, the second therapy is a taxane. In some embodiments, the second therapy is paclitaxel.

In still another aspect, the present disclosure provides methods of inhibiting discoidin domain receptor (DDR) protein comprising contacting the protein with a compound or composition described herein in an amount sufficient to inhibit the protein. In some embodiments, the protein is the discoidin domain receptor 1 protein (DDR1). In some embodiments, the methods are performed in vivo. In other embodiments, the methods are performed in vitro. In some embodiments, the methods are performed in vivo and com-prise administering the compound to a patient in need thereof. In some embodiments, the inhibition of DDR1 protein is sufficient to treat a disease or disorder.

In still yet another aspect, the present disclosure provides methods of treating cancer in a patient in need thereof comprising administering to the patient a therapeutically effective amount of:

(a) a compound or composition described herein; and (b) a second chemotherapeutic compound.

In some embodiments, the cancer is a cancer of the lung, breast, brain, ovary, head and neck, liver, pancreas, or prostate. In some embodiments, the cancer is a cancer of the pancreas. In some embodiments, the cancer is pancreatic ductal adenocarcinoma. In some embodiments, the methods comprise administering the compound or composition in a ratio from about 1:2 to about 5:1 relative to the second chemotherapeutic compound. In some embodiments, the ratio of the compound or composition is 2:1 relative to the second chemotherapeutic compound. In some embodiments, the second chemotherapeutic compound is a nucleoside analog. In some embodiments, the second chemotherapeutic compound is gemcitabine. In other embodiments, the second chemotherapeutic compound is a taxane. In some embodiments, the second chemotherapeutic compound is paclitaxel.

In still another aspect, the present disclosure provides compounds of formula (IV) or a pharmaceutically acceptable salt, stereoisomer or prodrug thereof:

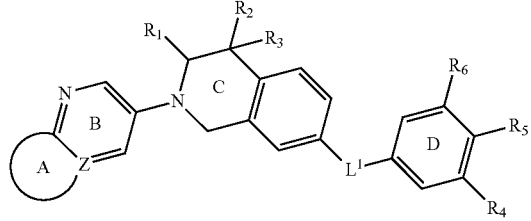

(IV)

wherein $L^1$ is independently selected as —CONH— or —NHCO—;

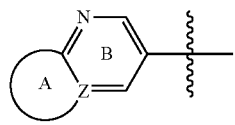

is independently selected from:
a) single heterocycles like

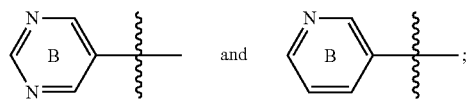

b) fused heterocycles like

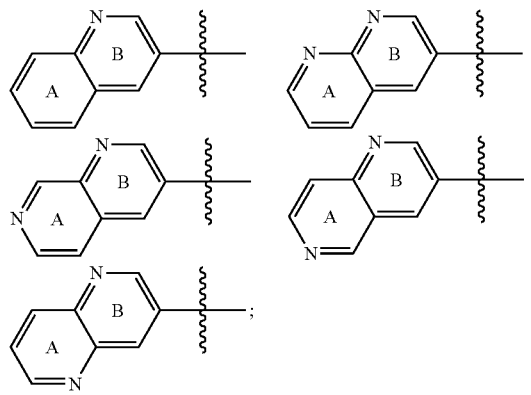

$R_1$, $R_2$, $R_3$ are independently selected from:
a) H;
b) $C_1$~$C_4$ alkyl;
$R_2$, $R_3$ can further form tri, tetra, penta ring structure with the carbon atom where they are linked in the C ring;
$R_4$, $R_5$, $R_6$ is independently selected from:
a) H;
b) halogen (F, Cl, Br);
c) $C_1$~$C_4$ alkyl;
d) $C_3$~$C_6$ cycloalkyl;
e) $C_1$~$C_4$ alkyl containing F;
f) aryl, Het;
aryl can be phenyl, or substituted phenyl; Het is defined as the nonaromatic heterocycle, or aromatic heterocycle containing 5~6 atoms, which contains 1~4 hetero atoms such as O, N, S. Alkyl or cycloalkyl will be incorporated into any C or N position in which Het can be substituted.

In some embodiments, $R_1$, $R_2$, $R_3$ is independently selected from:
a) H;
b) methyl, ethyl, propyl, isopropyl, cyclopropyl;
R2, R3 can further form tri, tetra, penta ring structure with the carbon atom where they are linked in the C ring.

In some embodiments, D ring is selected from:

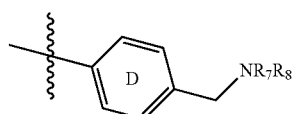

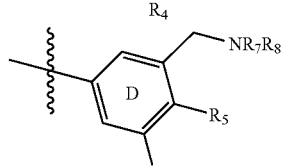

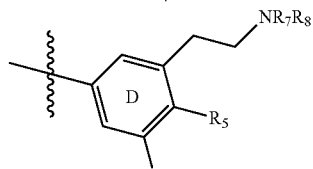

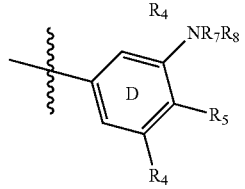

$R_4$ is independently selected from:
a) halogen (F, Cl, Br);
b) $C_1$~$C_4$ alkyl;
c) $C_3$~$C_6$ cycloalkyl;
d) $C_1$~$C_4$ alkyl containing F;
e) aryl;
Aryl can be phenyl, or substituted phenyl;
$R_5$ is independently selected from H, F, Cl, Br, Me, OMe;
$R_7$ or $R_8$ is independently selected from:
a) H;
b) $C_1$~$C_3$ alkyl;
c) $C_1$~$C_3$ alkyl containing F;
d) $C_3$~$C_6$ cycloalkyl;
$R_7$ and $R_8$ can further form penta-, hexa-, hepta- or octatomic ring structure through C, O, N, S atoms. Alkyl or cycloalkyl will be incorporated into any C or N position in the ring which can be substituted; preferably,

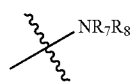
is independently selected from:
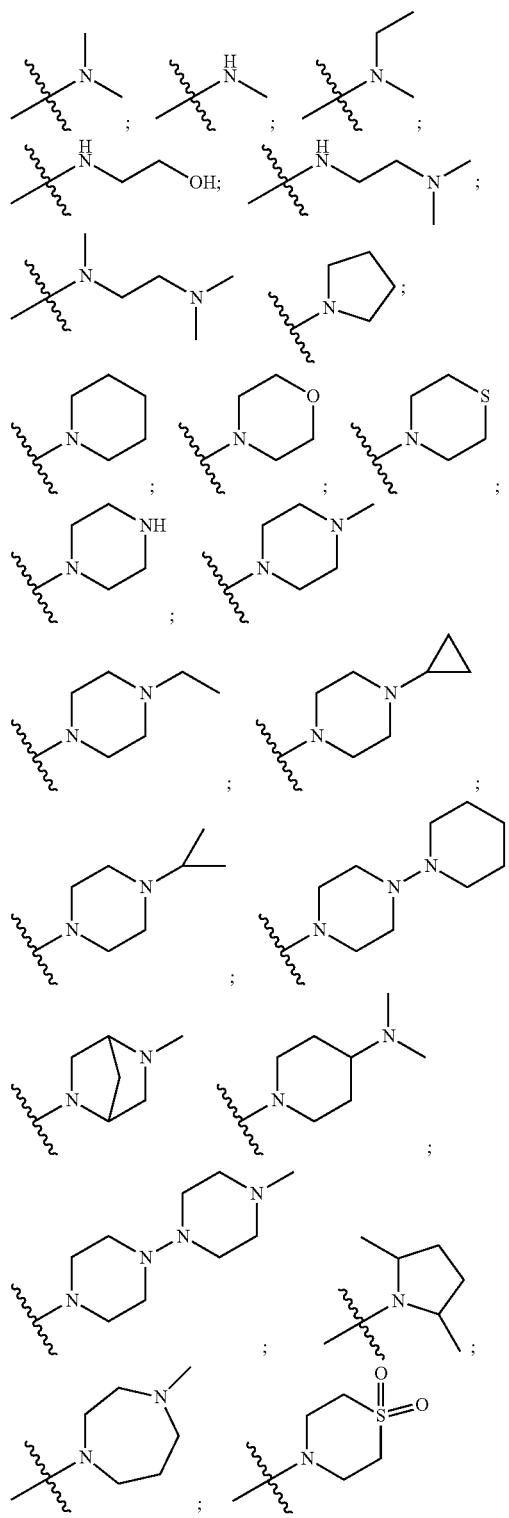
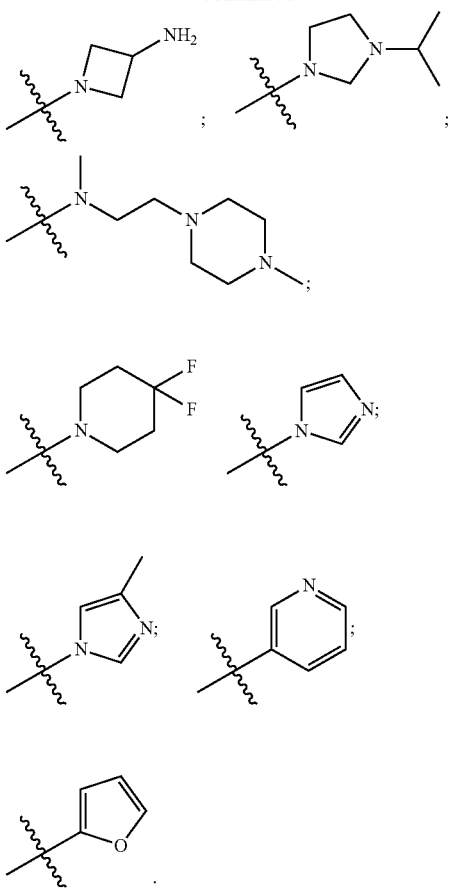
In some embodiments, the compound of formula (IV) is specially selected from:
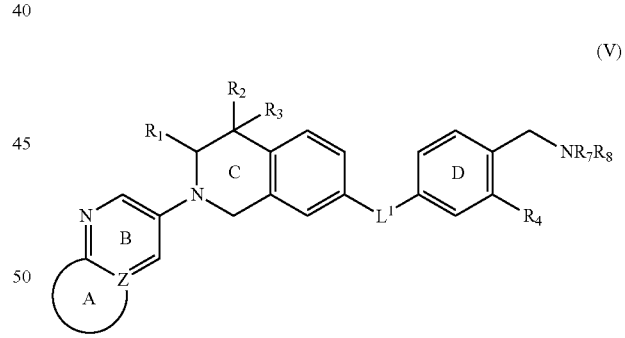
(V)
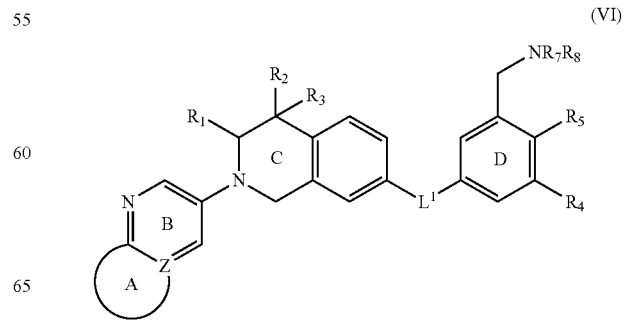
(VI)

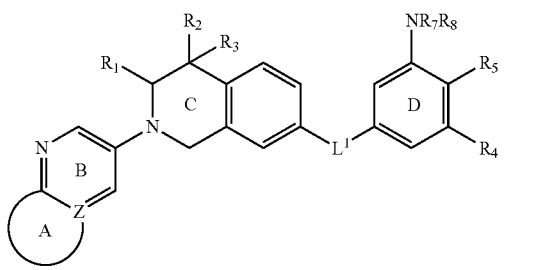

(VII)

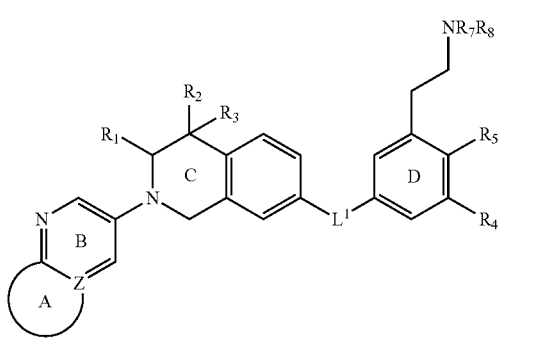

(VIII)

wherein
L¹ is independently selected as —CONH— or —NHCO—;

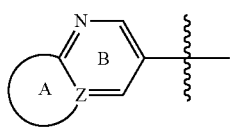

is independently selected from:

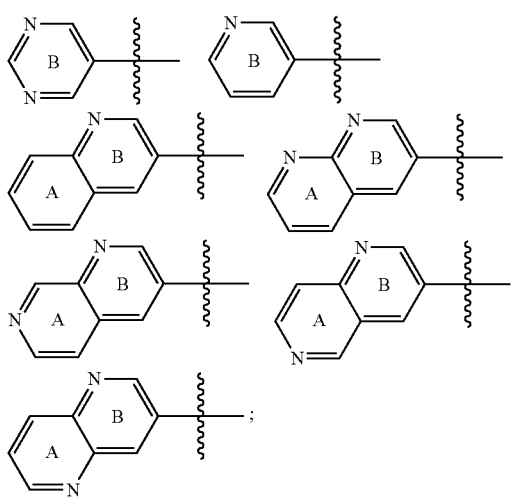

$R_1$, $R_2$, $R_3$, $R_4$, $R_5$, $R_7$, $R_8$ have the same definition as above mentioned.

In some embodiments, the compounds of formula (IV) are specially selected from:

4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide;

N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

N-(3-((4-methylpiperazin-1-yl)methyl)-5-(trifluoromethyl)phenyl)-2-(pyridin-3-yl)-1,2,3,4-tetrahydroisoquinoline-7-carboxamide;

N-(3-((4-methylpiperazin-1-yl)methyl)-5-(trifluoromethyl)phenyl)-2-(quinolin-3-yl)-1,2,3,4-tetrahydroisoquinoline-7-carboxamide;

4-methyl-N-(3-((4-methylpiperazin-1-yl)methyl)-5-(trifluoromethyl)phenyl)-2-(pyridin-3-yl)-1,2,3,4-tetrahydroisoquinoline-7-carboxamide;

4,4-dimethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

N-(4-chloro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide;

4-methyl-N-(4-methyl-3-((4-methylpiperazin-1-yl)methyl)-5-(trifluoromethyl)phenyl)-2-(pyrimidin-5-yl)-1,2,3,4-tetrahydroisoquinoline-7-carboxamide;

4-methyl-N-(3-(2-(4-methylpiperazin-1-yl)ethyl)-5-(trifluoromethyl)phenyl)-2-(pyrimidin-5-yl)-1,2,3,4-tetrahydroisoquinoline-7-carboxamide;

4-methyl-N-(3-(4-methylpiperazin-1-yl)-5-(trifluoromethyl)phenyl)-2-(pyrimidin-5-yl)-1,2,3,4-tetrahydroisoquinoline-7-carboxamide;

4-methyl-N-(4-((4-methylpiperazin-1-yl)methyl)-3-(trifluoromethyl)phenyl)-2-(pyrimidin-5-yl)-1,2,3,4-tetrahydroisoquinoline-7-carboxamide;

4-methyl-2-(pyrimidin-5-yl)-N-(3-(trifluoromethyl)phenyl)-1,2,3,4-tetrahydroisoquinoline-7-carboxamide;

4-methyl-N-(3-((4-methyl-1,4-diazepan-1-yl)methyl)-5-(trifluoromethyl)phenyl)-2-(pyrimidin-5-yl)-1,2,3,4-tetrahydroisoquinoline-7-carboxamide;

N-(3-ethyl-5-((4-methylpiperazin-1-yl)methyl)phenyl)-4-methyl-2-(pyrimidin-5-yl)-1,2,3,4-tetrahydroisoquinoline-7-carboxamide;

N-(3-isopropyl-5-((4-methylpiperazin-1-yl)methyl)phenyl)-4-methyl-2-(pyrimidin-5-yl)-1,2,3,4-tetrahydroisoquinoline-7-carboxamide;

N-(3-((4-ethylpiperazin-1-yl)methyl)-5-(trifluoromethyl)phenyl)-4-methyl-2-(pyrimidin-5-yl)-1,2,3,4-tetrahydroisoquinoline-7-carboxamide;

4-methyl-N-(3-(morpholinomethyl)-5-(trifluoromethyl)phenyl)-2-(pyrimidin-5-yl)-1,2,3,4-tetrahydroisoquinoline-7-carboxamide;

4-methyl-N-(3-(piperidin-1-ylmethyl)-5-(trifluoromethyl)phenyl)-2-(pyrimidin-5-yl)-1,2,3,4-tetrahydroisoquinoline-7-carboxamide;

4-methyl-2-(pyrimidin-5-yl)-N-(3-(pyrrolidin-1-ylmethyl)-5-(trifluoromethyl)phenyl)-1,2,3,4-tetrahydroisoquinoline-7-carboxamide;

N-(3-((dimethylamino)methyl)-5-(trifluoromethyl)phenyl)-4-methyl-2-(pyrimidin-5-yl)-1,2,3,4-tetrahydroisoquinoline-7-carboxamide;

N-(3-cyclohexyl-5-((4-methylpiperazin-1-yl)methyl)phenyl)-4-methyl-2-(pyrimidin-5-yl)-1,2,3,4-tetrahydroisoquinoline-7-carboxamide;

N-(3-(((2-(dimethylamino)ethyl)(methyl)amino)methyl)-5-(trifluoromethyl)phenyl)-4-methyl-2-(pyrimidin-5-yl)-1,2,3,4-tetrahydroisoquinoline-7-carboxamide;

N-(3-(((R)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide;

N-(3-(((S)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide;

4-methyl-N-(3-(4-methyl-1H-imidazol-1-yl)-5-(trifluoromethyl)phenyl)-2-(pyrimidin-5-yl)-1,2,3,4-tetrahydroisoquinoline-7-carboxamide;

N-(4-fluoro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide;

N-(3-tert-butyl-5-((4-methylpiperazin-1-yl)methyl)phenyl)-4-methyl-2-(pyrimidin-5-yl)-1,2,3,4-tetrahydroisoquinoline-7-carboxamide;

4-methyl-N-(5-((4-methylpiperazin-1-yl)methyl)biphenyl-3-yl)-2-(pyrimidin-5-yl)-1,2,3,4-tetrahydroisoquinoline-7-carboxamide;

3-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

N-(3-cyclopropyl-5-((4-methylpiperazin-1-yl)methyl)phenyl)-4-methyl-2-(pyrimidin-5-yl)-1,2,3,4-tetrahydroisoquinoline-7-carboxamide;

N-(3-cyclopentyl-5-((4-methylpiperazin-1-yl)methyl)phenyl)-4-methyl-2-(pyrimidin-5-yl)-1,2,3,4-tetrahydroisoquinoline-7-carboxamide;

N-(3-((4-cyclohexylpiperazin-1-yl)methyl)-5-(trifluoromethyl)phenyl)-4-methyl-2-(pyrimidin-5-yl)-1,2,3,4-tetrahydroisoquinoline-7-carboxamide;

4-ethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

4-methyl-2-(pyrimidin-5-yl)-N-(3-(thiomorpholinomethyl)-5-(trifluoromethyl)phenyl)-1,2,3,4-tetrahydroisoquinoline-7-carboxamide;

3-((4-methylpiperazin-1-yl)methyl)-N-(2-(pyrimidin-5-yl)-1,2,3,4-tetrahydroisoquinolin-7-yl)-5-(trifluoromethyl)benzamide;

(S)-4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

(R)-4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

(S)—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide; and (R)—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide.

In still yet another aspect, the present disclosure provides pharmaceutical compositions comprising a compound described herein or a pharmaceutically acceptable salt, stereoisomer or prodrug thereof and a pharmaceutically acceptable carrier, solvent, buffer or diluent.

In yet another aspect, the present disclosure provides methods of treating a subject having inflammation, liver fibrosis, kidney fibrosis, lung fibrosis, skin scar and atherosclerosis, and cancer comprising administering to said subject a compound described herein or a pharmaceutically acceptable salt, stereoisomer or pro-drug thereof.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-E: DDR1 signaling in human and mouse PDA. (FIG. 1A) 168 human PDA samples were assessed for expression of COLLAGEN I α1 (COLI α1), DDR1, PYK2, and PEAK1. RNA-sequencing data from The Cancer Genome Atlas (TCGA) PDA cBioPortal was collected (Cerami et al., 2012 and Gao et al., 2013). Relative changes (G score) were assessed by comparing RNA sequencing data between normal and cancer patients to define high and low expression. (FIG. 1B) Immunohistochemical detection of phospho-DDR1 and phospho-PEAK1 in human PDA. TMAs of primary human PDA (44 samples) and matched patient-derived tumor xenograft (PATX, 150 samples) demonstrated phospho-DDR1 and phospho-PEAK1 localized to similar regions. (FIGS. 1C-1E) Histological analyses of the KPC (LSL-Kras$^{G12D/+}$; LSL-Trp53$^{R172H/+}$; p48$^{Cre/+}$) GEMM of PDA. (FIG. 1C) Immunohistochemical detection of phospho-Ddr1, phospho-Peak1, phospho-Pyk2, Muc1 and Sox9 in KPC tumors. Ddr1 activation and downstream signaling through effectors such as Peak1 and Pyk2 was present in early PanIN lesions (similar to regions positive for Muc-1 staining) and in advanced adenocarcinoma (similar to regions of Sox9 staining). Tissue from an early (3 month) and advanced (5 month) stage of the KPC model was evaluated. (FIG. 1D) H&E histology of normal WT pancreas and PDA in a 5 month old KPC mouse. (FIG. 1E) Trichrome analysis of PDA from 3 and 5 month old KPC animals.

(FIG. 2A) Analyses of the expression of DDR1 and Collagen I α1 in lung cancer patients using the online database (Kaplan-Meier Plotter) (Gyorffy et al., 2013). Lung cancer patients with high expression of DDR1 (1,389/1,927) and those with high expression of Collagen I α1 (1,309/1,927) levels displayed worse overall prognosis. (FIG. 2B) Pearson correlation of p-PEAK1 and p-DDR1 expression in human and patient-derived tumor xenograft (PATX) TMA samples. (FIG. 2C) Percent of TMA samples positive for p-DDR1 and p-PEAK1. Scoring system is denoted as: low or no reactivity (0-1), moderate reactivity (2), strong reactivity (3), and very strong reactivity (4).

FIGS. 3A-J: Analysis of PDA GEMM for collagen deposition and Ddr1 signaling. Histological analyses of the KPC (LSL-Kras$^{G12D/+}$; LSL-Trp53$^{R172H/+}$; p48$^{Cre/+}$) GEMM of PDA. (FIGS. 3A-B) The KPC model recapitulated the pathological histology seen in human PDA as noted by the dense stromal reaction. (FIGS. 3C-D) Trichrome analyses depicted the enhanced desmoplasia throughout the progression of the model. (FIGS. 3E-F) Histological analyses represent metastatic lesions in the liver. Phosphorylation of Ddr1 (FIG. 3G) and Peak1 (FIG. 3H) colocalized to metastatic regions. Metastatic regions were validated by the expression of the mesenchymal marker vimentin (FIG. 3I) and the tumorigenic marker Pcna (FIG. 3J).

FIGS. 4A-H: Collagen stimulation of DDR1 signaling in human PDA cell lines. (FIG. 4A) Collagen receptor expression profile of human PDA cell lines (AsPC-1 and PANC-1). Each cell line expressed similar levels of DDR1, PEAK1, INTEGRIN α1 (ITG α1), INTEGRIN β1 (ITG β1), COLLAGEN I α1 (COL I α1), and COLLAGEN I α2 (COL I α2) as determined by PCR analysis (30 cycles). (FIG. 4B) Secretion of soluble collagen (μg) was assessed in duplicate samples of human PDA cells by Sircol analysis. AsPC-1 secreted an elevated level of collagen compared to PANC-1 cells. (FIG. 4C) Human PDA cell lines were plated on plastic (P) and stimulated with soluble collagen I (C, 10 μg/mL) for 24 hours. Lysates were probed for the indicated targets by western blot analysis. (FIG. 4D) Human PDA cell lines were plated in the presence or absence of 10 μg/ml soluble collagen I. The presence of soluble collagen enhanced the phosphorylation of Peak1 by immunofluorescence. (FIG. 4E) Immunoprecipitation (IP) analysis of DDR1. IP of DDR1 co-precipitated PYK2 and PEAK1, but did not pull down αv integrin (ITG αV) or phospho-β1 integrin (P-ITG β1) (as shown in the immunodepleted (IDE) fraction. (FIG. 4F) siRNA-mediated knockdown of DDR1 compared to mock siRNA control reduced the activation of DDR1, PYK2, SRC, PEAK1, SHC, and AKT1. Lysates were probed for the indicated targets by western blot analysis. (FIG. 4G) siRNA-mediated knockdown of DDR1 compared to mock siRNA control reduced the activation of DDR1 through immunofluorescence. (FIG. 4H) siRNA-mediated knockdown of DDR1 compared to mock siRNA control reduced the migration of human PDA cells (AsPC-1) after a 24 hour period of time via scratch migration assay. Error bars: (*, $p<0.05$; , $p<0.005$; *, $p<0.0005$; ****, $p<0.00005$), one-way ANOVA with Tukey's MCT.

FIGS. 5A-D: Signaling and functional consequences of DDR1 inhibition by 7rh in human PDA cell lines. (FIG. 5A) 7rh inhibited DDR1-mediated signaling in a concentration-dependent manner in human PDA cell line PANC-1. PANC-1 cells were stimulated with control (no treatment) or collagen (10 μg/mL) for 24 hr and cell lysates were probed for the indicated targets by western blot analysis. (FIG. 5B) 7rh inhibited migration of human PDA cell lines in a concentration-dependent manner over a 30 hour time period via scratch migration assay. (FIG. 5C) 7rh inhibited liquid colony formation of human PDA cell lines in a concentration-dependent manner. 250 cells/well were plated in serum containing media in the presence or absence of 7rh at the indicated concentrations. Colony formation was evaluated 1.5-2 weeks post plating. (FIG. 5D) Sensitivity of human PDA cell lines (AsPC-1 and PANC-1) to gemcitabine and 7rh assessed by MTS viability assays. Drug sensitivity was assessed in the presence of 4-fold dilutions of each drug. Combination of 7rh (250 nM or 500 nM) with a titration of gemcitabine is shown. Drug sensitivity curves and $IC_{50}$s were calculated with in-house software, the number replicates for each assay is shown (#) (Dineen et al., 2010).

(FIG. 7A) Schematic representation of the animal experiment. Pan02 cells were orthotopically injected into C57BL/6 mice. Mice were terated with a one-time oral dose of 7rh (0.1, 1, or 10 mg/kg) on day 10 post tumor cell injection (TCI). (FIGS. 7B-7D) Immunofluorescence analysis of tumor tissue from each group showing inhibition of Ddr1 activation and downstream signaling (P-Pyk2 and P-Peak1), as well a significant induction of apoptosis (cleaved caspase-3, FIG. 7E). Mean+/−SEM % Area Fraction for p-Ddr1, p-Pyk2, p-Peak1 and cleaved caspase 3 are shown. *, $p<0.05$; , $p<0.005$; *, $p<0.0005$; ****, $p<0.00005$ v vehicle, one-way ANOVA with Tukey's MCT. Scale bar, 50 μm.

(FIG. 8A) Schematic representation of the animal experiment. Pan02 cells were orthotopically injected into C57BL/6 mice. 7rh was given orally 3×/week at the indicated concentrations starting on day 10 post tumor cell injection (TCI) and ended at day 21. (FIG. 8B) Tumor H&E histology is shown. (FIGS. 8C-F) Immunofluorescence analysis of amylase (FIG. 8C), p-Ddr1 (FIG. 8D), P-Peak1 (FIG. 8E), and PCNA (FIG. 8F) expression in tumor tissue from each group is shown. Mean+/−SEM of % Area Fraction is graphed. *, $p<0.05$; , $p<0.005$; *, $p<0.0005$; ****, $p<0.00005$ v vehicle, one-way ANOVA with Tukey's MCT. Scale bar, 50 μm. (FIG. 8G) The expression level of p-Peak1 in tumor lysates from each treatment group was determined by western blot analysis. Actin was used as a loading control.

(FIG. 9A) Serum from C57Bl/6 mice bearing orthotopic Pan02 tumors treated with vehicle or 7rh (3.3, 10 or 30 mg/kg) 3×/week for 2 weeks was collected at the time of sacrifice. The serum level of Alb (albumin), Alt (liver transaminases), Ast (aspartate transaminase), Bun (blood urea nitrogen), Crea (creatine), Glu (glucose), Tbil (total bilirubin), and Tp (plasma total protein) is shown. (FIG. 9B) Animal weights for each treatment group during the treatment period are displayed. *, $p<0.05$; , $p<0.005$; *, $p<0.0005$; ****, $p<0.00005$ v vehicle, one-way ANOVA with Tukey's MCT.

(FIG. 10A) Schematic representation of the animal experiment. Mouse Pan02 cells were orthotopically injected into C57BL/6 mice. 7rh (25 mg/kg 3×/week, n=8) was adminstered by oral gavage starting at day 19. (FIG. 10B) 7rh treatment reduced primary tumor burden compared to vehicle (n=10). (FIGS. 10C-10I) Tumor tissue harvested from vehicle or 7rh treated animals was evaluated by histology (FIGS. 10C, H&E) and immunofluorescence (FIGS. 10D-10I). Example reactivity for amylase (FIG. 10D), p-DDR1 (FIG. 10E), p-Peak1 (FIG. 10F), p-Pyk2 (FIG. 10G), cleaved caspase (FIG. 10H), and Pcna (FIG. 10I) are shown. Mean+/−SEM % are a fraction of signal intensity for each target is shown in the bar graphs. *, $p<0.05$; , $p<0.005$; *, $p<0.0005$; ****, $p<0.00005$. Scale bar, 50 μm.

(FIG. 11A) Schematic representation of the animal experiment. NOD-SCID mice (n=15/grp) were orthopically injected with AsPC-1 cells on day 0. Therapy with vehicle, 7rh (25 mg/kg, 3×/week via oral gavage), chemotherapy (gemcitabine, 12.5 mg/kg, 2×/week given ip; +nab-paclitaxel, 5 mg/kg, 2×/week given ip), or the combination of 7rh+chemotherapy was started on day 27 post tumor cell injection (TCI). Three animals/grp were sacrificed on day 28. (FIGS. 11B & 11C) 7rh combined with chemotherapy significantly enhanced the overall median of survival compared to single agent therapy. Treatment was withdrawn from animals in the combo group that were alive at day 102 (withdrawn). (FIG. 11D) Example H&E histology. (FIGS.

11E-11K) Immunofluorescence analysis of PDA tumors from each group for pDDR1 (FIG. 11E), pPYK2 (FIG. 11F), p-PEAK1 (FIG. 11G), Vimentin (FIG. 11I), PCNA (FIG. 11J), cleaved caspase-3 (FIG. 11K) and γH2AX (FIG. 11L) is shown. DAPI was used as a nuclear counterstain (FIGS. 11E-11K). Mean+/−SEM % Area Fraction is graphed. *, $p<0.05$; , $p<0.005$; *, $p<0.0005$; **** $p<0.00005$ v initial group; ^, $p<0.05$; ^^, $p<0.005$; ^^^, $p<0.0005$; ^^^^, $p<0.00005$ v vehicle group, one-way ANOVA with Tukey's MCT. Scale bar, 50 μm.

Figure 12A:
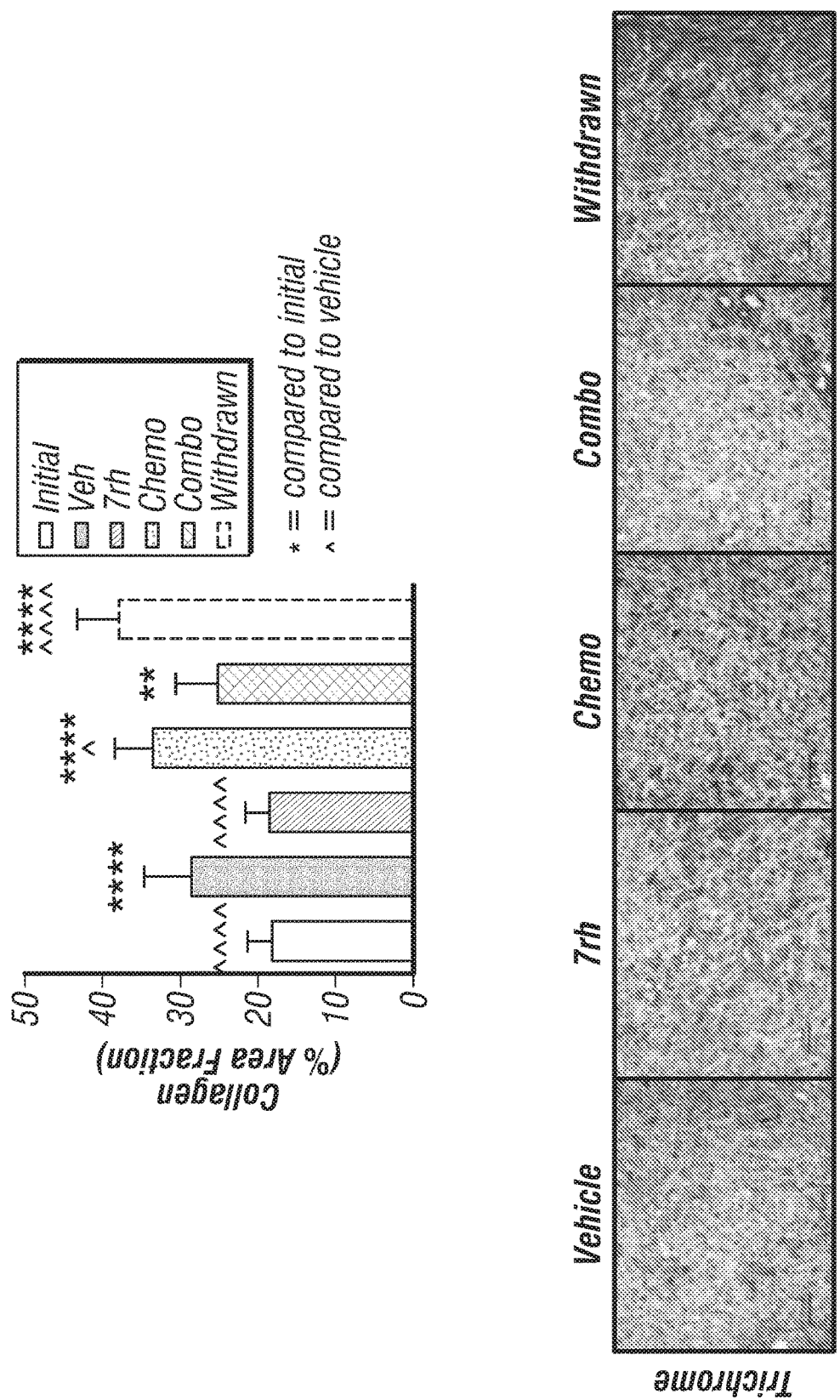
Figure 12B:
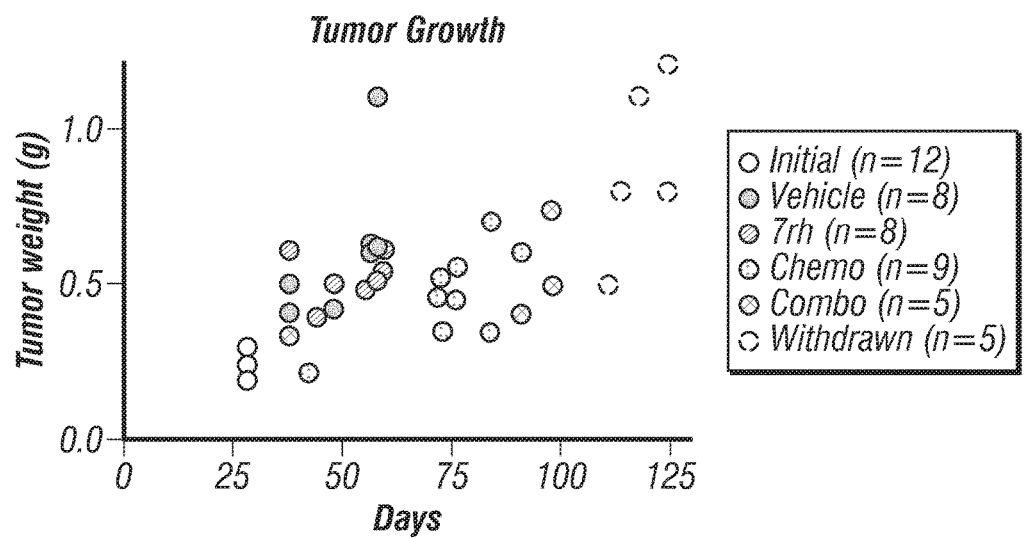
Figure 12C:
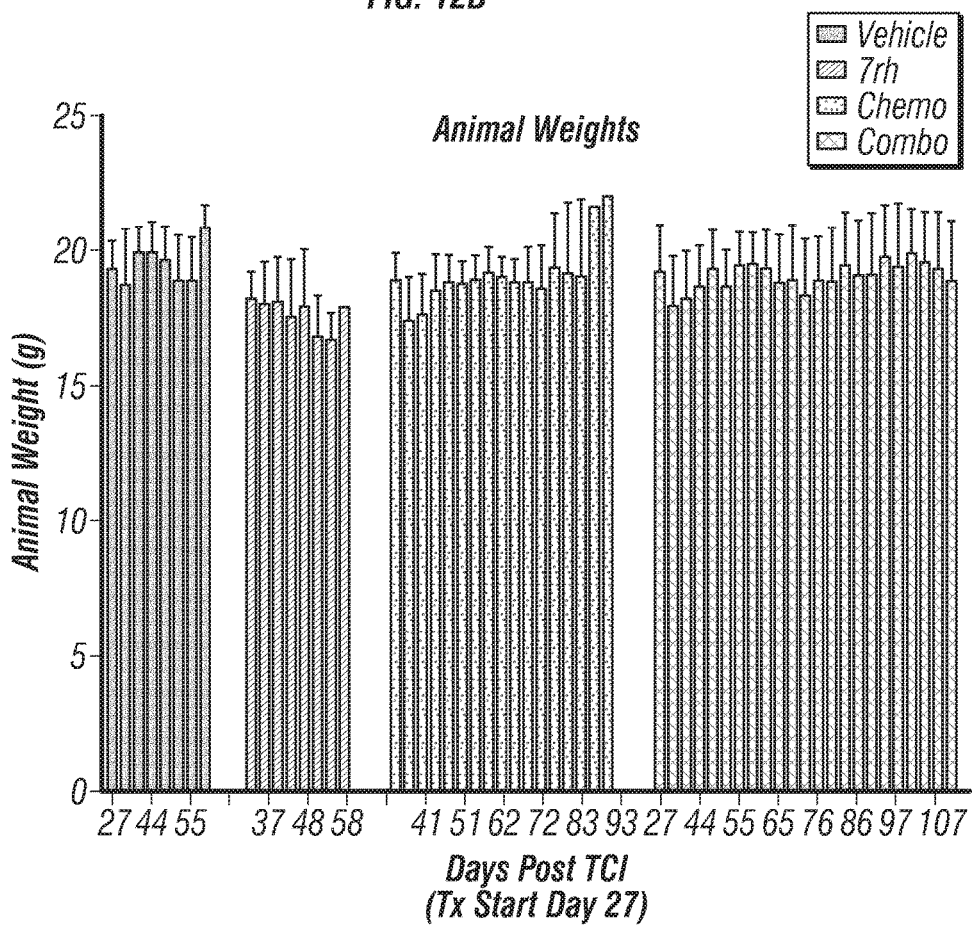
Figure 13G:
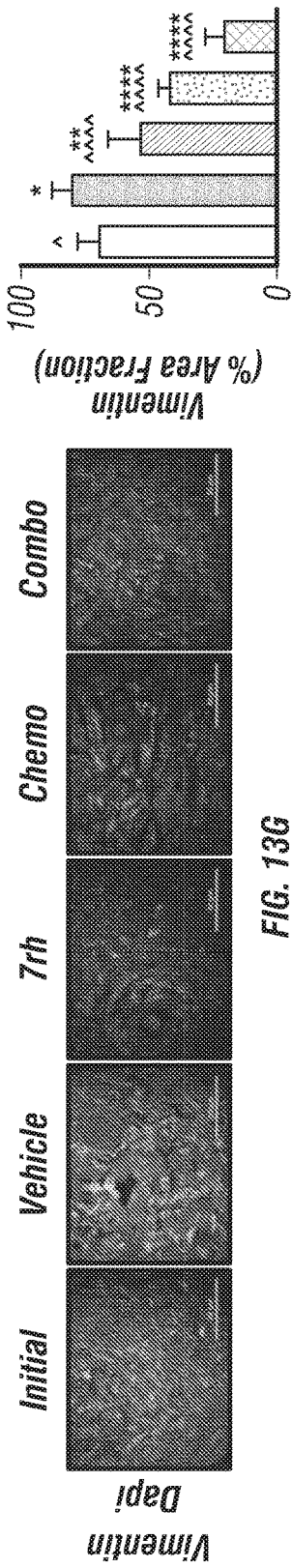
Figure 13H:
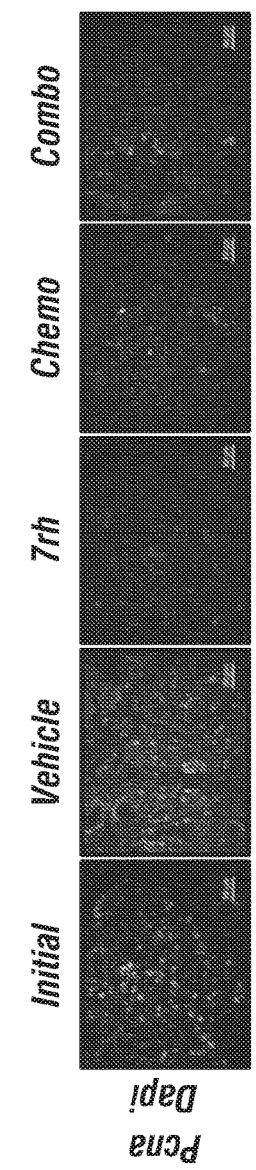
Figure 13I:
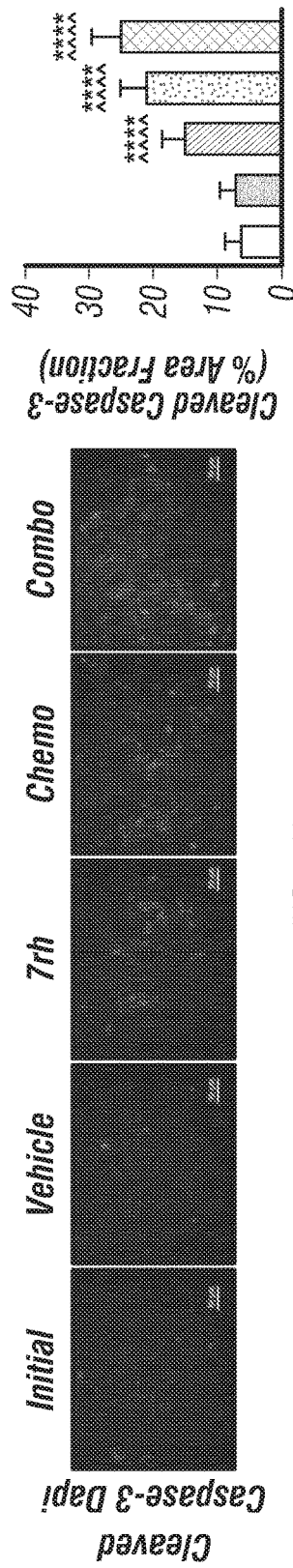
Figure 13J:
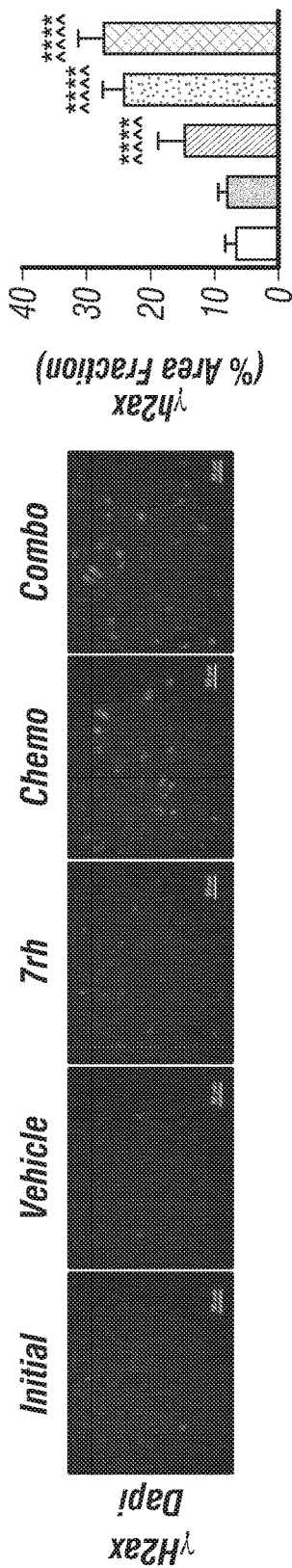

FIGS. 12A-C: 7rh in combination with chemotherapy reduced collagen deposition and AsPC-1 tumor weight. (FIG. 12A) Trichrome analysis of tumor tissue from mice bearing orthotopic AsPC-1 tumors treated with 7rh, chemotherapy or the combination as described in FIG. 5. (FIG. 12B) Pancreas (tumor) weight v day of sacrifice is displayed. (FIG. 12C) Animal weight for each treatment group is displayed.

FIGS. 13A-J: 7rh in combination with chemotherapy reduced DDR1-mediated signaling and tumorigenicity in a GEMM of PDA. (FIG. 13A) Schematic representation of the animal experiment. KPC mice were enrolled in therapy cohorts (n=12/grp): vehicle, 7rh (25 mg/kg, 3×/week via oral gavage), chemotherapy (gemcitabine, 12.5 mg/kg, 2×/week given ip; +nab-paclitaxel, 5 mg/kg, 2×/week given ip), or the combination of 7rh+chemotherapy at 4 months old and survival was determined. Nine untreated animals were sacrificed at 4 months of age to determine average initial tumor burden. (FIGS. 13B-13C) 7rh combined with a chemotherapy enhanced the overall median of survival. (FIG. 13D) Example H&E histology from tissue from each treatment group is shown. (FIGS. 13E-13K) Immunofluorescence analysis of PDA tumors from each group for pDDR1 (FIG. 13E), p-PEAK1 (FIG. 13F), Vimentin (FIG. 13G), PCNA (FIG. 13H), cleaved caspase-3 (FIG. 13I) and γH2AX (FIG. 13J) is shown. DAPI was used as a nuclear counterstain (FIG. 13E-13J). Mean+/−SEM % Area Fraction is graphed. *, $p<0.05$; , $p<0.005$; *, $p<0.0005$; **** $p<0.00005$ v initial group; ^, $p<0.05$; ^^, $p<0.005$; ^^^, $p<0.0005$; ^^^^, $p<0.00005$ v vehicle group, one-way ANOVA with Tukey's MCT. Scale bar, 50 μm.

Figure 14A:
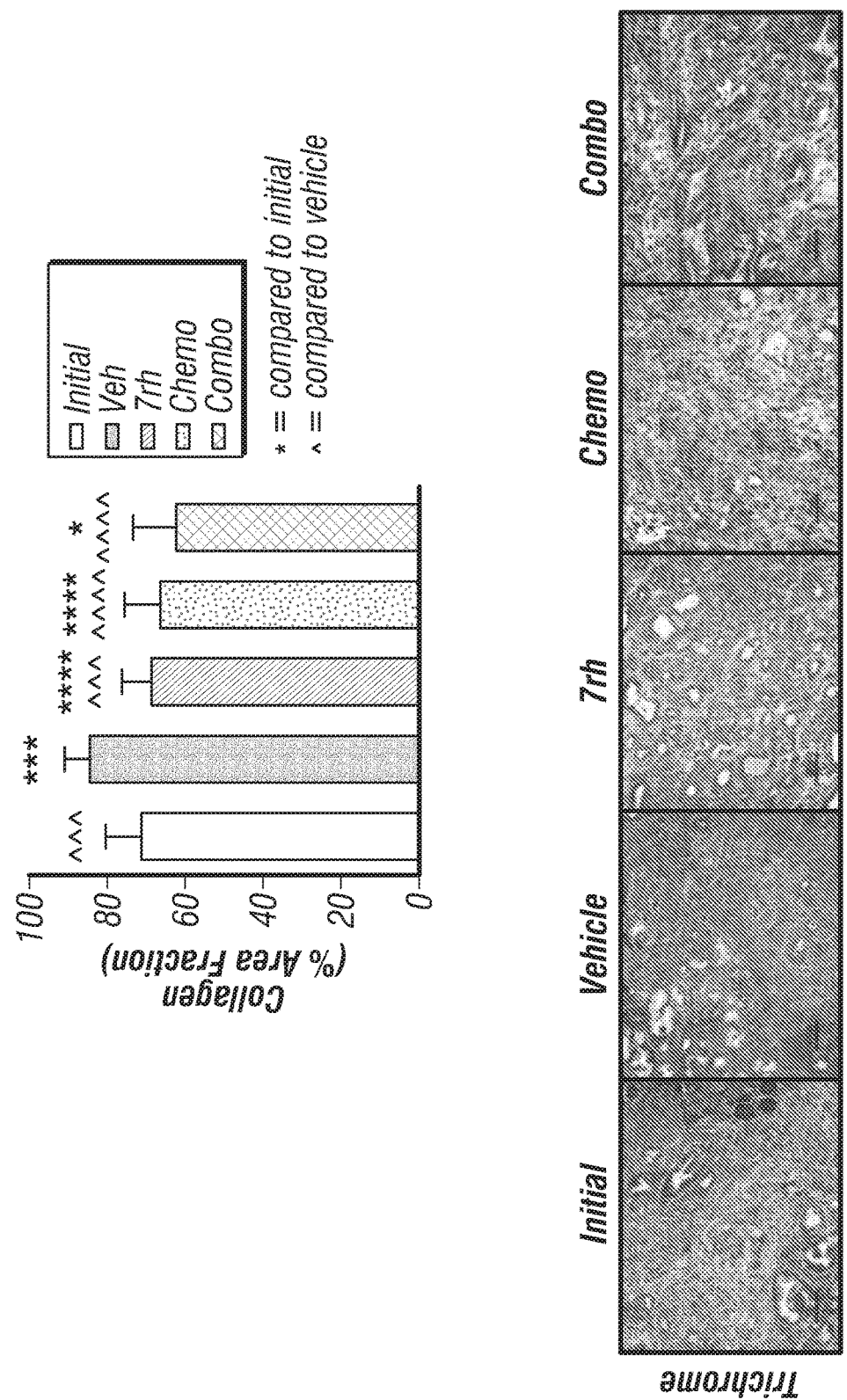
Figure 14B:
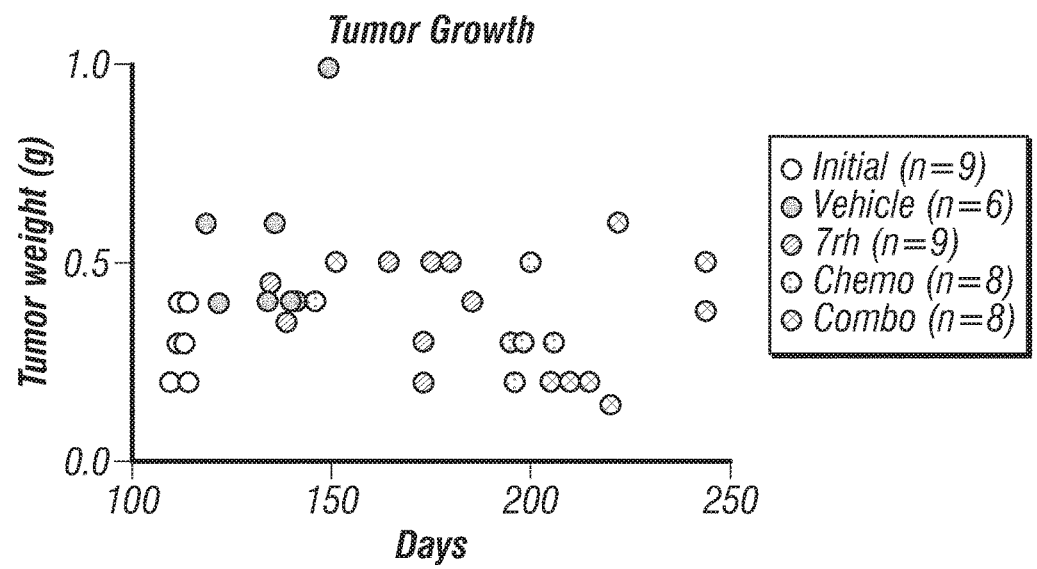
Figure 14C:
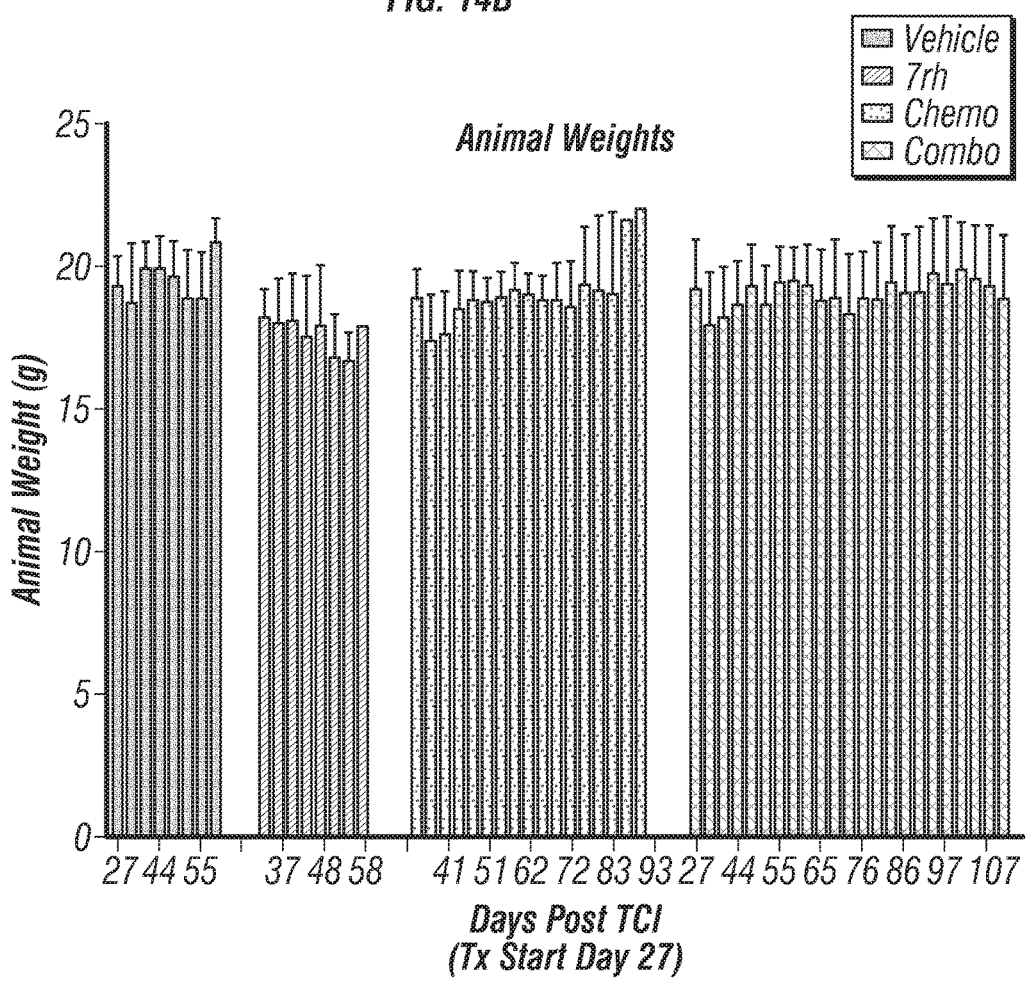

FIGS. 14A-C: 7rh in combination with chemotherapy reduced collagen deposition and KPC tumor weight. (FIG. 14A) Trichrome analysis of tumor tissue from KPC mice treated with 7rh, chemotherapy or the combination as described in FIG. 6. (FIG. 14B) Pancreas (tumor) weight v day of sacrifice is displayed. (FIG. 14C) Animal weight for each treatment group is displayed.

DETAILED DESCRIPTION OF THE PREFERRED EMBODIMENTS

In certain aspects, the present disclosure provides compounds which may be used to inhibit the DDR1 enzyme. Inhibition of the DDR1 enzyme may be used to treat a variety of different inflammatory disease and cancer. As described herein, the compounds may be used in combination with a second chemotherapeutic agent to obtain improved activity or other pharmaceutical parameters. These and other aspects of the disclosure are described in detail below.

1. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "sulfonyl" means —S(O)₂—; "hydroxysulfonyl" means —S(O)₂OH; "sulfonamide" means —S(O)₂NH₂; and "sulfinyl" means —S(O)—.

In the context of chemical formulas, the symbol "—" means a single bond, "=" means a double bond, and "≡" means triple bond. The symbol "----" represents an optional bond, that is either no bond or a single bond. The symbol "⩨" represents a single bond or a double bond. Thus, for example, the formula

includes

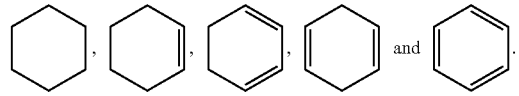

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g., ⊢CH₃ for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⫼⫼⫼" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

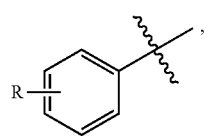

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

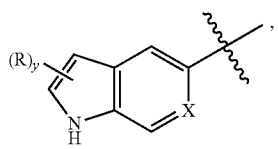

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C \leq 8)}$," or the class "alkene$_{(C \leq 8)}$" is two. Compare with "alkoxy$_{(C \leq 10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "heterocycle" when used to described a compound or a chemical group means that the compound or chemical group is group containing a planar saturated or unsaturated, aromatic or nonaromatic ring of atoms containing one or more N, O, or S atoms. The term "heterocycle" is consistent with either the term "heterocycloalkyl" or the term "heteroaryl" as those terms are described herein.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CHCH═CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH═CH—, —CH═C(CH$_3$)CH$_2$—, —CH═CHCH$_2$—, and —CH$_2$CH═CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH═CHF, —CH═CHCl and —CH═CHBr are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

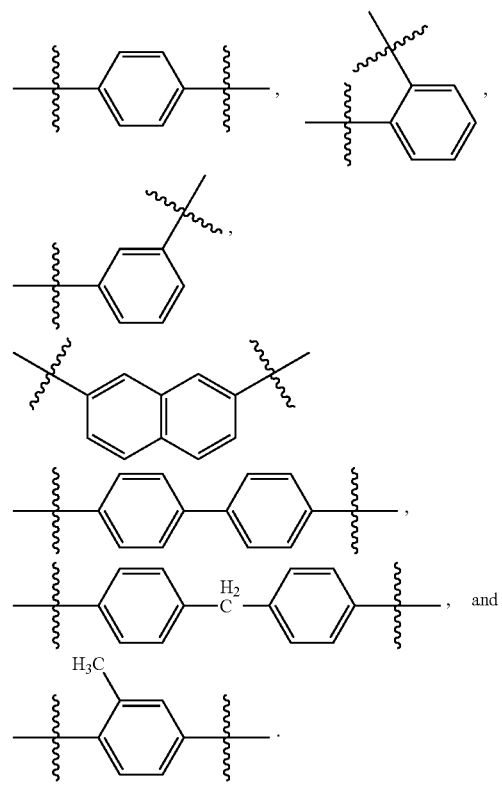

and

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH₃ (acetyl, Ac), —C(O)CH₂CH₃, C(O)CH₂CH₂CH₃, C(O)CH(CH₃)₂, C(O)CH(CH₂)₂, C(O)C₆H₅, C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), —OC(CH₃)₃ (tert-butoxy), —OCH(CH₂)₂, —O-cyclopentyl, and —O-cyclohexyl. The terms "cycloalkoxy", "alkenyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂ and —N(CH₃)(CH₂CH₃). The terms "cycloalkylamino", "alkenylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, aryl, aralkyl, heteroaryl, heterocycloalkyl, and alkoxy, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —NHC(O)OCH₃ and —NHC(O)NHCH₃ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, "essentially free," in terms of a specified component, means that the specified component is only present as a contaminant or in trace amounts. Thus, the total amount of the specified component resulting from any unintended contamination of a composition may be below 5%, below 1%, or below 0.1%. In some embodiments, none of the specified component can be detected in the composition using standard analytical methods.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Additional examples of pharmaceutically acceptable salts are from inorganic acids that include hydrochloric acid, hydrobromic acid, sulfuric acid, sulfamic acid, phosphoric acid, nitric acid, and from organic acids that include acetic acid, propionic acid, succinic acid, glycolic acid, stearic acid, lactic acid, malic acid, tartaric acid, lemon acid, ascorbic acid, bashing acid, maleic acid, hydroxy-maleic acid, phenylacetic acid, glutamic acid, benzoic acid, salicylic acid, sulfanilic acid, 2-acetoxy-benzoic acid, p-toluenesulfonic acid, methanesulfonic acid, ethane disulfonic, oxalic acid, hydroxyethyl sulfonic acid, trifluoroacetic acid etc. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. In some embodiments, the examples in the disclosure are the protonated salts of amines. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002) and Berg et al. "Pharmaceutical Salts," *J. Pharm. Sci.* 1977, 66: 1-19.

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2', where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

2. Compounds of the Disclosure

The compounds provided by the present disclosure are shown, for example, above in the Summary section and in the claims below. They may be made using the methods outlined in the Examples section and Section A below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference. In some aspects, the compounds in the present disclosure may be present in their free base form or as protonated amine salts.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

A. Synthesis

The compounds of the present disclosure can be prepared by using the following method besides the method which is widely validated in the experimental procedures or has been published in articles. Therefore the synthetic scheme below only outlines the examples and does not limit the compounds or any specific substituent.

As shown in the schemes A and B, compounds in formula I may be synthesized through five steps by using methyl 4-(1-aminopropan-2-yl)benzoate as the starting material, or through six steps by using 2-phenylpropan-1-amine as the starting material.

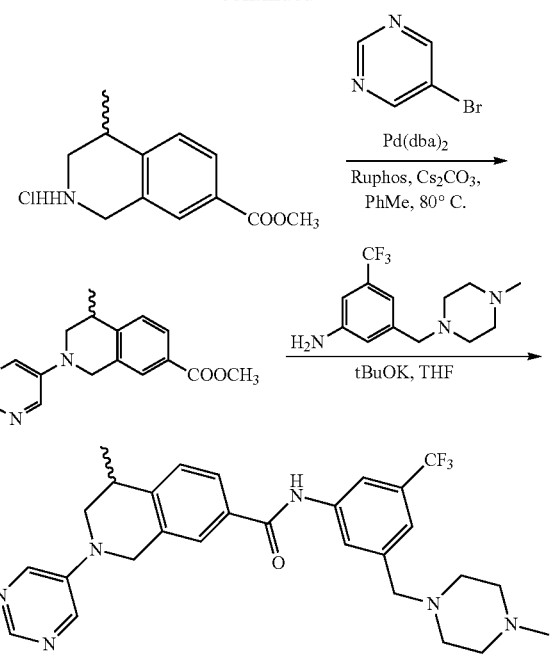

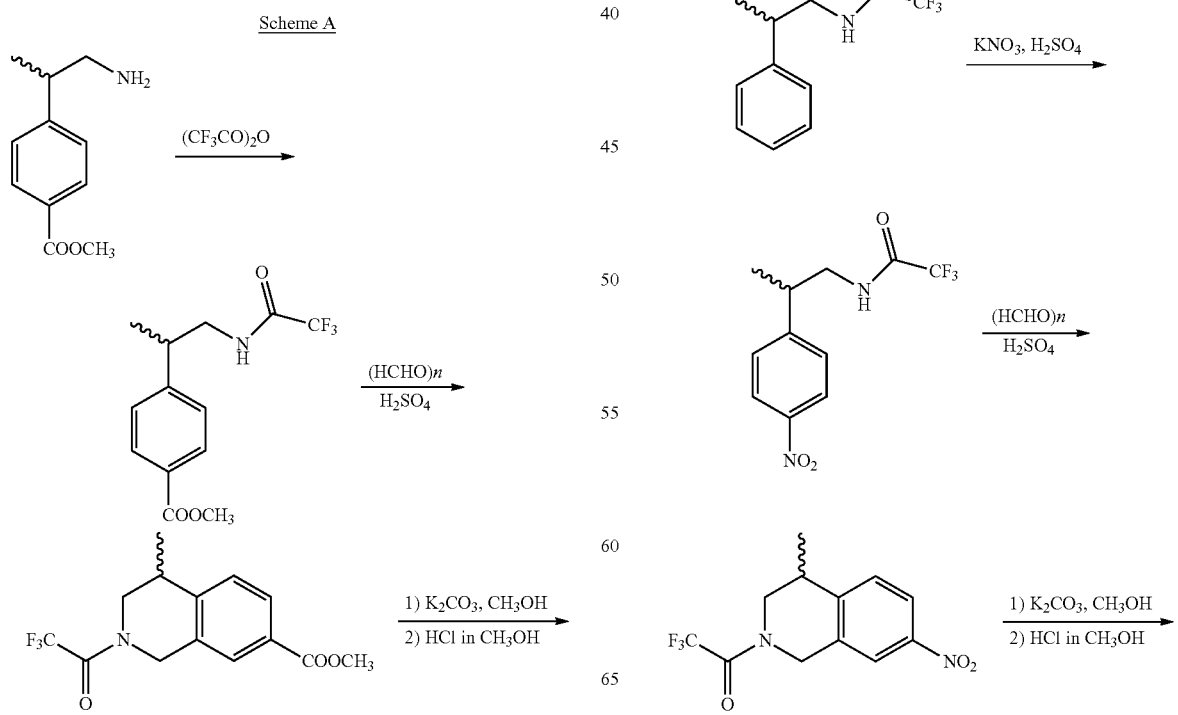

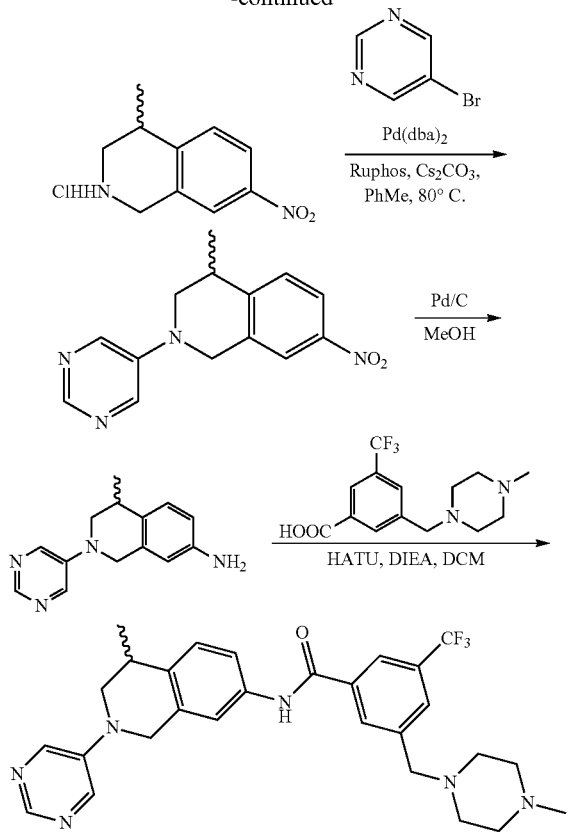

B. Metabolites—Prodrugs

The metabolites of the compounds and their pharmaceutical salts in the present disclosure, and prodrugs that are converted to the compounds and their pharmaceutical salts in the present disclosure are comprised in the claims of the present application.

Therapeutic Methods

In one embodiment, the present disclosure provides methods of using compounds in formula (I) and their pharmaceutical acceptable salts for preventing and treating, e.g., inflammation, liver fibrosis, kidney fibrosis, lung fibrosis, skin scar, atherosclerosis and cancer. Various aspects of the therapies are provided below.

3. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render drugs stable and allow for uptake by target cells. Buffers may be employed when drugs are introduced into a patient. Aqueous compositions of the present disclosure comprise an effective amount of the drug to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the drugs of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration, the compounds of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4. Inflammatory Disease States and Conditions

Inflammation underlies many, if not all, disease states. There a variety of inflammatory signaling pathways, but inflammation is always characterized by a protective response that involves immune cells, blood vessels, and molecular mediators. The purpose of inflammation is to eliminate the initial cause of cell injury, clear out necrotic cells and tissues damaged from the original insult and the inflammatory process, and to initiate tissue repair. The classical signs of acute inflammation are pain, heat, redness, swelling, and loss of function. Inflammation is a generic response, and therefore it is considered as a mechanism of innate immunity, as compared to adaptive immunity, which is specific for each pathogen.

Inflammation can be classified as either acute or chronic. Acute inflammation is the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

Inflammation is not a synonym for infection. Infection describes the interaction between the action of microbial invasion and the reaction of the body's inflammatory defensive response—the two components are considered together when discussing an infection, and the word is used to imply a microbial invasive cause for the observed inflammatory reaction. Inflammation on the other hand describes purely the body's immunovascular response, whatever the cause may be. But because of how often the two are correlated, words ending in the suffix -itis (which refers to inflammation) are sometimes informally described as referring to infection. Some examples of inflammatory disease states are discussed below.

A. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystaloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, but drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a β-lactam antibiotic (such as ampicillin) with an aminoglycoside such as gentamicin.

B. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present disclosure provides to treatment of trauma, including both pre-treatment (in the case of a medical procedure) and treatment after trauma injury as occurred.

Surgery.

Surgery uses operative manual and instrumental techniques on a patient to investigate and/or treat a pathological condition such as disease or injury, to help improve bodily function or appearance, or sometimes for some other reason. The present disclosure can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage.

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

C. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

D. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation ($\geq 2$ weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

E. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

F. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

G. Autoimmune/Inflammatory Disease

The present disclosure contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

H. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present disclosure seeks to reduce this toxicity using the pharmaceutical compositions of the present disclosure, thereby reducing or alleviating discomfort on the part of the patient, as well as permitting higher doses of the therapy.

I. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. This formula dictates that the amount of Lactated Ringer's solution to deliver in the first twenty four hours after time of injury is:

$$\text{fluid} = 4cc \times \% \text{ TBSA} \times \text{weight in kg}$$

% TBSA excludes any first degree burn

Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

J. Cancer

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Studies have estimated that nearly 15% of worldwide cancer is associated with microbial infection. Organisms such as human papilloma virus (HPV), hepatitis B and C virus, HIV, and *Helicobacter pylori* all have been linked to cancer. In other cases, environmental conditions causing chronic irritation and subsequent inflammation can also predispose to cancer, including cigarette smoke, asbestos and silica.

In the case of some types of viral infection, virally-encoded genes can contribute to cellular transformation. An example is the HPV oncoproteins E6 and E7. However, other microbes associated with cancer do not operate in this fashion as they are not transforming. For example, certain strains of *H. pylori* contain factors that affect host cell signaling but do not contain oncogenes. Interestingly, it has been observed that *H. pylori* induces MUC1.

Other ways in which chronic inflammatory states can lead to genomic lesions and tumor initiation are chemical. For example, host cells fight microbial infection by the production of free radicals. In addition to their anti-microbial effects, these molecules lead to oxidative damage and nitration of DNA bases which increases the risk of DNA mutations even in host cells.

Yet another path to cellular dysregulation may result from the cell death that occurs in infection or other inflammatory insult. Lost cells must be repopulated by the expansion of other cells, sometimes undifferentiated precursor cells such as tissue stem cells. Not surprisingly, many inflammatory pathways function to mediate survival and proliferation. Thus, in attempting to mediating tissue repair, the inflammatory response may unwittingly provide excessive survival and proliferative signals to cells, thus leading to tumorigenesis.

Because of the link between cancer and inflammation, the ability of the compounds of the present disclosure to reduce inflammatory signalling pathways can be exploited in a pre-cancer or cancer risk situation to prevent or delay the onset of dysplastic growth.

K. Fibrosis

Fibrosis is the formation of excess fibrous connective tissue in an organ or tissue in a reparative or reactive process. This can be a reactive, benign, or pathological state. In response to injury this is called scarring and if fibrosis arises from a single cell line this is called a fibroma. Physiologically this acts to deposit connective tissue, which can obliterate the architecture and function of the underlying organ or tissue. Fibrosis can be used to describe the pathological state of excess deposition of fibrous tissue, as well as the process of connective tissue deposition in healing.

Fibrosis is similar to the process of scarring, in that both involve stimulated cells laying down connective tissue, including collagen and glycosaminoglycans Immune cells called macrophages, as well as any damaged tissue between surfaces called interstitium, release TGF beta. This can be because of numerous reasons, including inflammation of the nearby tissue, or a generalised inflammatory state, with increased circulating mediators. TGF beta stimulates the proliferation and activation of fibroblasts, which deposit connective tissue.

Fibrosis can occur in many tissues within the body, typically as a result of inflammation or damage, and examples include lung, including pulmonary fibrosis (idiopathic pulmonary fibrosis and cystic fibrosis), liver (cirrhosis), heart (endomyocardial fibrosis, old myocardial infarction, atrial fibrosis), and others (mediastinal fibrosis, myelofibrosis, retroperitoneal fibrosis, progressive massive fibrosis, nephrogenic systemic fibrosis, Crohn's disease, keloid, scleroderma/systemic sclerosis, arthrofibrosis, Peyronie's disease, Dupuytren's contracture, adhesive capsulitis).

5. Treatment Methods

Compound of the present disclosure are generally useful as anti-inflammatories and can be used for the treatment of inflammatory conditions. They can be administered to mammalian subjects (e.g., human patients) alone or in conjunction with other drugs that modulate inflammation (see below). The compounds can also be administered to subjects that are genetically and/or due to, for example, physiological and/or environmental factors, susceptible to inflammation, e.g., subjects with a family history of inflammatory disease, or subjects with chronic inflammation or subject to chronic stress.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the compounds in a suitable delivery vehicle (e.g., polymeric microparticles or implantable devices) may increase the efficiency of delivery, particularly for oral delivery.

6. Combination Therapy

Compounds of Formula (I) may be used in combination with other drugs that are known to be useful in the treatment or amelioration of the diseases or similar diseases. In the combination administration, such other drugs may be administered, by a route administration and in an amount commonly used, and contemporaneously or sequentially with a compound of Formula. When a compound of Formula (I) is used contemporaneously with one or more other drugs, a pharmaceutical composition containing one or more other known drugs and the compound of Formula (I) is preferred.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with an agent according to the present disclosure and at least one other agent. These compositions would be provided in a combined amount effective to kill or inhibit proliferation of the cell. This process may involve contacting the cells with the agent according to the present disclosure and the other treatment at the same time. This may be achieved by contacting the cell with a single composition or pharmacological formulation that includes both agents, or by contacting the cell with two distinct compositions or formulations, at the same time, wherein one composition includes the agent according to the present disclosure and the other includes the other agent.

Alternatively, the agent according to the present disclosure may precede or follow the other agent treatment by intervals ranging from minutes to weeks. In embodiments where the other agent and the agent according to the present disclosure are applied separately to the cell, one would generally ensure that a significant period of time did not expire between the time of each delivery, such that the agent according to the present disclosure and the other therapy would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the agent according to the present disclosure or the other therapy will be desired. Various combinations may be employed, where an agent according to the present disclosure therapy is "A" and the other therapy is "B", as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are contemplated. Again, to achieve cell killing, both agents are delivered to a cell in a combined amount effective to kill the cell.

Drugs or active ingredients used in combination with compounds of Formula (I) comprises but are not limited to: estrogen receptor modulator, androgen receptor modulator, retinoid receptor modulator, cell toxin/cell inhibitor, antiproliferative agents, protein transferase inhibitors, HMG-CoA reductase inhibitors, HIV protein kinase inhibitors, reverse transcriptase inhibitors, angiogenesis inhibitors, cell proliferation and survival signaling inhibitors, interference with the cell cycle checkpoint drugs and apoptosis inducing agent, cytotoxic drugs, protein tyrosine inhibitor, EGFR, VEGFR inhibitors, inhibitors of serine/threonine protein inhibitors, inhibitors of Bcr-Abl, c-Kit inhibitor, Met inhibitors, inhibitors of Raf, MEK inhibitor, MMP inhibitors, inhibitors of topoisomerase, histidine deacetylase inhibitors, proteasome inhibitors, inhibitors of CDK, Bcl-2 family protein inhibitor, MDM2 family protein inhibitors, inhibitors of IAP family proteins, inhibitor of STAT family proteins, PI3K, AKT inhibitors, inhibitors of integrin blockade, IFN-α, interleukin-12, COX-2 inhibitor, p53, p53 activator inhibitor, VEGF antibody, EGF antibody, etc.

In one embodiment, drugs or active ingredients used in combination with compounds of Formula (I) comprises but are not limited to: Aldesleukin, Alendronate, interferon, Alitretinoin, allopurinol, allopurinol sodium, palonosetron hydrochloride, Hemel, amino glutethimide, amifostine, amrubicin, Ann acridine, anastrozole, dolasetron, Aranesp, arglabin, arsenic trioxide, Aromasin, 5—N cytidine, azathioprine, BCG or BCG, Bestatin hydrochloride, betamethasone acetate, betamethasone sodium phosphate, Bexarotene, bleomycin sulfate, broxuridine, bortezomib, busulfan, calcitonin, Alemtuzumab Campath, capecitabine, carboplatin, Casodex, cefesone, Seamus IL, DNR, chlorambucil, cisplatin, cladribine, cladribine, chloride phosphoric acid, Cytarabine, cyclophosphamide, Dacarbazine, Actinomycin D, DNX, dexamethasone, dexamethasone phosphate, estradiol valerate, cefdinir interleukin 2, Methylprednisolone acetate, deslorelin, dexrazoxane, diethylstilbestrol, Diflucan, docetaxel, doxorubicin, doxifluridine, dronabinol, chin-166-chitosan complexes, eligard, rasburicase, epirubicin hydrochloride, aprepitant, epirubicin, alfa-epoetin, erythropoietin, Eptaplatin, levamisole, estradiol formulation, 17-β-estradiol, estramustine phosphate sodium, ethinylestradiol, Amifostine, hydroxyl phosphate, Etopophos, etoposide, Fadrozole, tamoxifen, filgrastim, finasteride, floxuridine, fluconazole, fludarabine, 5-fluorine BrdU a phosphate, 5-fluorouracil, fluoxymesterone, flutamide, formestane, Cytarabine hydrochloride, Fotemustine, fulvestrant, immunoglobulin, gemcitabine, gemtuzumab ozogamicin, imatinib mesylate, carmustine capsules, goserelin, hydrocortisone, erythro-hydroxy nonyl adenine, hydroxyurea, Ibritumomab Tiuxetan. Idarubicin, ifosfamide, interferon α, IFN-α2, interferon α-2A, interferon α-2B, interferon α-n1, IFN α-n3, interferon β, interferon γ-1a, IL-2, intron A, Iressa, Irinotecan, Kytril, mushroom polysaccharide sulfate, letrozole, leucovorin, leuprolide, leuprorelin acetate, Levamisole, levorotation folinic acid calcium salt, levothyroxine sodium, levothyroxine sodium, lomustine, lonidamine, dronabinol, nitrogen mustard, Mecobalamin, medroxyprogesterone acetate, megestrol acetate, melphalan, esterified estrogens, 6-Mercaptopurine, mesna, methotrexate, aminolevulinic acid methyl ester, miltefosine, minocycline, mitomycin C, mitotane, mitoxantrone anthraquinone, Trilostane, citric acid adriamycin liposome, Nedaplatin, Pegfilgrastim, oprelvekin, neupogen, nilutamide, tamoxifen, NSC-631570, recombinant human interleukin 1-β, octreotide, Ondansetron hydrochloride, hydroprednisone oral solution, oxaliplatin, paclitaxel, prednisone, L-asparaginase enzyme sodium phosphate preparation, Pegasys, pentostatin, Picibanil, pilocarpine hydrochloride, adjoin THP, mithramycin, porfimer sodium, prednimustine, Prednisolone Steaglate, prednisolone, Premarin, C kappa umbilical, recombinant human erythropoietin, raltitrexed, Libby, etidronate rhenium-186, rituximab, Redoxon-A, Romo peptide, pilocarpine hydrochloride tablets, octreotide, Sargramostim, semustine, Schizophyllan, sobuzoxane, Methylprednisolone, Paphos acid, stem cell therapy, streptozocin, strontium chloride-89, levothyroxine sodium, tamoxifen, tamsulosin, TNF-alfa, tastolactone, docetaxel, teceleukin, temozolomide, teniposide, propionic acid testosterone, testosterone propionate, thioguanine, thiotepa, thyroid stimulating hormone, Tiludronic acid, topotecan, toremifene, tositumomab, trastuzumab, Treosulfan, Victoria A acid, methotrexate tablets, three methyl melamine, trimetrexate, triptorelin, double hydroxy acetic acid Naphthalene of triptorelin, UFT, uridine, valrubicin, vesnarinone, alkali, vincristine, Vindesine Vinorelbine, virulizin, dextral razoxane, Zinostatin ester, ondansetron, paclitaxel, acolbifene, Interferon r-1β, affinitak, aminopterin, Arzoxifene, Asoprisnil, atamestane, atrasentan, BAY 43-9006, Avastin, CCI-779, CDC-501, Celebrex, cetuximab, crisnatol, cyproterone acetate, decitabine, DN-101, Doxorubicin-MTC, dSLIM, dutasteride, edotecarin, eflornithine, Exatecan, Fenretinide, histamine hydrochloride, holmium-166 DOTMP, ibandronate, IFN-γ, intron-PEG, ixabepilone, intron keyhole shaped hemocyanin, L-651582, Lanreotide, lasofoxifene, Libra, lonafamib, Miproxifene, MS-209, liposome MTP-PE, MX-6, Nafarelin, Nemorubicin, Neovastat, Nolatrexed, Aolimosen, oncoTCS, osidem, paclitaxel poly glutamic acid ester, pamidronate disodium injection, PN-401, QS-21, R-1549, raloxifene, ranpirnase, 13-cis-Victoria A acid, satraplatin, seocalcitol, T-138067, Tarceva, DHA-PTX, thymosin α1, Pirazofurin, tipifarnib, tirapazamine, TLK-286, toremifene, trans MID-lo7R, valspodar, vapreotide, vatalanib, verteporfin, Vinflunine, Z-100 and Zoledronic acid or their combination.

7. Examples

The following examples are included to demonstrate certain embodiments of the disclosure. It should be appreciated by those of skill in the art that the techniques disclosed in the examples which follow represent techniques discovered by the inventor to function well in the practice of the disclosure, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the disclosure.

Example 1—4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2095)

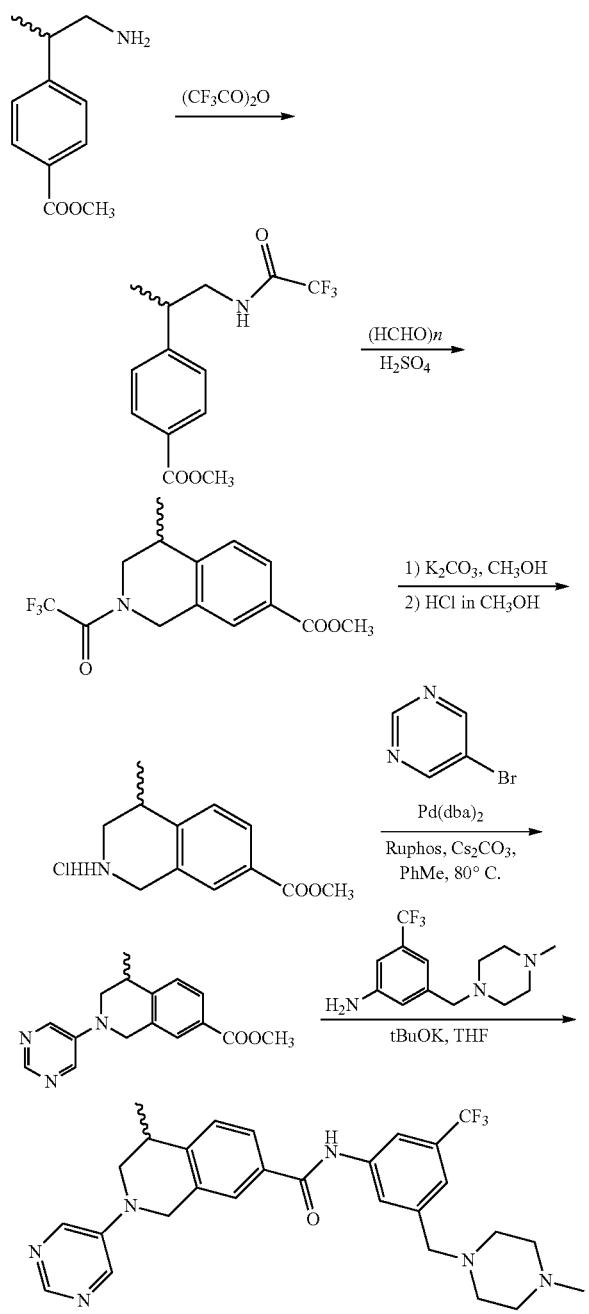

Step 1. Methyl 4-(1-(2,2,2-trifluoroacetamido)propan-2-yl)benzoate

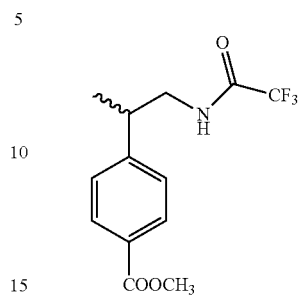

Methyl 4-(1-aminopropan-2-yl)benzoate (10.0 g, 51.7 mmol) was added portionwise to the well stirred trifluoroacetic anhydride (50 ml). The reaction mixture was stirred at RT for 3 hrs. On completion of the reaction, the reaction mixture was poured into 100 ml of ice water, and stirred for 30 mins. The resulting solid was filtered, washed with water, and dried under vacuum to give the pure compound (9.0 g, 60% yield).

$^1$H NMR (400 MHz, CDCl$_3$), δ 8.01 (d, J=7.6 Hz, 2H), 7.27 (d, J=7.6 Hz, 2H), 6.14 (br s, 1H), 3.91 (s, 1H), 3.72-3.65 (m, 1H), 3.43-3.36 (m, 1H), 3.12-3.07 (m, 1H), 1.33 (d, J=6 Hz, 3H). MS (ESI), m/z: 290 (M$^+$+H$^+$).

Step 2. Methyl 4-methyl-2-(2,2,2-trifluoroacetyl)-1,2,3,4-tetrahydroisoquinoline-7-carboxylate

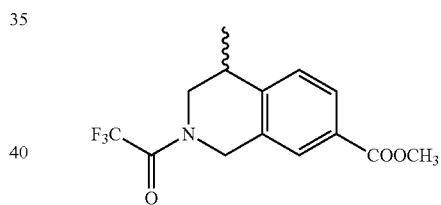

Methyl 4-(1-(2, 2, 2-trifluoroacetamido)propan-2-yl)benzoate (9.0 g, 31.1 mmol) was stirred at RT with (HCHO)$_n$ (4.5 g) and con.H$_2$SO$_4$ for 5 hrs. The clear solution was added to cold water and extracted with ethyl acetate. The organic layer was washed with saturated Na$_2$CO$_3$, water, and dried over anhydrous Na$_2$SO$_4$. The filtrate was concentrated under vacuum to give the title compound (8.4 g, 89% yield). MS (ESI), m/z: 302 (M$^+$+H$^+$).

Step 3. Methyl 4-methyl-1, 2, 3, 4-tetrahydroisoquinoline-7-carboxylate hydrochloride

Methyl 4-methyl-2-(2, 2, 2-trifluoroacetyl)-1, 2, 3, 4-tetrahydroisoquinoline-7-carboxylate (8.4 g, 27.7 mmol) was added to K₂CO₃ (5.7 g, 41.5 mmol) in methanol and water (2:1), and stirred at RT for 3 hrs. Methanol was removed from the reaction mixture and water was added, extracted with ethyl acetate, followed by washing with water. The organic layer was dried over anhydrous Na₂SO₄, and evaporated under reduced pressure to get the compound as colorless oil. Then the oil was diluted with methanol, and HCl solution in methanol was added dropwise. The mixture was stirred for 1 hr, and the white solid was collected, and dried under reduced pressure to give the title compound (6.4 g, 95% yield). ¹H NMR (400 MHz, DMSO-d₆), δ 9.83 (br s, 1H), 9.67 (br s, 1H), 7.87-7.85 (m, 2H), 7.52 (d, J=8.0 Hz, 1H), 4.32 (s, 2H), 3.85 (s, 3H), 3.51-3.41 (m, 1H), 3.31-3.26 (m, 1H), 3.05-2.98 (m, 1H), 1.34 (d, J=6.8 Hz, 3H). MS (ESI), m/z: 242 (M⁺+H⁺).

Step 4. Methyl 4-methyl-2-(pyrimidin-5-yl)-1,2,3,4-tetrahydroisoquinoline-7-carboxylate

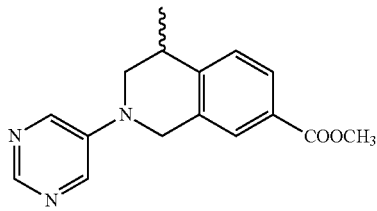 [SMILES: COC(=O)c1ccc2c(c1)CN(c1cncnc1)CC2C]

An oven-dried test tube, which was equipped with a magnetic stir bar and fitted with a teflon septum, was charged with the Pd(dba)₂ (10 mmol %), Ruphos (20 mmol %), CsCO₃ (3.3 g, 10.3 mmol), methyl 4-methyl-1,2,3,4-tetrahydroisoquinoline-7-carboxylate hydrochloride (1.0 g, 4.1 mmol), and 5-bromopyrimidine (782 mg, 4.9 mmol). The vessel was evacuated and backfilled with argon and then toluene (20 mL) was added via syringe. The solution was heated to 80° C. overnight, and then cooled to room temperature. The reaction mixture was filtered through a pad of Celite and concentrated under vacuum, and then purified by flash column to yield the title compound (1.0 g, 89% yield). ¹H NMR (400 MHz, CDCl₃), δ 8.70 (s, 1H), 8.48 (s, 2H), 7.93 (d, J=8.0 Hz, 1H), 7.89 (s, 1H), 7.35 (d, J=8.0 Hz, 1H), 4.59 (d, J=15.2 Hz, 1H), 4.48 (d, J=15.2 Hz, 1H), 3.92 (s, 3H), 3.63-3.60 (m, 1H), 3.45-3.41 (m, 1H), 3.23-3.22 (m, 1H), 1.42 (d, J=7.2 Hz, 3H). MS (ESI), m/z: 284 (M⁺+H⁺).

Step 5. 4-methyl-N-(3-((4-methylpiperazin-1-yl)methyl)-5-(trifluoromethyl)phenyl)-2-(pyramidin-5-yl)-1, 2, 3, 4-tetrahydroisoquinoline-7-carboxamide

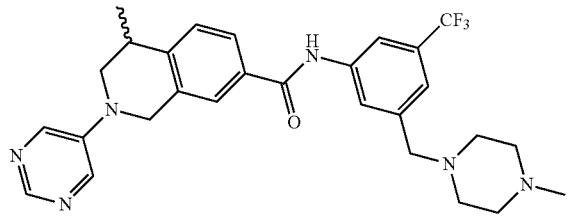 [SMILES: CC1CN(c2cncnc2)Cc2cc(C(=O)Nc3cc(CN4CCN(C)CC4)cc(C(F)(F)F)c3)ccc21]

To a solution of methyl 4-methyl-2-(pyrimidin-5-yl)-1,2, 3,4-tetrahydroisoquinoline-7-carboxylate (1 g, 3.5 mmol) and 3-((4-methylpiperazin-1-yl)methyl)-5-(trifluoromethyl) aniline (909 mg, 3.3 mmol) in anhydrous THF (20.0 mL) was added potassiumtert-butoxide (1.1 g, 9.9 mmol) portionwise at −20° C. Then the reaction mixture was slowly warmed to room temperature and stirred for 1.0 h. After the reaction was finished by TLC, the mixture was poured into ice water with stirring and extracted with ethyl acetate. The organic layer was washed with brine and dried over anhydrous Na₂SO₄. The filtrate was concentrated under vacuum. The resulting residue was purified by silica gel column to give the desired product (1.4 g, 80% yield). ¹H NMR (400 MHz, DMSO-d₆) δ 10.50 (s, 1H), 8.64-8.51 (m, 3H), 8.19 (s, 1H), 8.00 (s, 1H), 7.92-7.79 (m, 2H), 7.47 (d, J=7.6 Hz, 1H), 7.34 (s, 1H), 4.65 (d, J=16.0 Hz, 1H), 4.53 (d, J=16.0 Hz, 1H), 3.67-3.64 (m, 1H), 3.53 (s, 2H), 3.49-3.47 (m, 1H), 3.24-3.11 (m, 1H), 2.39 (br s, 4H), 2.34 (br s, 4H), 2.15 (s, 3H), 1.34 (d, J=5.2 Hz, 3H). MS (ESI), m/z: 525 (M⁺+H⁺).

Example 2—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide (D2217)

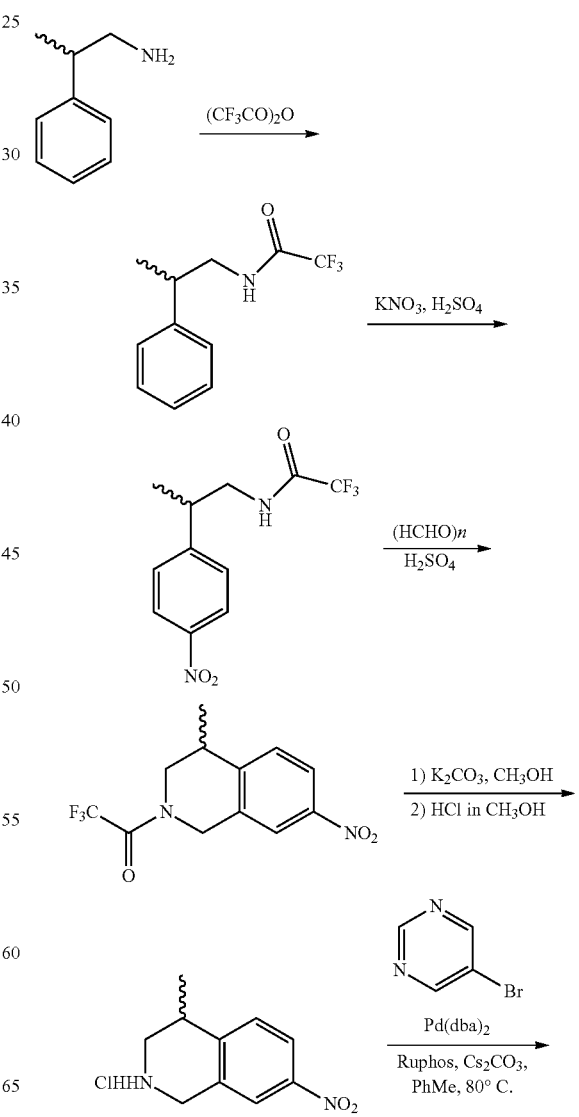

-continued

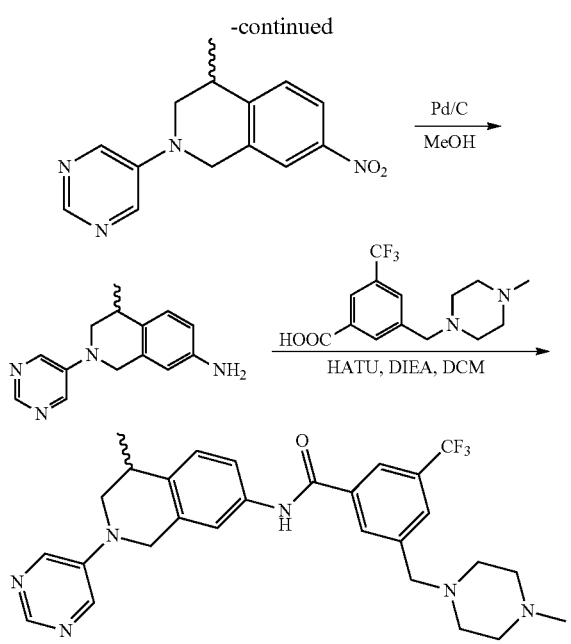

Step 1. 2, 2, 2-trifluoro-N-(2-phenylpropyl)acetamide

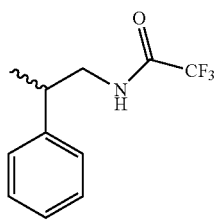 [SMILES: CC(CNC(=O)C(F)(F)F)c1ccccc1]

2-phenylpropan-1-amine (10.0 g, 74.0 mmol) was added portionwise to the well stirred trifluoroacetic anhydride (50 ml). The reaction mixture was stirred at RT for 3 hrs. On completion of the reaction, the reaction mixture was poured into 100 ml of ice water, and stirred for 30 mins. The resulting solid was filtered, washed with water, and dried under vacuum to give the pure compound (12.0 g, 70% yield). $^1$H NMR (400 MHz, DMSO-$d_6$), δ 9.43 (s, 1H), 7.30 (t, J=7.2 Hz, 2H), 7.23-7.19 (m, 3H), 3.39-3.27 (m, 2H), 3.04-2.96 (m, 1H), 1.19 (d, J=6.8 Hz, 3H). MS (ESI), m/z: 232 (M$^+$+H$^+$).

Step 2. 2, 2, 2-trifluoro-N-(2-(4-nitrophenyl)propyl)acetamide

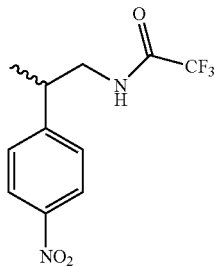 [SMILES: CC(CNC(=O)C(F)(F)F)c1ccc([N+](=O)[O-])cc1]

2,2,2-trifluoro-N-(2-phenylpropyl)acetamide (12 g, 51.9 mmol) was dissolved in con.H2SO4 at 0° C., and then potassium nitrate (5.8 g, 57.0 mmol) was added portionwise. The mixture was stirred at 0° C. for 1 hr. After the reaction was completed, the mixture was poured into ice water. The resulting solid was filtered, washed with water, and dried under vacuum to give the pure compound (12.6 g, 88% yield). MS (ESI), m/z: 277 (M$^+$+H$^+$).

Step 3. 2, 2, 2-trifluoro-1-(4-methyl-7-nitro-3,4-dihydroisoquinolin-2(1H)-yl)ethanone

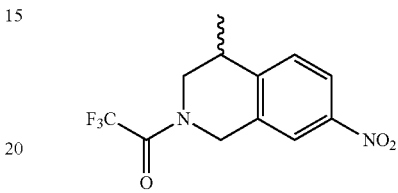

2, 2, 2-trifluoro-N-(2-(4-nitrophenyl)propyl)acetamide (12.6 g, 45.7 mmol) was stirred at RT with (HCHO)n (6.7 g) and con.H2SO4 for 5 hrs. The clear solution was added to cold water and extracted with ethyl acetate. The organic layer was washed with saturated Na$_2$CO$_3$, water, and dried over anhydrous Na$_2$SO$_4$. The filtrate was concentrated under vacuum to give the title compound (6.6 g, 50% yield). $^1$H NMR (400 MHz, DMSO-$d_6$), δ 8.28-8.22 (m, 1H), 8.10-8.06 (m, 1H), 7.57 (d, J=8.4 Hz, 1H) 5.03-4.97 (m, 1H), 4.88-4.72 (m, 1H), 3.86-3.76 (m, 1H), 3.70-3.66 (m, 1H), 3.23-3.22 (m, 1H), 1.24-1.20 (m, 3H). MS (ESI), m/z: 289 (M$^+$+H$^+$).

Step 4. 4-methyl-7-nitro-1,2,3,4-tetrahydroisoquinoline hydrochloride

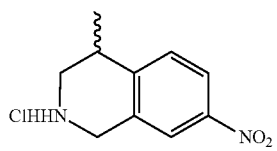

2, 2, 2-trifluoro-1-(4-methyl-7-nitro-3,4-dihydroisoquinolin-2(1H)-yl)ethanone (6.6 g, 22.9 mmol) was added to K$_2$CO$_3$ (4.7 g, 34.4 mmol) in methanol and water (2:1), and stirred at RT for 3 hrs. Methanol was removed from the reaction mixture and water was added, extracted with ethyl acetate, followed by washing with water. The organic layer was dried over anhydrous Na$_2$SO$_4$, and evaporated under reduced pressure to get the compound as colorless oil. Then the oil was diluted with methanol, and HCl solution in methanol was added dropwise. The mixture was stirred for 1 hr, and the white solid was collected, and dried under reduced pressure to give the title compound (3.7 g, 70% yield). $^1$H NMR (400 MHz, DMSO-$d_6$), δ 9.91 (br s, 1H), 9.71 (br s, 1H), 8.21 (s, 1H), 8.13 (d, J=8.4 Hz, 1H), 7.67 (d, J=8.4 Hz, 1H), 4.38 (s, 2H), 3.51-3.48 (m, 1H), 3.37-3.32 (m, 1H), 3.10-3.02 (m, 1H), 1.36 (d, J=6.8 Hz, 3H). MS (ESI), m/z: 229 (M$^+$+H$^+$).

Step 5. 4-methyl-7-nitro-2-(pyrimidin-5-yl)-1,2,3,4-tetrahydroisoquinoline

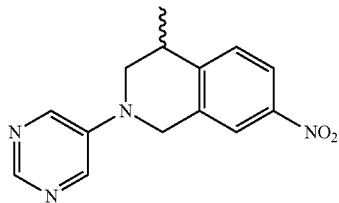 [SMILES: CC1CN(c2cncnc2)Cc2cc([N+](=O)[O-])ccc21]

An oven-dried test tube, which was equipped with a magnetic stir bar and fitted with a teflon septum, was charged with the Pd(dba)$_2$ (10 mmol %), Ruphos (20 mmol %), CsCO$_3$ (3.6 g, 11.0 mmol), 4-methyl-7-nitro-1,2,3,4-tetrahydroisoquinoline hydrochloride (1.0 g, 4.4 mmol), and 5-bromopyrimidine (839 mg, 5.3 mmol). The vessel was evacuated and backfilled with argon and then toluene (20 mL) was added via syringe. The solution was heated to 80° C. overnight, and then cooled to room temperature. The reaction mixture was filtered through a pad of Celite and concentrated under vacuum, and then purified by flash column to yield the title compound (678 mg, 57% yield). MS (ESI), m/z: 271 (M$^+$+H$^+$).

Step 6. 4-methyl-2-(pyrimidin-5-yl)-1,2,3,4-tetrahydroisoquinolin-7-amine

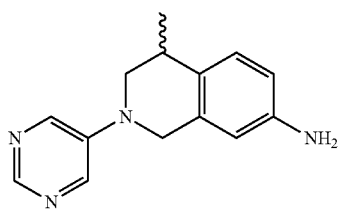 [SMILES: CC1CN(c2cncnc2)Cc2cc(N)ccc21]

To a solution of 4-methyl-7-nitro-2-(pyrimidin-5-yl)-1, 2, 3, 4-tetrahydroisoquinoline (678 mg, 2.5 mmol) in 15 mL of methanol, Pd/C was added, and the reaction flask was evacuated and backfilled with hydrogen twice. The reaction mixture was stirred at room temperature under a hydrogen balloon for 3 hrs. The reaction mixture was filtered through a pad of Celite and concentrated under vacuum to yield the title compound (589 mg, 98% yield).

$^1$H NMR (400 MHz, DMSO-d$_6$), δ 8.52-8.50 (m, 3H), 6.92 (d, J=8.0 Hz, 1H), 6.44 (d, J=8.0 Hz, 1H), 6.0 (s, 1H), 4.92 (s, 2H), 4.36 (d, J=16.0 Hz, 1H), 4.28 (d, J=16.0 Hz, 1H), 3.58-3.54 (m, 1H), 3.30-3.25 (m, 1H), 2.93-2.90 (m, 1H), 1.20 (d, J=6.8 Hz, 3H). MS (ESI), m/z: 241 (M$^+$+H$^+$).

Step 7. N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide

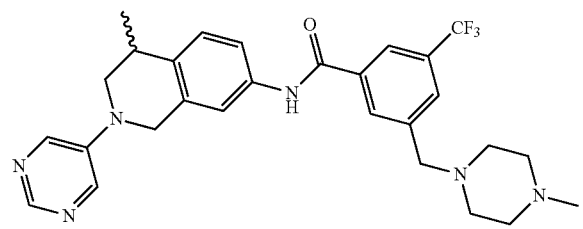 [SMILES: CC1CN(c2cncnc2)Cc2cc(NC(=O)c3cc(CN4CCN(C)CC4)cc(C(F)(F)F)c3)ccc21]

To a solution of 3-((4-methylpiperazin-1-yl)methyl)-5-(trifluoromethyl)benzoic acid (831 mg, 2.8 mmol) in 5 mL of dichloromethane, 4-methyl-2-(pyrimidin-5-yl)-1,2,3,4-tetrahydroisoquinolin-7-amine (589 mg, 2.5 mmol), (1-[bis(dimethylamino)methylene]-1H-1,2,3-triazolo[4,5-b]-pyridinium 3-oxide hexafluorophosphate) (HATU) (1.4 g, 3.8 mmol), and N,N-diisopropylethylamine (DIPEA) (0.9 mL, 5 mmol) were added. The resulting mixture was stirred at room temperature overnight. The reaction was quenched with water and extracted with ethyl acetate. The combined organic layer was dried over anhydrous sodium sulfate, concentrated under vacuum, and then purified by column chromatography over silica gel to afford pure compound 4 (839 mg, 64% yield). $^1$H NMR (400 MHz, DMSO-d$_6$) δ 10.44 (s, 1H), 8.57 (s, 2H), 8.55 (s, 1H), 8.19 (s, 1H), 8.17 (s, 1H), 7.84 (s, 1H), 7.69 (s, 1H), 7.58 (d, J=8.0 Hz, 1H), 7.29 (d, J=8.0 Hz, 1H), 4.55 (d, J=16.0 Hz, 1H), 4.45 (d, J=16.0 Hz, 1H), 3.68-3.59 (m, 3H), 3.42-3.38 (m, 1H), 3.08-3.07 (m, 1H), 2.41 (br s, 4H), 2.33 (br s, 4H), 2.15 (s, 3H), 1.30 (d, J=6.8 Hz, 3H). MS (ESI), m/z: 525 (M$^+$+H$^+$).

Example 3—N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2210)

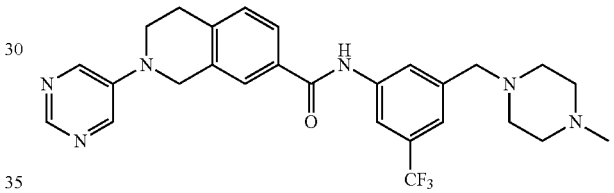

The compound was synthesized by using the procedure similar to that of Example 1. $^1$H NMR (400 MHz, DMSO-d$_6$) δ 10.49 (s, 1H), 8.61-8.55 (s, 3H), 8.19 (s, 1H), 8.00 (s, 1H), 7.88 (s, 1H), 7.82 (d, J=7.6 Hz, 1H), 7.37-7.34 (m, 2H), 4.59 (s, 2H), 3.67 (t, J=5.6 Hz, 2H), 3.52 (s, 2H), 3.01 (d, J=5.2 Hz, 2H), 2.39 (br s, 4H), 2.34 (br s, 4H), 2.14 (s, 3H). MS (ESI), m/z: 511 (M$^+$+H$^+$).

Example 4—N-(3-((4-methylpiperazin-1-yl)methyl)-5-(trifluoromethyl)phenyl)-2-(pyridin-3-yl)-1,2,3,4-tetrahydroisoquinoline-7-carboxamide (D2211)

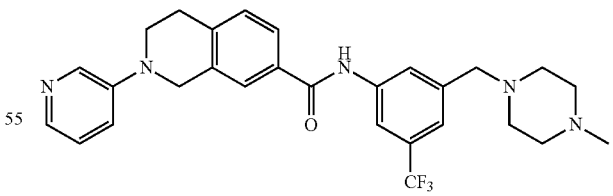

The compound was synthesized by using the procedure similar to that of Example 1. $^1$H NMR (400 MHz, DMSO-d$_6$) δ 10.48 (s, 1H), 8.40 (d, J=2.8 Hz, 1H), 8.19 (s, 1H), 8.01 (s, 1H), 7.98 (d, J=4.0 Hz, 1H), 7.88 (s, 1H), 7.81 (d, J=8.0 Hz, 1H), 7.41 (dd, J=8.0, 2.4 Hz, 1H), 7.36-7.34 (m, 2H), 7.23 (dd, J=8.4, 4.4 Hz, 1H), 4.54 (s, 2H), 3.63 (t, J=5.6 Hz, 2H), 3.54 (s, 2H), 3.00 (t, J=5.6 Hz, 2H), 2.40 (br s, 4H), 2.34 (br s, 4H), 2.15 (s, 3H). MS (ESI), m/z: 510 (M$^+$+H$^+$).

Example 5—N-(3-((4-methylpiperazin-1-yl)methyl)-5-(trifluoromethyl)phenyl)-2-(quinolin-3-yl)-1,2,3,4-tetrahydroisoquinoline-7-carboxamide (D2568)

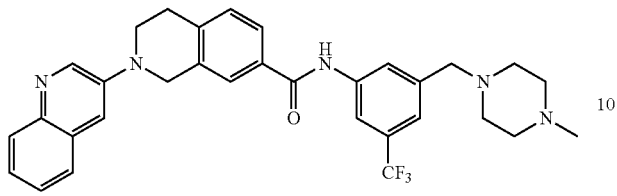

The compound was synthesized by using the procedure similar to that of Example 1. $^1$H NMR (400 MHz, DMSO-$d_6$) δ 10.49 (s, 1H), 8.99 (d, J=2.0 Hz, 1H), 8.20 (s, 1H), 8.02 (s, 1H), 7.93 (s, 1H), 7.89-7.87 (m, 1H), 7.83 (d, J=8.0 Hz, 1H), 7.80-7.78 (m, 1H), 7.63 (s, 1H), 7.50-7.45 (m, 2H), 7.38 (d, J=8.0 Hz, 1H), 7.35 (s, 1H), 4.66 (s, 2H), 3.78 (t, J=5.6 Hz, 2H), 3.54 (s, 2H), 3.08 (t, J=5.6 Hz, 2H), 2.40 (br s, 4H), 2.34 (br s, 4H), 2.16 (s, 3H). MS (ESI), m/z: 560 (M$^+$+H$^+$).

Example 6—4-methyl-N-(3-((4-methylpiperazin-1-yl)methyl)-5-(trifluoromethyl)phenyl)-2-(pyridin-3-yl)-1,2,3,4-tetrahydroisoquinoline-7-carboxamide (D2103)

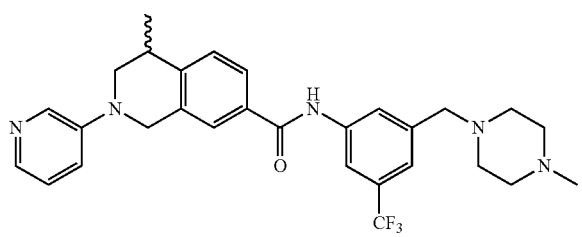 [SMILES: CC1CN(c2cccnc2)Cc2cc(C(=O)Nc3cc(CN4CCN(C)CC4)cc(C(F)(F)F)c3)ccc21]

The compound was synthesized by using the procedure similar to that of Example 1. $^1$H NMR (400 MHz, DMSO-$d_6$) δ 10.49 (s, 1H), 8.40 (s, 1H), 8.19 (s, 1H), 8.01 (s, 1H), 7.98 (d, J=3.2 Hz, 1H), 7.87 (s, 1H), 7.84 (d, J=8.4 Hz, 1H), 7.46 (d, J=8.0 Hz, 1H), 7.40 (d, J=8.0 Hz, 1H), 7.34 (s, 1H), 7.26-7.25 (m, 1H), 4.58 (d, J=16.0 Hz, 1H), 4.47 (d, J=16.0 Hz, 1H), 3.61 (d, J=10 Hz, 1H), 3.54 (s, 2H), 3.43-3.38 (m, 1H), 3.18-3.16 (m, 1H), 2.39 (br s, 4H), 2.34 (br s, 4H), 2.15 (s, 3H), 1.35 (d, J=6.8 Hz, 3H). MS (ESI), m/z: 524 (M$^+$+H$^+$).

Example 7—4,4-dimethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2102)

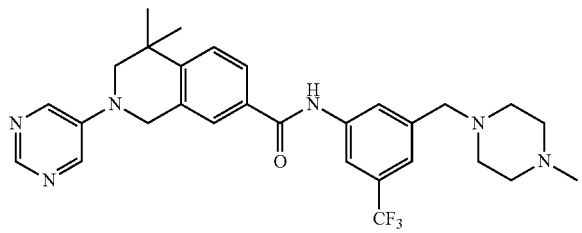 [SMILES: CN1CCN(Cc2cc(NC(=O)c3ccc4c(c3)CN(c3cncnc3)CC4(C)C)cc(C(F)(F)F)c2)CC1]

The compound was synthesized by using the procedure similar to that of Example 1. $^1$H NMR (400 MHz, DMSO-$d_6$) δ 10.37 (s, 1H), 8.65-8.53 (s, 3H), 8.18 (s, 1H) 8.00 (s, 1H), 7.90-7.77 (m, 2H), 7.60 (d, J=6.8 Hz, 1H), 7.34 (s, 1H), 4.58 (s, 2H), 3.53 (s, 2H), 3.45 (s, 2H), 2.39 (br s, 8H), 2.15 (s, 3H), 1.35 (s, 6H). MS (ESI), m/z: 539 (M$^+$+H$^+$).

Example 8—N-(4-chloro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide (D2198)

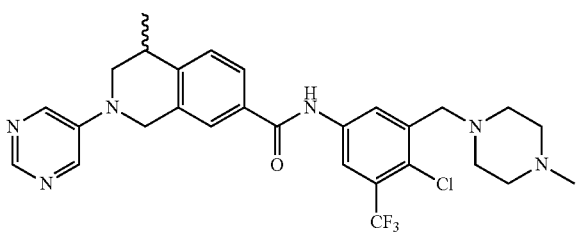 [SMILES: CC1CN(c2cncnc2)Cc2cc(C(=O)Nc3cc(CN4CCN(C)CC4)c(Cl)c(C(F)(F)F)c3)ccc21]

The compound was synthesized by using the procedure similar to that of Example 1. $^1$H NMR (400 MHz, DMSO-$d_6$) δ 10.60 (s, 1H), 8.66-8.52 (m, 3H), 8.35 (s, 1H), 8.23 (s, 1H), 7.86-7.84 (m, 2H), 7.47 (d, J=7.6 Hz, 1H), 4.65 (d, J=16.0 Hz, 1H), 4.53 (d, J=16.0 Hz, 1H), 3.68-3.62 (m, 3H), 3.49-3.44 (m, 1H), 3.19-3.18 (m, 1H), 2.59-2.43 (m, 4H), 2.37 (br s, 4H), 2.17 (s, 3H), 1.34 (d, J=6.8 Hz, 3H). MS (ESI), m/z: 559 (M$^+$+H$^+$).

Example 9—4-methyl-N-(4-methyl-3-((4-methyl-piperazin-1-yl)methyl)-5-(trifluoromethyl)phenyl)-2-(pyrimidin-5-yl)-1,2,3,4-tetrahydroisoquinoline-7-carboxamide (D2274)

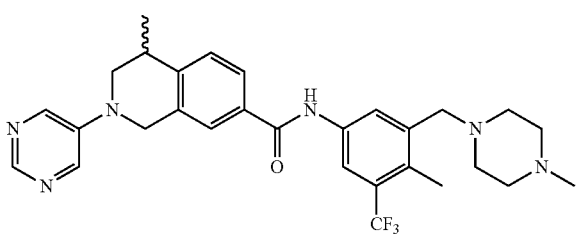

The compound was synthesized by using the procedure similar to that of Example 1. $^1$H NMR (400 MHz, DMSO-$d_6$) δ 10.40 (s, 1H), 8.59-8.56 (m, 3H), 8.17 (s, 1H), 7.95 (s, 1H), 7.85-7.83 (m, 2H), 7.46 (d, J=8.0 Hz, 1H), 4.65 (d, J=16.0 Hz, 1H), 4.53 (d, J=16.0 Hz, 1H), 3.66 (dd, J=12.0, 4.0 Hz, 1H), 3.49-3.44 (m, 3H), 3.18 (q, J=5.6 Hz, 1H), 2.42 (br s, 4H), 2.38 (s, 3H), 2.33 (br s, 4H), 2.15 (s, 3H), 1.34 (d, J=7.2 Hz, 3H). MS (ESI), m/z: 539 (M++H+).

Example 10—4-methyl-N-(3-(2-(4-methylpiperazin-1-yl)ethyl)-5-(trifluoromethyl)phenyl)-2-(pyrimidin-5-yl)-1,2,3,4-tetrahydroisoquinoline-7-carboxamide (D2276)

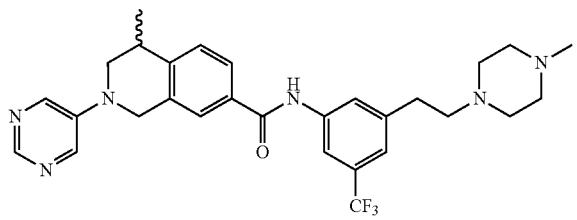 [SMILES: CC1CN(c2cncnc2)Cc2cc(C(=O)Nc3cc(CCN4CCN(C)CC4)cc(C(F)(F)F)c3)ccc21]

The compound was synthesized by using the procedure similar to that of Example 1. $^1$H NMR (400 MHz, DMSO-$d_6$) δ 10.42 (s, 1H), 8.59-8.56 (s, 3H), 8.07 (s, 1H), 7.91 (s, 1H), 7.85-7.83 (m, 2H), 7.47 (d, J=8.0 Hz, 1H), 7.34 (s, 1H), 4.65 (d, J=16.0 Hz, 1H), 4.53 (d, J=16.0 Hz, 1H), 3.66 (dd, J=12.4, 4.4 Hz, 1H), 3.47 (dd, J=12.4, 6.4 Hz, 1H), 3.21-3.17 (m, 1H), 2.82 (t, J=7.2 Hz, 2H), 2.54 (t, J=7.2 Hz, 2H), 2.45 (br s, 4H), 2.31 (br s, 4H), 2.14 (s, 3H), 1.34 (d, J=6.8 Hz, 3H). MS (ESI), m/z: 539 (M$^+$+H$^+$).

Example 11—4-methyl-N-(3-((4-methylpiperazin-1-yl)-5-(trifluoromethyl)phenyl)-2-(pyrimidin-5-yl)-1,2,3,4-tetrahydroisoquinoline-7-carboxamide (D2188)

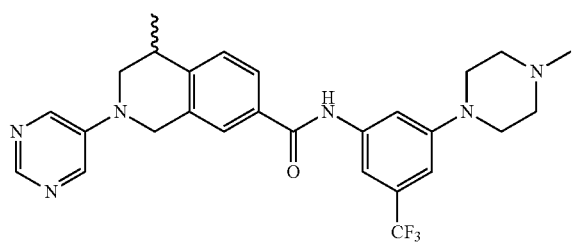 [SMILES: CC1CN(c2cncnc2)Cc2cc(C(=O)Nc3cc(N4CCN(C)CC4)cc(C(F)(F)F)c3)ccc21]

The compound was synthesized by using the procedure similar to that of Example 1. $^1$H NMR (400 MHz, DMSO-$d_6$) δ 10.30 (s, 1H), 8.59-8.55 (m, 3H), 7.84-7.82 (m, 2H), 7.68 (s, 1H), 7.63 (s, 1H), 7.47 (d, J=8.0 Hz, 1H), 6.94 (s, 1H), 4.65 (d, J=16.0 Hz, 1H), 4.53 (d, J=16.0 Hz, 1H), 3.66 (dd, J=12.8, 4.4 Hz, 1H), 3.47 (dd, J=12.4, 6.4 Hz, 1H), 3.23-3.16 (m, 5H), 2.47 (t, J=4.8 Hz, 4H), 2.23 (s, 3H), 1.34 (d, J=6.8 Hz, 3H). MS (ESI), m/z: 511 (M$^+$+H$^+$).

Example 12—4-methyl-N-(4-((4-methylpiperazin-1-yl)methyl)-3-(trifluoromethyl)phenyl)-2-(pyrimidin-5-yl)-1,2,3,4-tetrahydroisoquinoline-7-carboxamide (D2190)

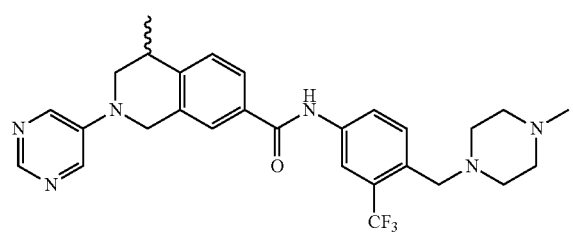 [SMILES: CC1CN(c2cncnc2)Cc2cc(C(=O)Nc3ccc(CN4CCN(C)CC4)c(C(F)(F)F)c3)ccc21]

The compound was synthesized by using the procedure similar to that of Example 1. $^1$H NMR (400 MHz, DMSO-$d_6$) δ 10.48 (s, 1H), 8.59-8.55 (m, 3H), 8.20 (s, 1H), 8.05 (d, J=8.4 Hz, 1H), 7.85-7.83 (m, 2H), 7.70 (d, J=8.4 Hz, 1H), 7.47 (d, J=8.4 Hz, 1H), 4.65 (d, J=16.0 Hz, 1H), 4.53 (d, J=16.0 Hz, 1H), 3.66 (dd, J=12.8, 4.4 Hz, 1H), 3.56 (s, 2H), 3.47 (dd, J=12.4, 6.0 Hz, 1H), 3.20-3.16 (m, 1H), 2.38 (br s, 4H), 2.33 (br s, 4H), 2.15 (s, 3H), 1.34 (d, J=6.8 Hz, 3H). MS (ESI), m/z: 525 (M$^+$+H$^+$).

Example 13—4-methyl-2-(pyrimidin-5-yl)-N-(3-(trifluoromethyl)phenyl)-1,2,3,4-tetrahydroisoquinoline-7-carboxamide (D2199)

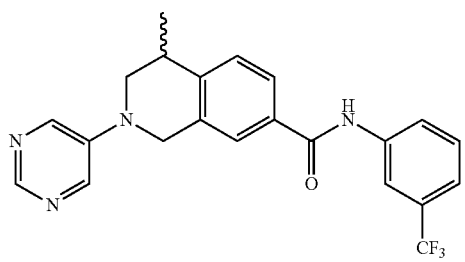 [SMILES: CC1CN(c2cncnc2)Cc2cc(C(=O)Nc3cccc(C(F)(F)F)c3)ccc21]

The compound was synthesized by using the procedure similar to that of Example 1. $^1$H NMR (400 MHz, DMSO-$d_6$) δ 10.52 (s, 1H), 8.58 (s, 2H), 8.57 (s, 1H), 8.24 (s, 1H), 8.06 (d, J=8.0 Hz, 1H), 7.86-7.84 (m, 2H), 7.60 (t, J=8.0 Hz, 1H), 7.49-7.44 (m, 2H), 4.65 (d, J=16.0 Hz, 1H), 4.53 (d, J=16.0 Hz, 1H), 3.66 (dd, J=12.4, 4.4 Hz, 1H), 3.47 (dd, J=12.4, 6.4 Hz, 1H), 3.21-3.17 (m, 1H), 1.34 (d, J=6.8 Hz, 3H). MS (ESI), m/z: 413 (M$^+$+H$^+$).

Example 14—4-methyl-N-(3-((4-methyl-1,4-diazepan-1-yl)methyl)-5-(trifluoromethyl)phenyl)-2-(pyrimidin-5-yl)-1,2,3,4-tetrahydroisoquinoline-7-carboxamide (D2197)

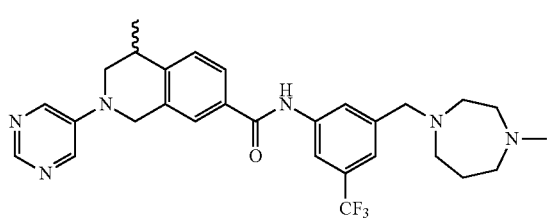 [SMILES: CC1CN(c2cncnc2)Cc2cc(C(=O)Nc3cc(CN4CCCN(C)CC4)cc(C(F)(F)F)c3)ccc21]

The compound was synthesized by using the procedure similar to that of Example 1. $^1$H NMR (500 MHz, DMSO-$d_6$) δ 10.51 (s, 1H), 8.58 (s, 2H), 8.57 (s, 1H), 8.16 (s, 1H), 8.02 (s, 1H), 7.86-7.84 (m, 2H), 7.47 (d, J=8.0 Hz, 1H), 7.37 (s, 1H), 4.66 (d, J=16.0 Hz, 1H), 4.53 (d, J=16.0 Hz, 1H), 3.69-3.64 (m, 3H), 3.49-3.45 (m, 1H), 3.20-3.17 (m, 1H), 2.67-2.63 (m, 4H), 2.58-2.52 (m, 4H), 2.25 (s, 3H), 1.75-1.70 (m, 2H), 1.34 (d, J=7.0 Hz, 3H). MS (ESI), m/z: 539 (M$^+$+H$^+$).

Example 15—N-(3-ethyl-5-((4-methylpiperazin-1-yl)methyl)phenyl)-4-methyl-2-(pyrimidin-5-yl)-1,2,3,4-tetrahydroisoquinoline-7-carboxamide (D2193)

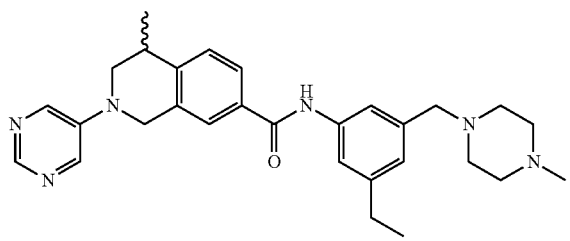 [SMILES: CCc1cc(CN2CCN(C)CC2)cc(NC(=O)c2ccc3c(c2)CN(c2cncnc2)CC3C)c1]

The compound was synthesized by using the procedure similar to that of Example 1. $^1$H NMR (400 MHz, DMSO-$d_6$) δ 10.12 (s, 1H), 8.65-8.50 (m, 3H), 7.84-7.81 (m, 2H), 7.57 (s, 1H), 7.54 (s, 1H), 7.44 (d, J=7.2 Hz, 1H), 6.86 (s, 1H), 4.64 (d, J=15.6 Hz, 1H), 4.52 (d, J=15.6 Hz, 1H), 3.67-3.64 (m, 1H), 3.47-3.40 (m, 3H), 3.23-3.11 (m, 1H), 2.60-2.58 (m, 2H), 2.46-2.22 (m, 8H), 2.14 (s, 3H), 1.34 (d, J=6.0 Hz, 3H), 1.19 (t, J=6.4 Hz, 3H). MS (ESI), m/z: 485 (M$^+$+H$^+$).

Example 16—N-(3-isopropyl-5-((4-methylpiperazin-1-yl)methyl)phenyl)-4-methyl-2-(pyrimidin-5-yl)-1,2,3,4-tetrahydroisoquinoline-7-carboxamide (D2187)

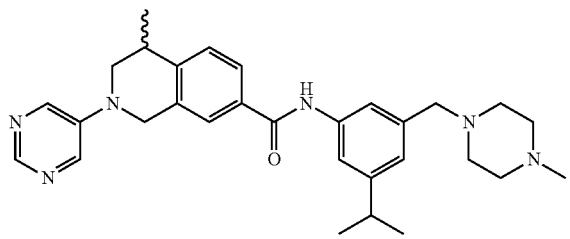 [SMILES: CC(C)c1cc(CN2CCN(C)CC2)cc(NC(=O)c2ccc3c(c2)CN(c2cncnc2)CC3C)c1]

The compound was synthesized by using the procedure similar to that of Example 1. $^1$H NMR (400 MHz, DMSO-$d_6$) δ 10.11 (s, 1H), 8.61-8.53 (m, 3H), 7.84-7.81 (m, 2H), 7.58 (s, 1H), 7.57 (s, 1H), 7.44 (d, J=7.6 Hz, 1H), 6.88 (s, 1H), 4.64 (d, J=16.0 Hz, 1H), 4.52 (d, J=16.0 Hz, 1H), 3.67-3.64 (m, 1H), 3.48-3.41 (m, 3H), 3.18-3.17 (m, 1H), 2.87-2.84 (m, 1H), 2.36-2.33 (m, 8H), 2.14 (s, 3H), 1.34 (d, J=6.4 Hz, 3H), 1.21 (d, J=6.4 Hz, 6H). MS (ESI), m/z: 499 (M$^+$+H$^+$).

Example 17—N-(3-((4-ethylpiperazin-1-yl)methyl)-5-(trifluoromethyl)phenyl)-4-methyl-2-(pyrimidin-5-yl)-1,2,3,4-tetrahydroisoquinoline-7-carboxamide (D2275)

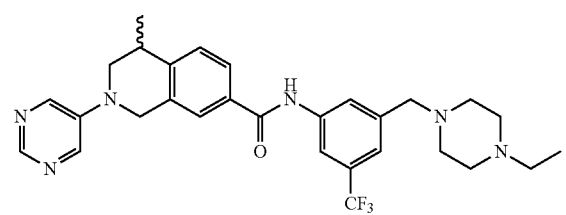 [SMILES: CCN1CCN(Cc2cc(NC(=O)c3ccc4c(c3)CN(c3cncnc3)CC4C)cc(C(F)(F)F)c2)CC1]

The compound was synthesized by using the procedure similar to that of Example 1. $^1$H NMR (400 MHz, DMSO-$d_6$) δ 10.50 (s, 1H), 8.60-8.55 (m, 3H), 8.19 (s, 1H), 8.00 (s, 1H), 7.86-7.84 (m, 2H), 7.47 (d, J=8.0 Hz, 1H), 7.34 (s, 1H), 4.65 (d, J=16.0 Hz, 1H), 4.53 (d, J=16.0 Hz, 1H), 3.66 (dd, J=12.4, 4.4 Hz, 1H), 3.54 (s, 2H), 3.47 (dd, J=12.8, 6.4 Hz, 1H), 3.21-3.16 (m, 1H), 2.48-2.33 (m, 8H), 2.30 (q, J=7.2 Hz, 3H), 1.34 (d, J=6.8 Hz, 3H), 0.97 (t, J=7.2 Hz, 3H). MS (ESI), m/z: 539 (M$^+$+H$^+$).

Example 18—4-methyl-N-(3-(morpholinomethyl)-5-(trifluoromethyl)phenyl)-2-(pyrimidin-5-yl)-1,2,3,4-tetrahydroisoquinoline-7-carboxamide (D2201)

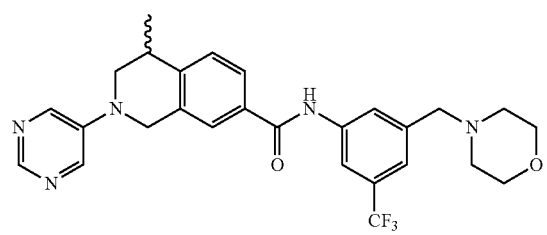 [SMILES: CC1CN(c2cncnc2)Cc2cc(C(=O)Nc3cc(CN4CCOCC4)cc(C(F)(F)F)c3)ccc21]

The compound was synthesized by using the procedure similar to that of Example 1. $^1$H NMR (400 MHz, DMSO-$d_6$) δ 10.49 (s, 1H), 8.61-8.54 (m, 3H), 8.19 (s, 1H), 8.03 (s, 1H), 7.87-7.85 (m, 2H), 7.47 (d, J=8.0 Hz, 1H), 7.37 (s, 1H), 4.65 (d, J=16.0 Hz, 1H), 4.53 (d, J=16.0 Hz, 1H), 3.66 (dd, J=12.4, 4.0 Hz, 1H), 3.60-3.59 (m, 4H), 3.55 (s, 2H), 3.47 (dd, J=12.4, 6.0 Hz, 1H), 3.21-3.17 (m, 1H), 2.43-2.35 (m, 4H), 1.34 (d, J=6.8 Hz, 3H). MS (ESI), m/z: 512 (M$^+$+H$^+$).

Example 19—4-methyl-N-(3-(piperidin-1-ylmethyl)-5-(trifluoromethyl)phenyl)-2-(pyrimidin-5-yl)-1,2,3,4-tetrahydroisoquinoline-7-carboxamide (D2194)

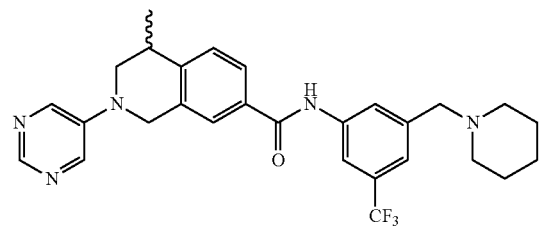

The compound was synthesized by using the procedure similar to that of Example 1. $^1$H NMR (400 MHz, DMSO-$d_6$) δ 10.50 (s, 1H), 8.61-8.54 (m, 3H), 8.18 (s, 1H), 7.99 (s, 1H), 7.86-7.84 (m, 2H), 7.47 (d, J=7.6 Hz, 1H), 7.34 (s, 1H), 4.65 (d, J=16.0 Hz, 1H), 4.53 (d, J=16.0 Hz, 1H), 3.66 (dd, J=12.0, 4.0 Hz, 1H), 3.50 (s, 2H), 3.48-3.45 (m, 1H), 3.19-3.18 (m, 1H), 2.40-2.30 (m, 4H), 1.51-1.50 (m, 4H), 1.45-1.37 (m, 2H), 1.34 (d, J=6.8 Hz, 3H). MS (ESI), m/z: 510 (M$^+$+H$^+$).

Example 20—4-methyl-2-(pyrimidin-5-yl)-N-(3-(pyrrolidin-1-ylmethyl)-5-(trifluoromethyl)phenyl)-1,2,3,4-tetrahydroisoquinoline-7-carboxamide (D2573)

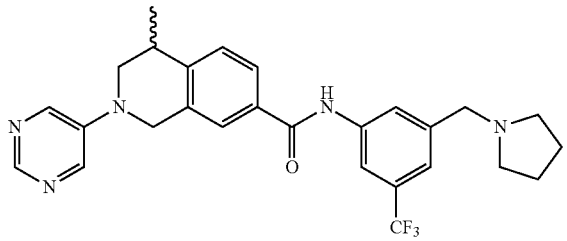 [SMILES: CC1CN(c2cncnc2)Cc2cc(C(=O)Nc3cc(CN4CCCC4)cc(C(F)(F)F)c3)ccc21]

The compound was synthesized by using the procedure similar to that of Example 1. $^1$H NMR (400 MHz, DMSO-$d_6$) δ 10.48 (s, 1H), 8.60-8.55 (m, 3H), 8.18 (s, 1H), 8.02 (s, 1H), 7.87-7.85 (m, 2H), 7.47 (d, J=8.0 Hz, 1H), 7.35 (s, 1H), 4.65 (d, J=16.4 Hz, 1H), 4.53 (d, J=16.4 Hz, 1H), 3.68-3.64 (m, 3H), 3.49-3.45 (m, 1H), 3.21-3.16 (m, 1H), 2.50-2.47 (m, 4H), 1.76-1.70 (m, 4H), 1.34 (d, J=6.8 Hz, 3H). MS (ESI), m/z: 496 (M$^+$+H$^+$).

Example 21—N-(3-((dimethylamino)methyl)-5-(trifluoromethyl)phenyl)-4-methyl-2-(pyrimidin-5-yl)-1,2,3,4-tetrahydroisoquinoline-7-carboxamide (D2192)

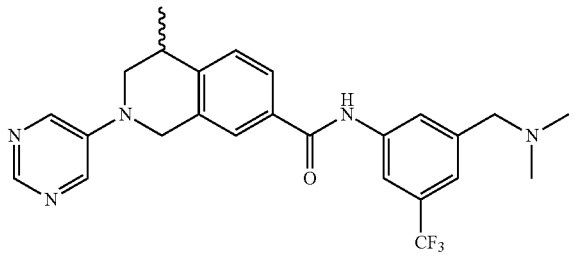 [SMILES: CC1CN(c2cncnc2)Cc2cc(C(=O)Nc3cc(CN(C)C)cc(C(F)(F)F)c3)ccc21]

The compound was synthesized by using the procedure similar to that of Example 1. $^1$H NMR (400 MHz, DMSO-$d_6$) δ 10.48 (s, 1H), 8.58-8.57 (m, 3H), 8.18 (s, 1H), 8.02 (s, 1H), 7.87-7.85 (m, 2H), 7.47 (d, J=8.0 Hz, 1H), 7.35 (s, 1H), 4.65 (d, J=16.4 Hz, 1H), 4.53 (d, J=16.4 Hz, 1H), 3.66 (dd, J=12.4, 4.4 Hz, 1H), 3.50-3.45 (m, 3H), 3.21-3.17 (m, 1H), 2.19 (s, 6H), 1.34 (d, J=7.2 Hz, 3H). MS (ESI), m/z: 470 (M$^+$+H$^+$).

Example 22—N-(3-cyclohexyl-5-((4-methylpiperazin-1-yl)methyl)phenyl)-4-methyl-2-(pyrimidin-5-yl)-1,2,3,4-tetrahydroisoquinoline-7-carboxamide (D2215)

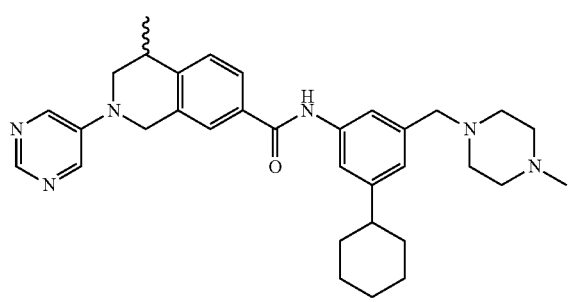 [SMILES: CC1CN(c2cncnc2)Cc2cc(C(=O)Nc3cc(CN4CCN(C)CC4)cc(C4CCCCC4)c3)ccc21]

The compound was synthesized by using the procedure similar to that of Example 1. $^1$H NMR (400 MHz, DMSO-$d_6$) δ 10.09 (s, 1H), 8.63-8.53 (m, 3H), 7.84-7.81 (m, 2H), 7.58 (s, 1H), 7.55 (s, 1H), 7.44 (d, J=7.6 Hz, 1H), 6.86 (s, 1H), 4.64 (d, J=16.0 Hz, 1H), 4.52 (d, J=16.0 Hz, 1H), 3.67-3.65 (m, 1H), 3.49-3.44 (m, 1H), 3.41 (s, 2H), 3.22-3.12 (m, 1H), 2.34-2.21 (m, 8H), 2.15 (s, 3H), 1.88-1.75 (m, 4H), 1.73-1.70 (m, 1H), 1.40-1.33 (m, 7H), 1.29-1.17 (m, 1H). MS (ESI), m/z: 539 (M$^+$+H$^+$).

Example 23—N-(3-(((2-(dimethylamino)ethyl)(methyl)amino)methyl)-5-(trifluoromethyl)phenyl)-4-methyl-2-(pyrimidin-5-yl)-1,2,3,4-tetrahydroisoquinoline-7-carboxamide (D2474)

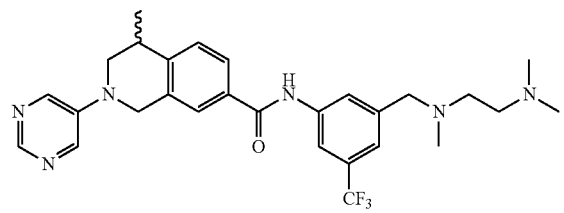 [SMILES: CC1CN(c2cncnc2)Cc2cc(C(=O)Nc3cc(CN(C)CCN(C)C)cc(C(F)(F)F)c3)ccc21]

The compound was synthesized by using the procedure similar to that of Example 1. $^1$H NMR (400 MHz, DMSO-$d_6$) δ 10.51 (s, 1H), 8.67-8.51 (m, 3H), 8.17 (s, 1H), 8.00 (s, 1H), 7.92-7.79 (m, 2H), 7.47 (d, J=7.2 Hz, 1H), 7.37 (s, 1H), 4.65 (d, J=16.4 Hz, 1H), 4.53 (d, J=16.4 Hz, 1H), 3.67-3.65 (m, 1H), 3.57 (s, 3H), 3.52-3.43 (m, 1H), 3.24-3.12 (m, 1H), 2.48-2.42 (m, 2H), 2.42-2.32 (m, 2H), 2.17 (s, 3H), 2.12 (s, 6H), 1.42-1.25 (m, 3H). MS (ESI), m/z: 527 (M$^+$+H$^+$).

Example 24—N-(3-(((R)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide (D2473)

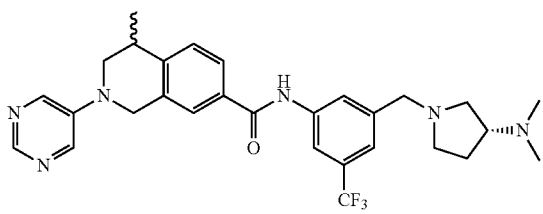 [SMILES: CC1CN(c2cncnc2)Cc2cc(C(=O)Nc3cc(CN4CC[C@@H](N(C)C)C4)cc(C(F)(F)F)c3)ccc21]

The compound was synthesized by using the procedure similar to that of Example 1. $^1$H NMR (400 MHz, DMSO-$d_6$) δ 10.50 (s, 1H), 8.64-8.51 (m, 3H), 8.17 (s, 1H), 8.01 (s, 1H), 7.92-7.80 (m, 2H), 7.47 (d, J=6.8 Hz, 1H), 7.37 (s, 1H), 4.65 (d, J=16.0 Hz, 1H), 4.53 (d, J=16.0 Hz, 1H), 3.72-3.65 (m, 2H), 3.59-3.57 (m, 1H), 3.53-3.42 (m, 1H), 3.26-3.10 (m, 1H), 2.79-2.65 (m, 2H), 2.65-2.56 (m, 1H), 2.50-2.40 (m, 1H), 2.36-2.26 (m, 1H), 2.08 (s, 6H), 1.93-1.80 (m, 1H), 1.69-1.56 (m, 1H), 1.34 (d, J=5.2 Hz, 3H). MS (ESI), m/z: 539 (M$^+$+H$^+$).

Example 25—N-(3-(((S)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide (D2475)

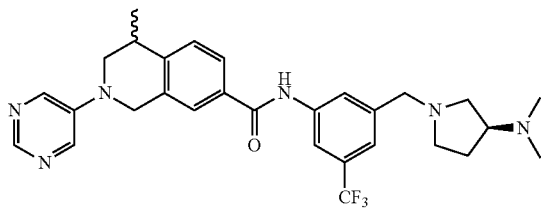 [SMILES: CC1CN(c2cncnc2)Cc2cc(C(=O)Nc3cc(CN4CC[C@H](N(C)C)C4)cc(C(F)(F)F)c3)ccc21]

The compound was synthesized by using the procedure similar to that of Example 1. $^1$H NMR (400 MHz, DMSO-$d_6$) δ 10.50 (s, 1H), 8.64-8.51 (m, 3H), 8.17 (s, 1H), 8.01 (s, 1H), 7.92-7.80 (m, 2H), 7.55-7.43 (m, 1H), 7.35 (s, 1H), 4.65 (d, J=15.6 Hz, 1H), 4.53 (d, J=15.6 Hz, 1H), 3.76-3.62 (m, 2H), 3.62-3.53 (m, 1H), 3.52-3.42 (m, 1H), 3.25-3.11 (m, 1H), 2.79-2.65 (m, 2H), 2.65-2.56 (m, 1H), 2.50-2.40 (m, 1H), 2.36-2.26 (m, 1H), 2.08 (s, 6H), 1.94-1.77 (m, 1H), 1.70-1.55 (m, 1H), 1.43-1.27 (m, 3H). MS (ESI), m/z: 539 (M$^+$+H$^+$).

Example 26—4-methyl-N-(3-(4-methyl-1H-imidazol-1-yl)-5-(trifluoromethyl)phenyl)-2-(pyrimidin-5-yl)-1,2,3,4-tetrahydroisoquinoline-7-carboxamide (D2202)

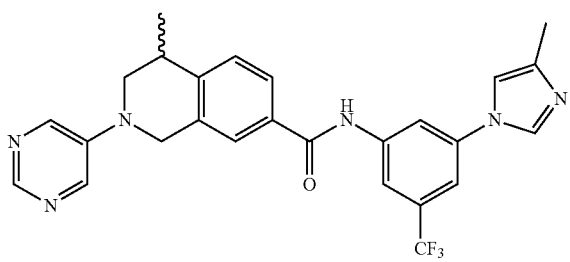 [SMILES: Cc1cn(-c2cc(NC(=O)c3ccc4c(c3)CN(c3cncnc3)CC4C)cc(C(F)(F)F)c2)cn1]

The compound was synthesized by using the procedure similar to that of Example 1. $^1$H NMR (400 MHz, DMSO-$d_6$) δ 10.66 (s, 1H), 8.58-8.57 (m, 3H), 8.29 (s, 1H), 8.20 (s, 1H), 8.15 (s, 1H), 7.88-7.86 (m, 2H), 7.73 (s, 1H), 7.51-7.48 (m, 2H), 4.66 (d, J=16.0 Hz, 1H), 4.54 (d, J=16 Hz, 1H), 3.67 (dd, J=12.8, 4.8 Hz, 1H), 3.48 (dd, J=12.4, 6.4 Hz, 1H), 3.22-3.18 (m, 1H), 2.18 (s, 3H), 1.35 (d, J=6.8 Hz, 3H). MS (ESI), m/z: 493 (M$^+$+H$^+$).

Example 27—N-(4-fluoro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide (D2214)

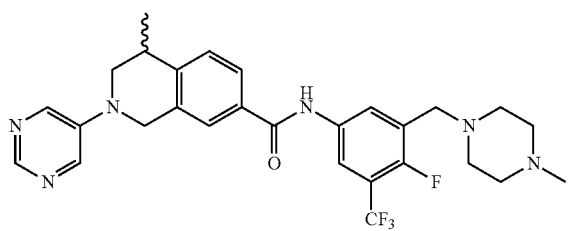 [SMILES: CC1CN(c2cncnc2)Cc2cc(C(=O)Nc3cc(CN4CCN(C)CC4)c(F)c(C(F)(F)F)c3)ccc21]

The compound was synthesized by using the procedure similar to that of Example 1. $^1$H NMR (500 MHz, DMSO-$d_6$) δ 10.53 (s, 1H), 8.58 (s, 2H), 8.57 (s, 1H), 8.22 (dd, J=6.0, 2.5 Hz, 1H), 8.12 (dd, J=6.0, 2.5 Hz, 1H), 7.86-7.84 (m, 2H), 7.47 (d, J=8.0 Hz, 1H), 4.65 (d, J=16.0 Hz, 1H), 4.53 (d, J=16.0 Hz, 1H), 3.66 (dd, J=12.5, 4.5 Hz, 1H), 3.58 (s, 2H), 3.47 (dd, J=12.5, 6.5 Hz, 1H), 3.22-23.16 (m, 1H), 2.44 (br s, 4H), 2.36-2.35 (m, 4H), 2.15 (s, 3H), 1.34 (d, J=7.0 Hz, 3H). MS (ESI), m/z: 543 (M$^+$+H$^+$).

Example 28—N-(3-tert-butyl-5-((4-methylpiperazin-1-yl)methyl)phenyl)-4-methyl-2-(pyrimidin-5-yl)-1,2,3,4-tetrahydroisoquinoline-7-carboxamide (D2350)

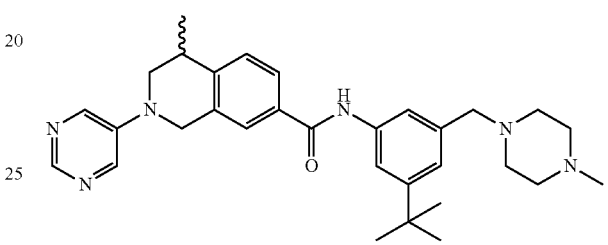

The compound was synthesized by using the procedure similar to that of Example 1. $^1$H NMR (400 MHz, DMSO-$d_6$) δ 10.12 (s, 1H), 8.58 (s, 2H), 8.57 (s, 1H), 7.84-7.82 (m, 2H), 7.70 (s, 1H), 7.63 (s, 1H), 7.44 (d, J=8.0 Hz, 1H), 7.04 (s, 1H), 4.65 (d, J=16.0 Hz, 1H), 4.52 (d, J=16.0 Hz, 1H), 3.68-3.64 (m, 1H), 3.49-3.45 (m, 1H), 3.44 (s, 1H), 3.20-3.16 (m, 1H), 2.48-2.18 (m, 8H), 2.15 (s, 3H), 1.34 (d, J=7.0 Hz, 3H), 1.28 (s, 9H). MS (ESI), m/z: 513 (M$^+$+H$^+$).

Example 29—4-methyl-N-(5-((4-methylpiperazin-1-yl)methyl)biphenyl-3-yl)-2-(pyrimidin-5-yl)-1,2,3,4-tetrahydroisoquinoline-7-carboxamide (D2476)

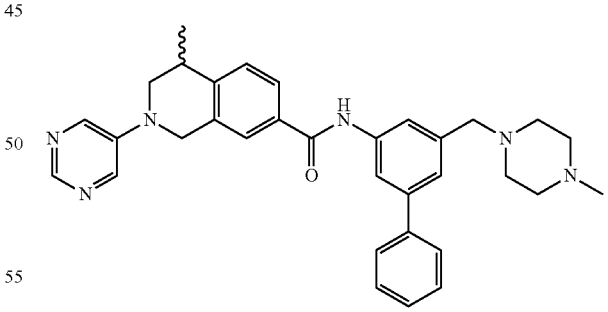

The compound was synthesized by using the procedure similar to that of Example 1. $^1$H NMR (400 MHz, DMSO-$d_6$) δ 10.29 (s, 1H), 8.58 (s, 2H), 8.57 (s, 1H), 8.04 (s, 1H), 7.87-7.85 (m, 2H), 7.76 (s, 1H), 7.63 (d, J=7.5 Hz, 2H), 7.50-7.46 (m, 3H), 7.38 (t, J=7.0 Hz, 1H), 7.30 (s, 1H), 4.65 (d, J=16.0 Hz, 1H), 4.53 (d, J=16.0 Hz, 1H), 3.68-3.65 (m, 1H), 3.52 (s, 1H), 3.49-3.46 (m, 1H), 3.19-3.18 (m, 1H), 2.42 (br s, 4H), 2.36 (br s, 4H), 2.15 (s, 3H), 1.34 (d, J=6.5 Hz, 3H), 1.28 (s, 9H). MS (ESI), m/z: 533 (M$^+$+H$^+$).

Example 30—3-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2574)

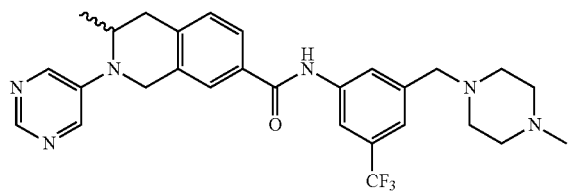 [SMILES: CC1Cc2ccc(C(=O)Nc3cc(CN4CCN(C)CC4)cc(C(F)(F)F)c3)cc2CN1c1cncnc1]

The compound was synthesized by using the procedure similar to that of Example 1. $^1$H NMR (400 MHz, DMSO-$d_6$) δ 10.52 (s, 1H), 8.56-8.54 (m, 3H), 8.19 (s, 1H), 8.00 (s, 1H), 7.90 (s, 1H), 7.85 (d, J=7.5 Hz, 1H), 7.41 (d, J=7.5 Hz, 1H), 7.35 (s, 1H), 4.72 (d, J=16.5 Hz, 1H), 4.60-4.50 (m, 1H), 4.33 (d, J=16.5 Hz, 1H), 3.54 (s, 2H), 3.25-3.22 (m, 1H), 2.86-2.83 (m, 1H), 2.46-2.21 (m, 8H), 2.15 (s, 3H), 0.99 (d, J=6.0 Hz, 3H). MS (ESI), m/z: 525 (M$^+$+H$^+$).

Example 31—N-(3-cyclopropyl-5-((4-methylpiperazin-1-yl)methyl)phenyl)-4-methyl-2-(pyrimidin-5-yl)-1,2,3,4-tetrahydroisoquinoline-7-carboxamide (D2347)

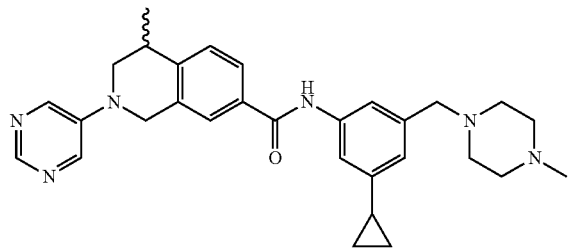 [SMILES: CC1CN(c2cncnc2)Cc2cc(C(=O)Nc3cc(CN4CCN(C)CC4)cc(C4CC4)c3)ccc21]

The compound was synthesized by using the procedure similar to that of Example 1. $^1$H NMR (400 MHz, DMSO-$d_6$) δ 10.09 (s, 1H), 8.65-8.54 (m, 3H), 7.83-7.81 (m, 2H), 7.51 (s, 1H), 7.44 (d, J=7.5 Hz, 1H), 7.39 (s, 1H), 6.76 (s, 1H), 4.64 (d, J=16.0 Hz, 1H), 4.52 (d, J=16.0 Hz, 1H), 3.67-3.64 (m, 1H), 3.48-3.44 (m, 1H), 3.38 (s, 2H), 3.22-3.13 (m, 1H), 2.47-2.21 (m, 8H), 2.14 (s, 3H), 1.90-1.89 (m, 1H), 1.34 (d, J=6.5 Hz, 3H), 0.96-0.94 (m, 2H), 0.63-0.62 (m, 2H). MS (ESI), m/z: 497 (M$^+$+H$^+$).

Example 32—N-(3-cyclopentyl-5-((4-methylpiperazin-1-yl)methyl)phenyl)-4-methyl-2-(pyrimidin-5-yl)-1,2,3,4-tetrahydroisoquinoline-7-carboxamide (D2196)

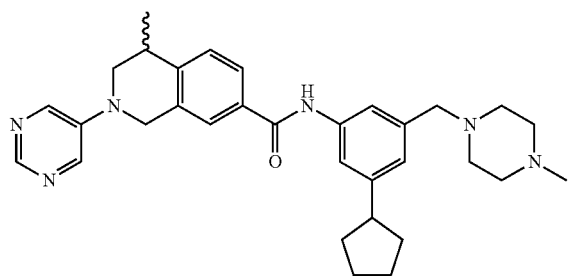 [SMILES: CC1CN(c2cncnc2)Cc2cc(C(=O)Nc3cc(CN4CCN(C)CC4)cc(C4CCCC4)c3)ccc21]

The compound was synthesized by using the procedure similar to that of Example 1. $^1$H NMR (400 MHz, DMSO-$d_6$) δ 10.10 (s, 1H), 8.60-8.54 (m, 3H), 7.84-7.81 (m, 2H), 7.60 (s, 1H), 7.56 (s, 1H), 7.44 (d, J=8.0 Hz, 1H), 6.89 (s, 1H), 4.64 (d, J=16.0 Hz, 1H), 4.52 (d, J=16.0 Hz, 1H), 3.66 (dd, J=12.4, 4.4 Hz, 1H), 3.49-3.44 (m, 1H), 3.41 (s, 2H), 3.19-3.15 (m, 1H), 3.00-2.91 (m, 1H), 2.37-2.33 (m, 8H), 2.15 (s, 3H), 2.02-1.98 (m, 2H), 1.81-1.73 (m, 2H), 1.70-1.64 (m, 2H), 1.57-1.48 (m, 2H), 1.34 (d, J=6.8 Hz, 3H). MS (ESI), m/z: 525 (M$^+$+H$^+$).

Example 33—N-(3-((4-cyclohexylpiperazin-1-yl)methyl)-5-(trifluoromethyl)phenyl)-4-methyl-2-(pyrimidin-5-yl)-1,2,3,4-tetrahydroisoquinoline-7-carboxamide (D2195)

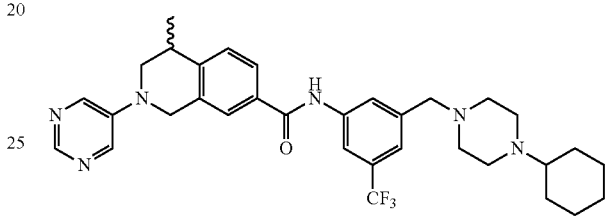

The compound was synthesized by using the procedure similar to that of Example 1. $^1$H NMR (400 MHz, DMSO-$d_6$) δ 10.49 (s, 1H), 8.63-8.51 (m, 3H), 8.19 (s, 1H), 7.99 (s, 1H), 7.86-7.84 (m, 2H), 7.46 (d, J=8.0 Hz, 1H), 7.33 (s, 1H), 4.64 (d, J=16.4 Hz, 1H), 4.52 (d, J=16.0 Hz, 1H), 3.67-3.63 (m, 1H), 3.51 (s, 2H), 3.49-3.44 (m, 1H), 3.19-3.17 (m, 1H), 2.50-2.39 (m, 8H), 2.24-2.10 (m, 1H), 1.73-1.69 (m, 4H), 1.55-1.53 (m, 1H), 1.34 (d, J=6.8 Hz, 3H), 1.24-1.11 (m, 4H), 1.10-0.97 (m, 1H). MS (ESI), m/z: 593 (M$^+$+H$^+$).

Example 34—4-ethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2213)

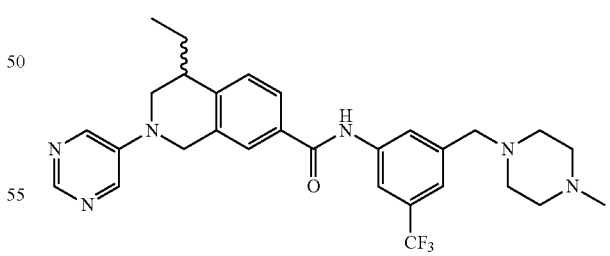

The compound was synthesized by using the procedure similar to that of Example 1. $^1$H NMR (400 MHz, DMSO-$d_6$) δ 10.50 (s, 1H), 8.61-8.52 (m, 3H), 8.18 (s, 1H) 8.00 (s, 1H), 7.87-7.83 (m, 2H), 7.43 (d, J=8.0 Hz, 1H), 7.34 (s, 1H), 4.71 (d, J=16.0 Hz, 1H), 4.44 (d, J=16.0 Hz, 1H), 3.84-3.80 (m, 1H), 3.54 (s, 2H), 3.45-3.42 (m, 1H), 3.02-2.92 (m, 1H), 2.40 (br s, 4H), 2.36 (br s, 4H), 2.15 (s, 3H), 1.71-1.67 (m, 2H), 0.99 (t, J=7.2 Hz, 3H). MS (ESI). m/z: 539 (M$^+$+H$^+$).

Example 35—4-methyl-2-(pyrimidin-5-yl)-N-(3-(thiomorpholinomethyl)-5-(trifluoromethyl)phenyl)-1,2,3,4-tetrahydroisoquinoline-7-carboxamide (D2191)

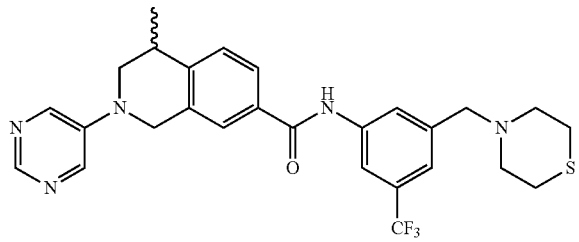 [SMILES: CC1CN(c2cncnc2)Cc2cc(C(=O)Nc3cc(CN4CCSCC4)cc(C(F)(F)F)c3)ccc21]

The compound was synthesized by using the procedure similar to that of Example 1. $^1$H NMR (400 MHz, DMSO-$d_6$) δ 10.51 (s, 1H), 8.62-8.53 (m, 3H), 8.19 (s, 1H), 8.01 (s, 1H), 7.86-7.84 (m, 2H), 7.47 (d, J=8.0 Hz, 1H), 7.35 (s, 1H), 4.65 (d, J=16.4 Hz, 1H), 4.53 (d, J=16.0 Hz, 1H), 3.66 (dd, J=12.4, 4.4 Hz, 1H), 3.60-3.59 (m, 2H), 3.47 (dd, J=12.4, 6.0 Hz, 1H), 3.19-3.18 (m, 1H), 2.65-2.64 (m, 8H), 1.34 (d, J=6.4 Hz, 3H). MS (ESI), m/z: 528 (M$^+$+H$^+$).

Example 36—3-((4-methylpiperazin-1-yl)methyl)-N-(2-(pyrimidin-5-yl)-1,2,3,4-tetrahydroisoquinolin-7-yl)-5-(trifluoromethyl)benzamide (D2212)

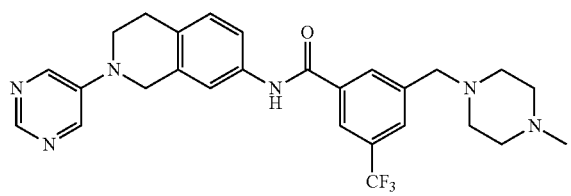 [SMILES: CN1CCN(Cc2cc(C(=O)Nc3ccc4c(c3)CN(c3cncnc3)CC4)cc(C(F)(F)F)c2)CC1]

The compound was synthesized by using the procedure similar to that of Example 2. $^1$H NMR (400 MHz, DMSO-$d_6$) δ 10.44 (s, 1H), 8.57 (s, 2H), 8.55 (s, 1H) 8.20 (s, 1H), 8.17 (s, 1H), 7.84 (s, 1H), 7.70 (s, 1H), 7.55 (d, J=8.4 Hz, 1H), 7.19 (d, J=8.0 Hz, 1H), 4.51 (s, 2H), 3.66-3.63 (m, 4H), 2.96-2.86 (m, 2H), 2.41 (br s, 4H), 2.34 (br s, 4H), 2.15 (s, 3H). MS (ESI), m/z: 511 (M$^+$+H$^+$).

Example 37—(S)-4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2099)

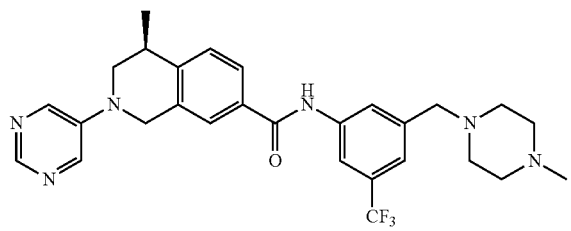 [SMILES: C[C@@H]1CN(c2cncnc2)Cc2cc(C(=O)Nc3cc(CN4CCN(C)CC4)cc(C(F)(F)F)c3)ccc21]

The compound was synthesized by using the procedure similar to that of Example 1. $^1$H NMR (400 MHz, DMSO-$d_6$) δ 10.50 (s, 1H), 8.60-8.55 (m, 3H), 8.19 (s, 1H), 8.00 (s, 1H), 7.86-7.84 (s, 2H), 7.47 (d, J=8.0 Hz, 1H), 7.35 (s, 1H), 4.65 (d, J=16.0 Hz, 1H), 4.53 (d, J=16.0 Hz, 1H), 3.66 (dd, J=12.0, 3.6 Hz, 1H), 3.54 (s, 2H), 3.47 (dd, J=12.4, 6.4 Hz, 1H), 3.19-3.18 (m, 1H), 2.40 (br s, 4H), 2.33 (br s, 4H), 2.15 (s, 3H), 1.34 (d, J=6.8 Hz, 3H). MS (ESI), m/z: 525 (M$^+$+H$^+$).

Example 38—(R)-4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide (D2200)

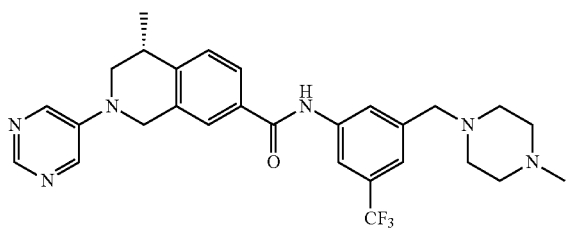

The compound was synthesized by using the procedure similar to that of Example 1. $^1$H NMR (400 MHz, DMSO-$d_6$) δ 10.50 (s, 1H), 8.60-8.55 (m, 3H), 8.19 (s, 1H), 8.00 (s, 1H), 7.86-7.84 (m, 2H), 7.47 (d, J=8.0 Hz, 1H), 7.35 (s, 1H), 4.65 (d, J=16.0 Hz, 1H), 4.53 (d, J=16.0 Hz, 1H), 3.66 (dd, J=12.4, 4.4 Hz, 1H), 3.54 (s, 2H), 3.47 (dd, J=12.4, 6.0 Hz, 1H), 3.19-3.18 (m, 1H), 2.39 (br s, 4H), 2.34 (br s, 4H), 2.15 (s, 3H), 1.34 (d, J=6.8 Hz, 3H). MS (ESI), m/z: 525 (M$^+$+H$^+$).

Example 39—(S)—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide (D2100)

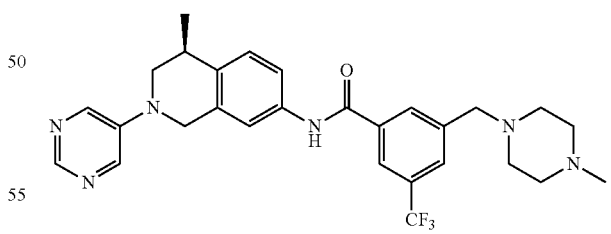

The compound was synthesized by using the procedure similar to that of Example 2. $^1$H NMR (400 MHz, DMSO-$d_6$) δ 10.45 (s, 1H), 8.57 (s, 2H), 8.55 (s, 1H), 8.19 (s, 1H), 8.17 (s, 1H), 7.85 (s, 1H), 7.69 (s, 1H), 7.58 (d, J=8.4 Hz, 1H), 7.30 (d, J=8.4 Hz, 1H), 4.55 (d, J=16.0 Hz, 1H), 4.45 (d, J=16.0 Hz, 1H), 3.68-3.60 (m, 3H), 3.43-3.38 (m, 1H), 3.08 (m, 1H), 2.41 (br s, 4H), 2.33 (br s, 4H), 2.15 (s, 3H), 1.30 (d, J=6.8 Hz, 3H). MS (ESI), m/z: 525 (M$^+$+H$^+$).

Example 40—(R)—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide (D2164)

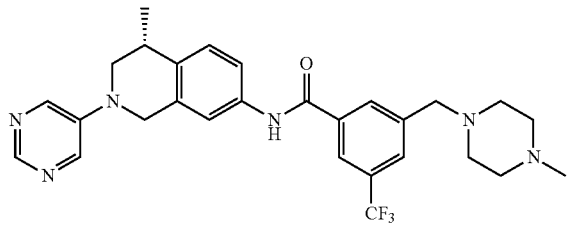 [SMILES: C[C@H]1CN(c2cncnc2)Cc2cc(NC(=O)c3cc(CN4CCN(C)CC4)cc(C(F)(F)F)c3)ccc21]

The compound was synthesized by using the procedure similar to that of Example 2. $^1$H NMR (400 MHz, DMSO-$d_6$) δ 10.44 (s, 1H), 8.57 (s, 2H), 8.55 (s, 1H), 8.19 (s, 1H), 8.17 (s, 1H), 7.84 (s, 1H), 7.69 (s, 1H), 7.58 (d, J=8.0 Hz, 1H), 7.29 (d, J=8.0 Hz, 1H), 4.55 (d, J=16.0 Hz, 1H), 4.45 (d, J=16.0 Hz, 1H), 3.68-3.59 (m, 3H), 3.42-3.38 (m, 1H), 3.08-3.07 (m, 1H), 2.41 (br s, 4H), 2.33 (br s, 4H), 2.15 (s, 3H), 1.30 (d, J=6.8 Hz, 3H). MS (ESI), m/z: 525 (M$^+$+H$^+$).

Example 41—In Vitro Kinase Assay

The effects of compounds on the kinases DDR1 and DDR2 were assessed by using a Lantha Screen Eu kinase activity assay technology (Invitrogen, USA). Kinase reactions are performed in a 10 μL volume in low-volume 384-well plates. The kinases in reaction buffer consist of 50 mM HEPES pH 7.5, 0.01% BRU-35, 10 mM MgCl2, and 1 mM EGTA, the concentration of Fluorescein-Poly GAT substrate (Invitrogen, USA) in the assay is 100 nM. Kinase reactions were initiated with the addition of 100 nM ATP in the presence of serials of dilutions of compounds. The reactions were allowed to proceed for 1 h at room temperature before a 10 μL preparation of EDTA (20 mM) and Eu-labeled antibody (4 nM) in TR-FRET dilution buffer are added. The final concentration of antibody in the assay well is 2 nM, and the final concentration of EDTA is 10 mM. The plate is allowed to incubate at room temperature for one more hour before the TR-FRET emission ratios of 665 nm/340 nm were acquired on a PerkinElmer EnVision multilabel reader (Perkin-Elmer, Inc.). Data analysis and curve fitting were performed using GraphPad Prism4 software, resulting in the half maximal inhibitory concentration (IC$_{50}$) shown in table 1. The functional assays of compounds on the kinase activities of c-kit and Abl were determined using the FRET-based Z'-Lyte assay system according to the manufacturer's instructions (Invitrogen, USA). Tyrosine 2 peptide was used as Abl substrate, and Ser/Thr 6 peptide was used as the substrate for c-kit. The reactions were carried out in 384-well plates in a 10 μL of reaction volume with appropriate amount of kinases in 50 mM HEPES (pH 7.5), 10 Mm MgCl$_2$, 1 mM EGTA, and 0.01% Brij-35. The reactions were incubated 1 h at room temperature in the presence of 2 μM of substrate with 10 μM of ATP (for Abl1 assays) or 300 μM of ATP (kit assay) and in the presence of various concentrations of the compounds. The development reagent was then added for further 2 h room temperature incubation followed by the addition of stop solution. Fluorescence signal ratio of 445 nm (Coumarin)/520 nm (fluorescin) was examined on EnVision Multilabel Reader (Perkin-Elmer, Inc.), resulting in the half maximal inhibitory concentration (IC$_{50}$) shown in Table 1.

Example 42—Materials and Methods

Cell Lines.

Human pancreatic cancer cell lines (AsPC-1 and Panc-1) were purchased from the American Type Culture Collection (Manassas, Va.) and were fingerprinted for validation of authenticity. The murine pancreatic cancer cell line Pan02 (also known as Panc02) was obtained from the NCI (DCTD Tumor Repository). Cells were cultured in DMEM (Invitrogen) or RPMI (Invitrogen) containing 5% fetal bovine serum and maintained at 37° C. in a humidified incubator with 5% CO$_2$ and 95% air.

In Vitro Cytotoxicity and Drug Response Assay.

MTS assays were conducted in 96-well plates; cells were plated on day 0 and drug was added on day 1 in 4-fold dilutions. Drugs were evaluated as single agents with a maximum concentration of 2 μM for gemcitabine and 7rh. For combination studies 7rh was added with a fixed concentration of 250 or 500 nM with a 4-fold dilution of gemcitabine. Relative cell number was determined by adding MTS (Promega; final concentration 333 μg/mL), incubating for 1 to 3 hours at 37° C., and reading absorbance. Drug sensitivity curves and IC$_{50}$s were calculated using in-house software (Apte et al., 2004).

Wound Healing (Scratch) Assay.

Cells were cultured in 6-well tissue culture plates at high density (~90% confluence) in 2 mL 5% DMEM or 5% RPMI. Uniform scratches were made down the center of each well with a p20 pipette tip. Cells were plated on respective culture conditions and allowed to sit for approximately 30 hours, or until end of possible migration. Images from the center of each well were taken at times 0, 10, 20, and 30 hours. The wound width (μm) was measured using NIS Elements AR 2.30 software. The initial wound width was used to verify consistency in scratches.

Liquid Colony Forming Assay.

Cells were cultured in 6-well tissue culture plates at low density (250 cells per well) in 2 ml 5% DMEM or 5% RPMI. Cells were plated on respective culture conditions and allowed to sit for approximately 1.5-2 weeks, or until significant colony formation. Cells were then fixed with 10% formalin and stained with crystal violet. Images were analyzed with Image J or NIS Elements.

Western Blot Analysis.

Sub-confluent monolayers of cells were lysed, supernatants were recovered by centrifugation at 13000 rpm, protein concentrations were measured and equal amounts of total protein were separated by SDS-PAGE. Proteins were transferred to PVDF membranes (Bio-Rad, Hercules, Calif.) followed by blockade for 1 hour in 5% milk in TBS-T. The membranes were incubated overnight at 4° C. with primary antibody. Membranes were incubated with the corresponding HRP-conjugated secondary antibody (Pierce Biotechnologies, Rockford, Ill.) for 1 to 2 hour. Specific bands were detected using the enhanced chemiluminescence reagent (ECL, Perkin Elmer Life Sciences, Boston, Mass.) on autoradiographic film.

Immunoprecipitation.

Cell lines were lysed in modified radioimmunoprecipitation (RIPA) assay buffer (0.5% deoxycholate, 0.5% SDS, 1% Triton X-100, 10 mM sodium phosphate, pH 7.2, 150 mM sodium chloride, and protease inhibitor (Complete Mini)). Lysis was performed on serum-starved adherent cells after washing with chilled PBS. Lysates were allowed to rotate at 4° C. on a nutator for 1 h and then vortexed several times before centrifuging at 13,000 rpm for 10 min to pellet any insoluble material. Lysates were pre-cleared with protein A/G beads (Thermo Fisher Scientific). 200 µg cellular protein in 1 ml lysis buffer was used per immunoprecipitation reaction. 1 µg of the appropriate IgG was added with 50 µl protein A/G bead slurry to each sample; each sample was then allowed to rotate overnight at 4° C. on a nutator. Immunoprecipitated complexes were washed twice in lysis buffer and then boiled in sample buffer and subjected to SDS-PAGE and Western blot analysis.

siRNA-Mediated Knockdown of DDR1.

Cells were plated 18-24 hours before transfection (1×10$^5$ cell/well in 6 well dish) at an initial confluence of 60-80%. TransIT-siQUEST reagent and siRNA complexes were prepared and added according to manufacturer instructions (Mims Bio LLC). siRNA complexes were added to the cells at a final siRNA complex concentration was 1 µM. Protein was harvested 72 hours post transfection for western blot analysis. siRNA duplexes were purchased from Integrated DNA Technologies. DDR1 duplexes used were (NM_001954 duplexes 1-3):

```
Duplex #1:
5'-GUCUUGUAGCUAGAACUUCUCUAAG-3',   (SEQ ID NO: 1)

3'-GUCAGAACAUCGAUCUUGAAGAGAUUC-5'; (SEQ ID NO: 2)

Duplex #2:
5'-GCACUAGGCAGGUAAUAAUAAAGGT-3',   (SEQ ID NO: 3)

3'-GACGUGAUCCGUCCAUUAUUAUUUCCA-5'; (SEQ ID NO: 4)

Duplex #3:
5'-ACACUAAUAUAUGGACCUAGAUUGA-3',   (SEQ ID NO: 5)

3'-AAUGUGAUUAUAUACCUGGAUCGAACU-5'. (SEQ ID NO: 6)
```

RNA Isolation/Purification and RT-PCR.

RNA was isolated from cell line pellets utilizing TRIzol® (Invitrogen) reagent according to the manufacturer's protocol. The samples were then eluted in RNAse/DNAse free water and utilized for subsequent cDNA synthesis. Purified RNA was reverse transcribed into cDNA using the iScript™ cDNA synthesis kit (Bio-Rad, Hercules, Calif.). The following human primer sets were used for RT-PCR:

```
                                   (SEQ ID NO: 7)
DDR1-FWD:        CCTCTTTGCAGGTCCTTGGTT, (SEQ ID NO: 8)
DDR1-REV:        AGCTCCAAGCTGCTGAAGTTG;

(SEQ ID NO: 9)
DDR2-FWD:        AAGCTGGGAGAAGGCCAGTT, (SEQ ID NO: 10)
DDR2-REV:        AGGCTGGTTGGCACTGACAT;

(SEQ ID NO: 11)
Col1α1-FWD:      GACGCCATCAAGGTCTACTG;

(SEQ ID NO: 12)
Col1α1-REV:      ACGGGAATCCATCGGTCA;

(SEQ ID NO: 13)
Col1α2-FWD:      GGAGGGAACGGTCCACGAT;

(SEQ ID NO: 14)
Col1α2-REV:      GAGTCCGCGGTATCCACAA;

(SEQ ID NO: 15)
Itg α1-FWD:      TGGGTGCTTATTGGTTCTCC;

(SEQ ID NO: 16)
Itg α1-REV:      CCTCCTTTCTTGCTGTGTCTAT;

(SEQ ID NO: 17)
Itg β1-FWD:      GAAGCTCAAGCCAGAGGATATT;

(SEQ ID NO: 18)
Itg β1-REV:      CTGGACAAGGTGAGCAATAGAA;

(SEQ ID NO: 19)
PEAK1-FWD:       GTTGGAGTAGCCTCCCATTATC;

(SEQ ID NO: 20)
PEAK1-REV:       GACGCTTAGTAGGACCCAAAG;

(SEQ ID NO: 21)
RPS6-FWD:        GAGCGTTCTCAACTTGGTTATTG;

(SEQ ID NO: 22)
RPS6-REV:        GTGCTTTGGTCCTAGGTTTCT.
```

Animal Studies.

All animals were housed in pathogen-free facility with access to food and water ad libitum. C57BL/6 and NOD-SCID mice were purchased from an on-site distributor. Kras$^{G12D/+}$; LSL-Trp53$^{R172H/+}$; p48$^{Cre/+}$ (KPC) mice were generated as previously described (Hingorani et al., 2005). Mice were randomized to receive treatment as indicated in Table 1. Experiments were approved and performed in accordance with the Institutional Animal Care and Use Committee at the University of Texas Southwestern Medical Center. For endpoint studies experiments were stopped after the designated time post-tumor cell implantation. For survival studies, therapy was maintained until mice were moribund. At the time of sacrifice all mice were subjected to careful necropsy where visible metastases were noted and organs harvested for tissue analysis. Liver micrometastasis was assessed by hemotoxylin and eosin staining of the anterior lobes of the liver.

TABLE 1

| Description of animal experiments | | |
|---|---|---|
| Endpoint: 7rh titration | Experiment start | 10 days post tumor cell injection |
| | Experiment length | 12 hours |
| | Animals | C57BL/6, (n = 3/group) |
| | Treatment groups | Vehicle: 1 dose |
| | | 7rh: 0.1 mg/kg, 1 dose |
| | | 7rh: 1 mg/kg, 1 dose |
| | | 7rh: 10 mg/kg, 1 dose |
| | Associated figures | FIG. 7 |
| Endpoint: 7rh titration | Experiment start | 10 days post tumor cell injection |
| | Experiment length | 21 days post tumor cell injection |
| | Animals | C57BL/6, (n = 5/group) |
| | Treatment groups | Vehicle: 3×/week |

TABLE 1-continued

| | | |
|---|---|---|
| | | 7rh: 3.3 mg/kg, 3×/week |
| | | 7rh: 10 mg/kg, 3×/week |
| | | 7rh: 30 mg/kg, 3×/week |
| | Associated figures | FIGS. 8 & 9 |
| Endpoint: | Experiment start | 19 days post tumor cell injection |
| 7rh monotherapy | Experiment length | 40 days post tumor cell injection |
| | Animals | C57BL/6, (n = 16/group) |
| | Treatment groups | Vehicle: 3×/week |
| | | 7rh: 25 mg/kg, 3×/week |
| | Associated figures | FIG. 10 |
| Survival: | Experiment start | 27 days post tumor cell injection |
| 7rh +/− chemo | Experiment length | Until moribund |
| | Animals | Nod Scid, (n = 12/group) |
| | Treatment groups | Vehicle: 3×/week |
| | | 7rh: 25 mg/kg, 3×/week |
| | | Chemotherapy: Gem (12.5 mg/kg, 2×/week), Nab-pac (5 mg/kg, 2×/week) |
| | | Combination: 7rh + Chemotherapy |
| | Associated figures | FIGS. 11 & 12 |
| Survival: | Experiment start | 16 weeks old |
| 7rh +/− chemo | Experiment length | Until moribund |
| | Animals | KPC (LSL-Kras$^{G12D/+}$; LSL-Trp53$^{R172H/+}$; P48-Cre), (n = 12/group) |
| | Treatment groups | Vehicle: 3×/week |
| | | 7rh: 25 mg/kg, 3×/week |
| | | Chemotherapy: Gem (12.5 mg/kg, 2×/week), Nab-pac (5 mg/kg, 2×/week) |
| | | Combination: 7rh + Chemotherapy |
| | Associated figures | FIGS. 13 & 14 |

* Gem is gemcitabine; Nab-pac is nab-paclitaxel.

Histology.

Immunohistochemistry was performed with antibodies against: phospho-DDR1 (Tyr792, Cell Signaling #11994), DDR1 (D1G6, Cell Signaling #5583), phospho-SRC (Tyr416, Cell Signaling #2101), phospho-PYK2 (Tyr402, Cell Signaling #3291), phospho-p130 CAS (Tyr165, Cell Signaling #4015), α-Amylase (D55H10, Cell Signaling #3796), vimentin (Millipore AB5733), phospho-FAK (Abcam #4803), activated β1 Integrin (Millipore #2079Z), PEAK1 (Millipore 09-274) and phospho-PEAK1 (Tyr665, Millipore #ABT52). Fluorescent images were captured with Photometric Coolsnap HQ camera using NIS Elements AR 2.3 Software (Nikon). Color images were obtained with a Nikon Eclipse E600 microscope using a Nikon Digital Dx1200me camera and ACT1 software (Universal Imaging Corporation). Pictures were analyzed using NIS Elements (Nikon).

Statistical Analysis.

Quantification of immunohistochemistry was conducted using NIS Elements 3.2 software (Nikon Instruments). All data were analyzed using GraphPad Prism 5.0 software (GraphPad Software Inc.). Datasets were analyzed by Student t test or ANOVA followed by Dunn post test or Tukey's MCT and results were considered as significant at $p<0.05$. Results are shown as mean±SEM.

Example 43—Results

A. Association of DDR1 Signaling with Enhanced Malignancy

Figure 1A:
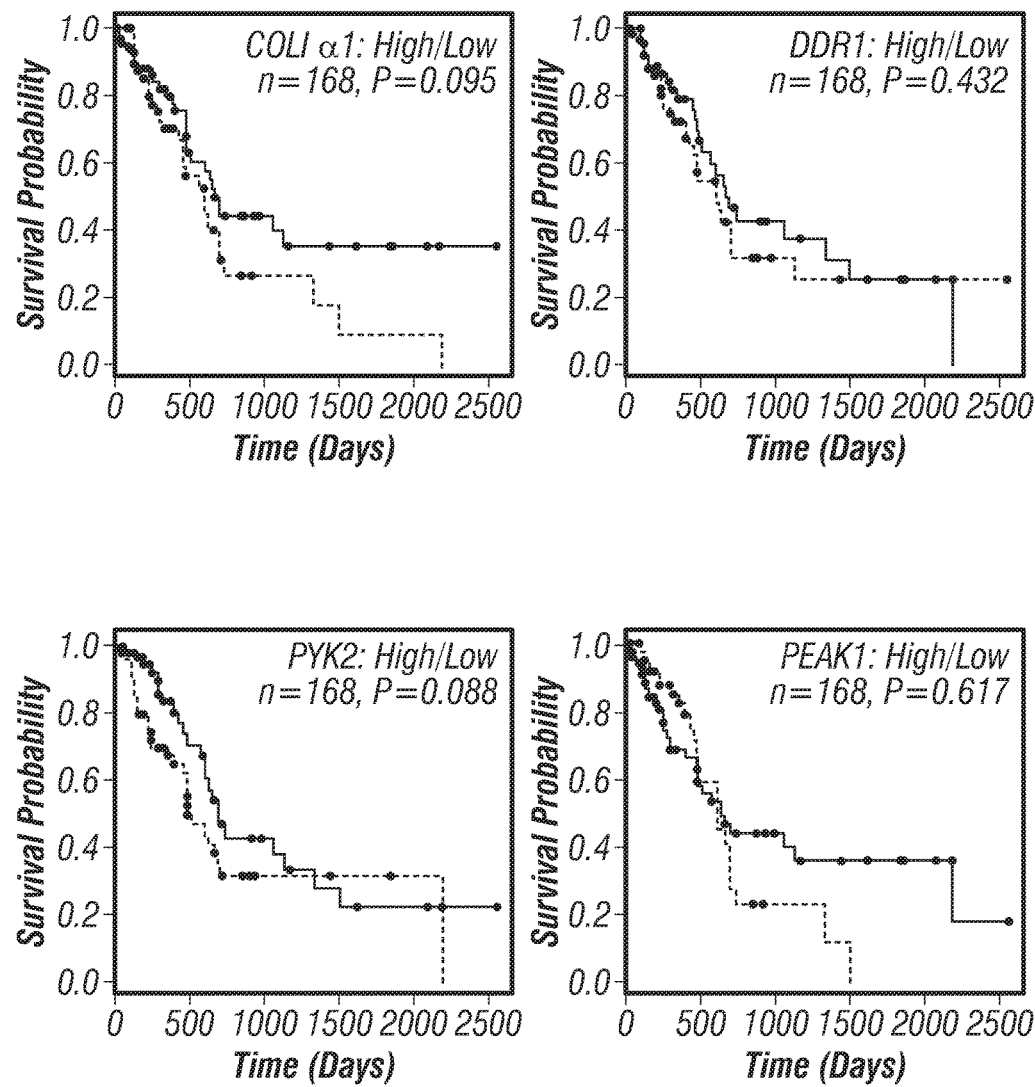
Figure 1B:
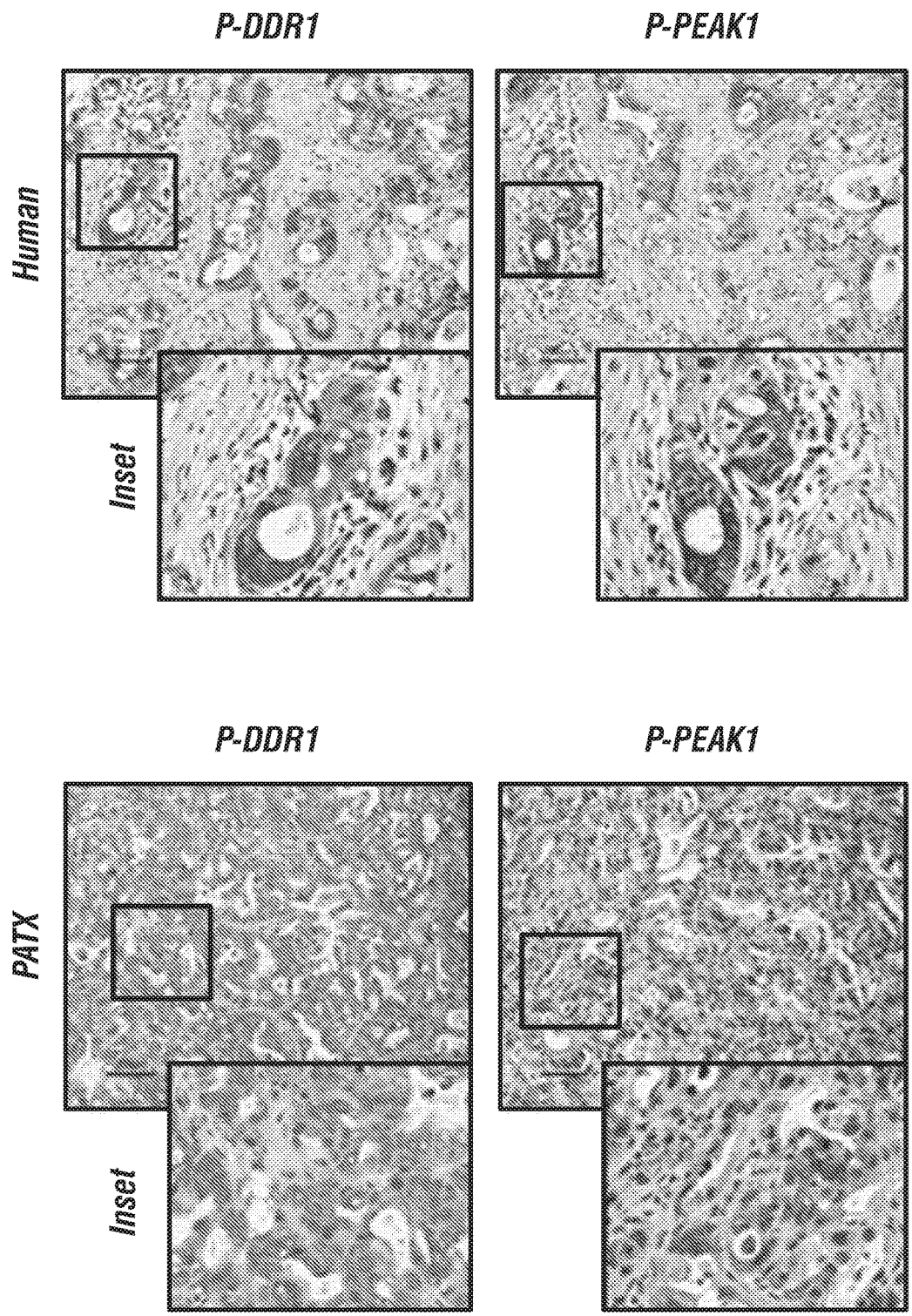
Figure 2A:
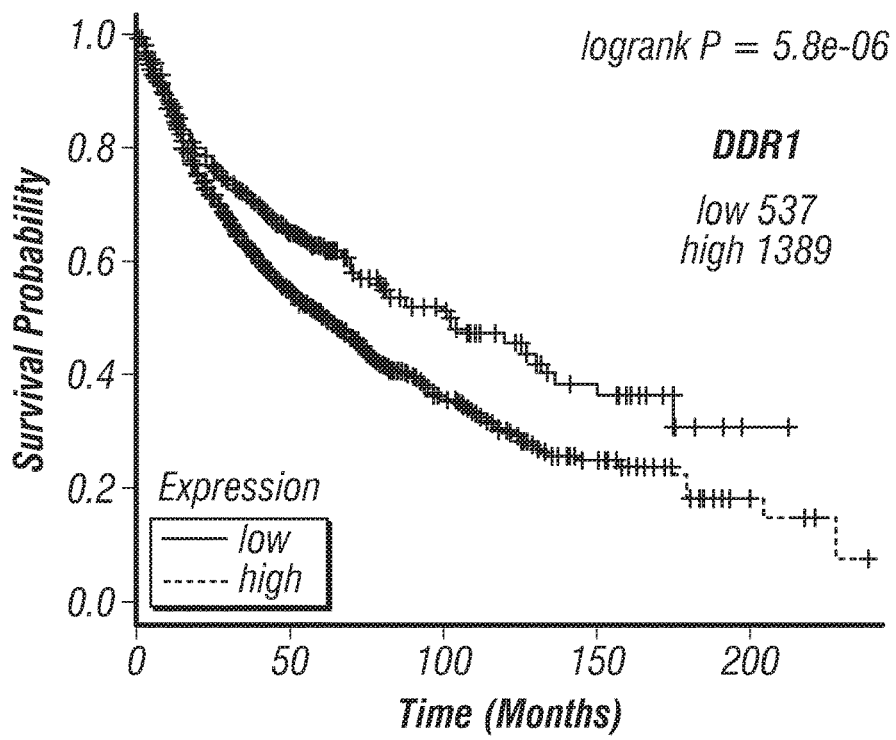
FIGS. 2A-C: DDR1 expression in lung cancer and PDA.
Figure 2A:
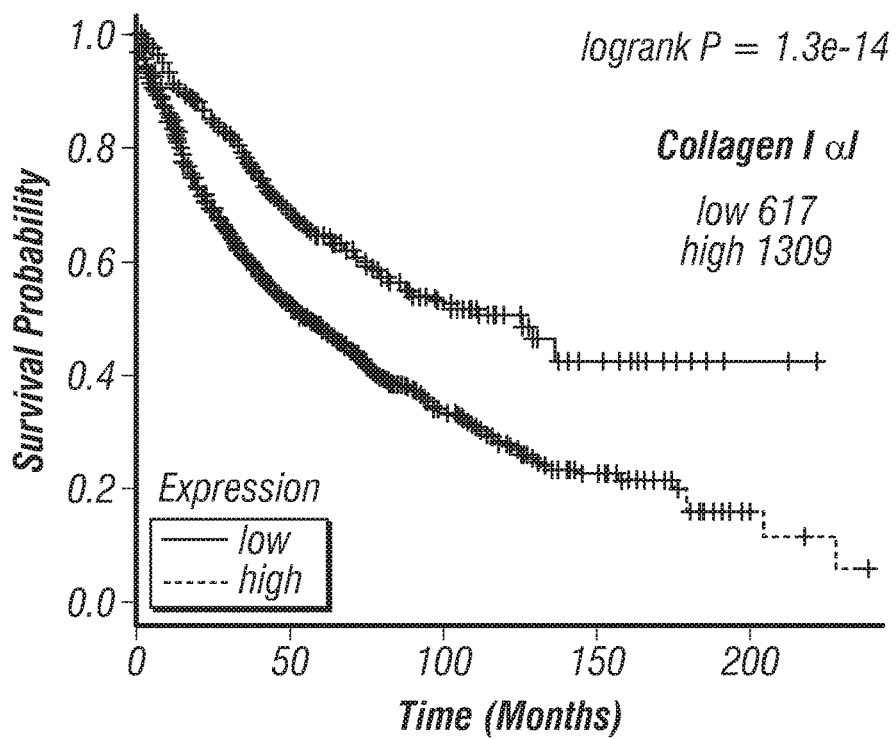
Figures 2B, 2C:
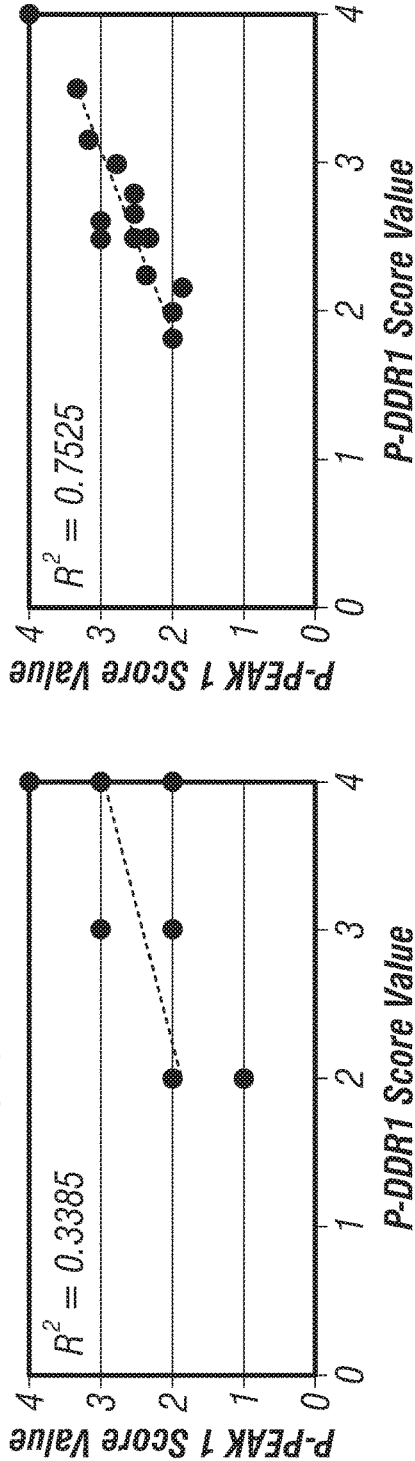

The mRNA expression of collagen I α1, DDR1, PYK2 and PEAK1 were analyzed in human PDA patients (n=168) in TCGA (via CBioportal). Expression was divided into high and low at the median (described in materials and methods). While there was no statistically significant difference in outcome (survival) with respect to expression of these targets at a 95% confidence interval, several notable trends were identified. PDAs with high expression of collagen I α1 or PEAK1 had a trend for worse overall survival (FIG. 1A). The mRNA expression of DDR1 and collagen I α1 in lung cancer was also evaluated using the Kaplan-Meier Plotter online database (Gyorffy et al., 2013). In lung cancer, expression of DDR1 and collagen I also correlated with worse survival (FIG. 2A). To characterize the level of collagen-mediated DDR1 signaling in PDA, the expression of phosphorylated DDR1 and a downstream effector (PEAK1) in human pancreatic tumor samples was determined with matched patient-derived tumor xenograft (PATX) samples. Primary tumors (44) and PATX samples (150) showed robust activation of DDR1 and PEAK1 (FIG. 1B, FIG. 2B). The overall percentages of staining positivity are shown in FIG. 2C. Furthermore, the expression of active Ddr1, Pyk2 and Peak1 as well as the expression of Mud 1 and Sox9 in pancreatic tumors was examined from early (3 month) and later (5 month) stages of the KPC (LSL-Kras$^{G12D/+}$; LSL-Trp53$^{R172H/+}$; p48$^{Cre/+}$) mouse model of PDA (FIG. 1C). The KPC model recapitulated many of the pathological features seen in human PDA including a dense stromal reaction (Hingorani et al., 2005) (FIGS. 1D & 1E). Trichrome analysis revealed robust collagen deposition throughout PDA lesions in KPC mice (FIG. 1E). Ddr1 activation and downstream signaling (Pyk2 and Peak1) was present in early pancreatic intraepithelial (PanIN) lesions as shown by correlative staining with a marker of early PDA lesions, Muc-1. Additionally, these effectors were expressed highly throughout the tumor epithelium at the later stage of the model (5-month old KPC) as identified by areas expressing Sox9 (FIG. 1C). Sox9 was expressed in the malignant epithelium and was confined to the duct-like cells; differentiated acinar and endocrine cells do not express Sox9

(Seymour et al., 2008 and Furuyama et al., 2011). These data demonstrated that collagen signaling via DDR1 is active in human PDA and mouse models of the disease.

The KPC model recapitulates many of the pathological features seen in human PDA including a dense stromal reaction (Hingorani et al., 2005) (FIGS. 3A-B). Trichrome analysis revealed robust collagen deposition throughout PDA lesions in KPC mice (FIGS. 3C-D). Histological analyses of metastatic lesions in the liver demonstrate that collagen is deposited in liver lesions. Further these lesions show activation of Ddr1 and Peak1 as well as vimentin and PCNA positive cells. (FIGS. 3G-H). These findings indicate that collagen signaling through Ddr1 is present in primary and metastatic PDA lesions and suggest that pharmacologic inhibition of Ddr1 could provide therapeutic benefit.

B. Regulation of Collagen Signaling

Figure 4C:
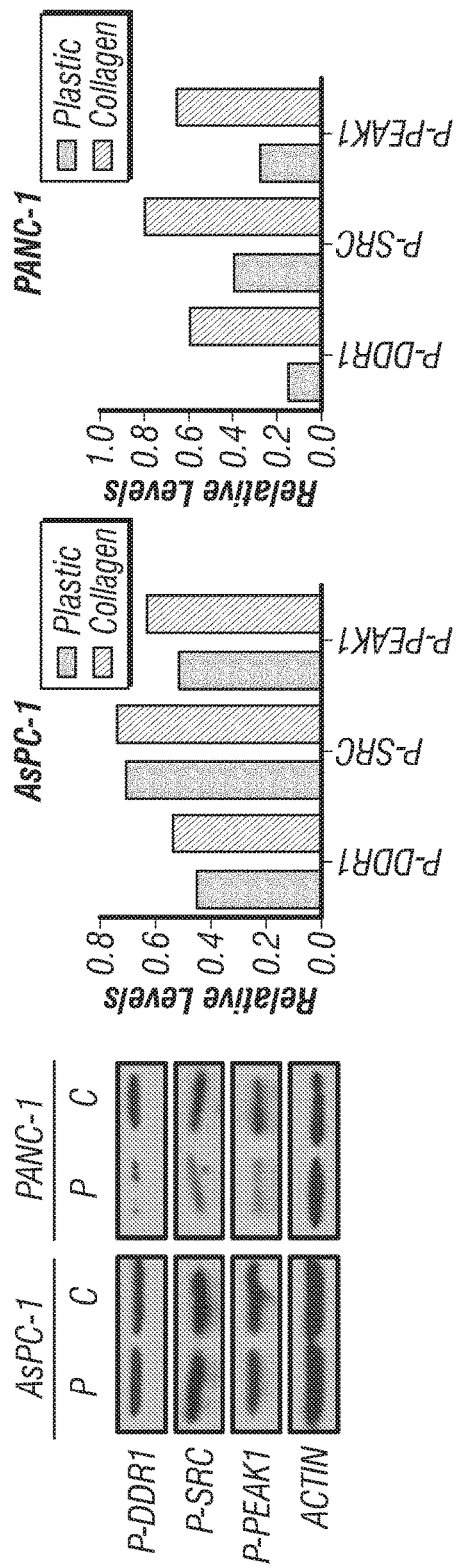
Figure 4D:
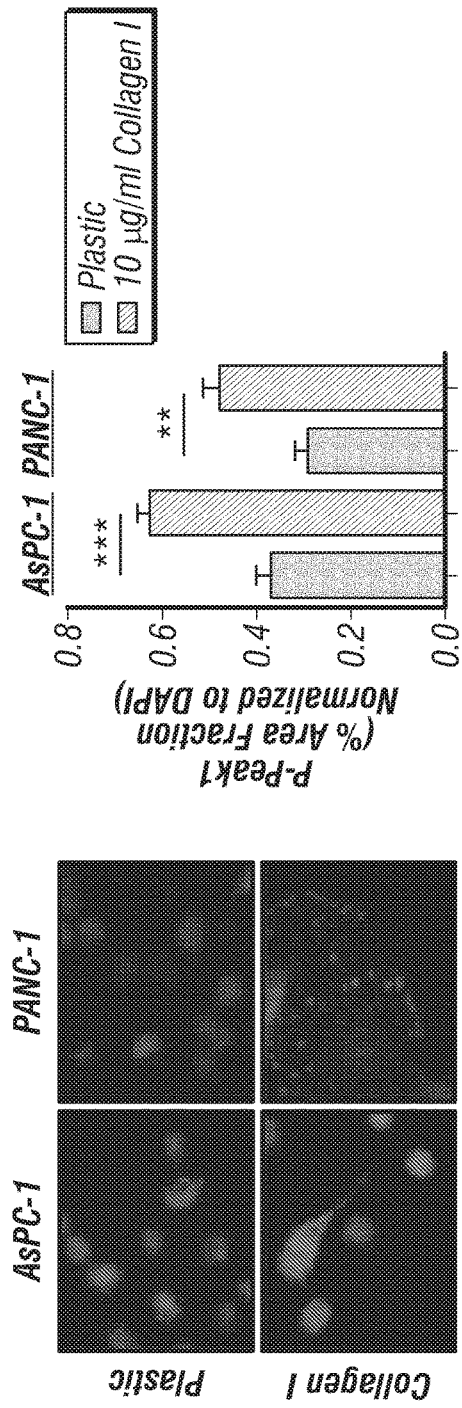
Figure 4E:
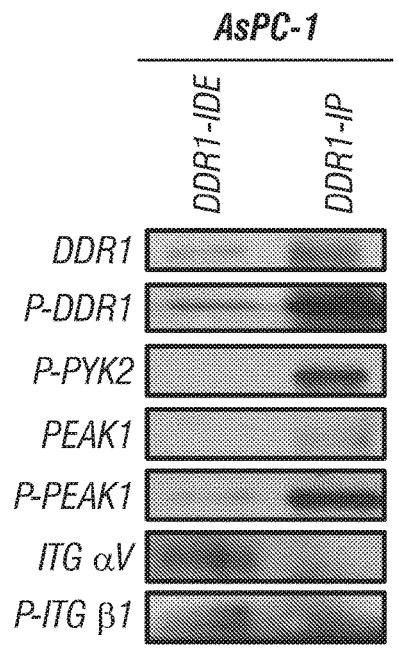
Figure 4F:
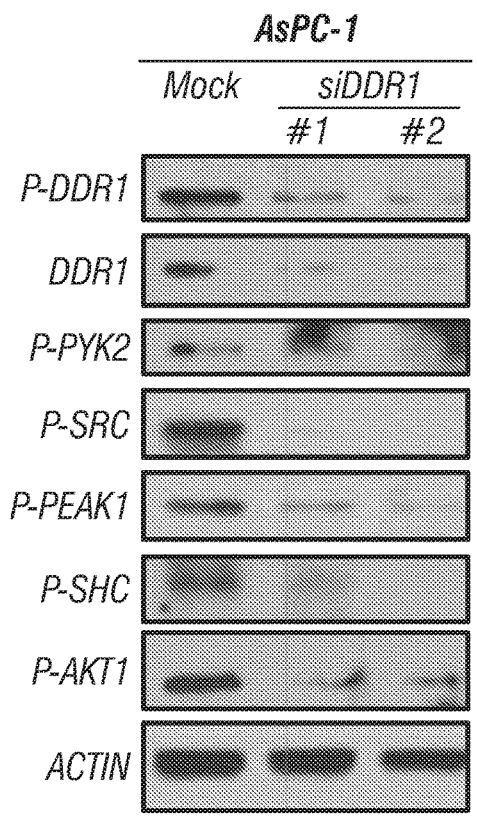
Figure 4G:
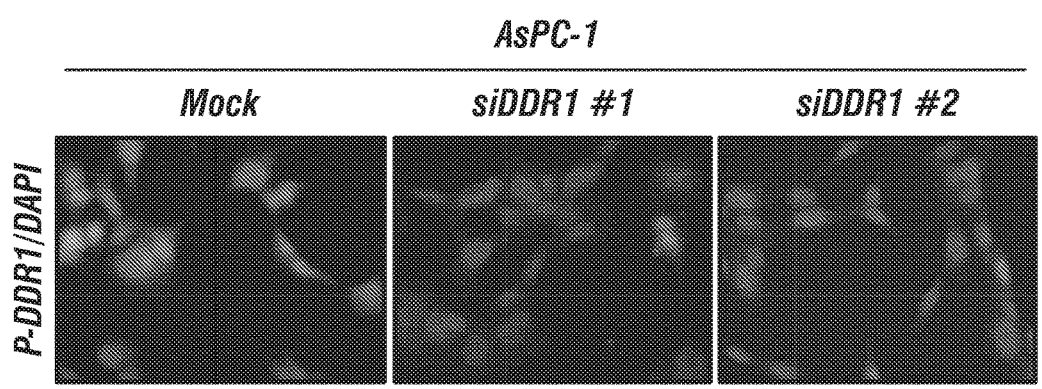
Figure 4H:
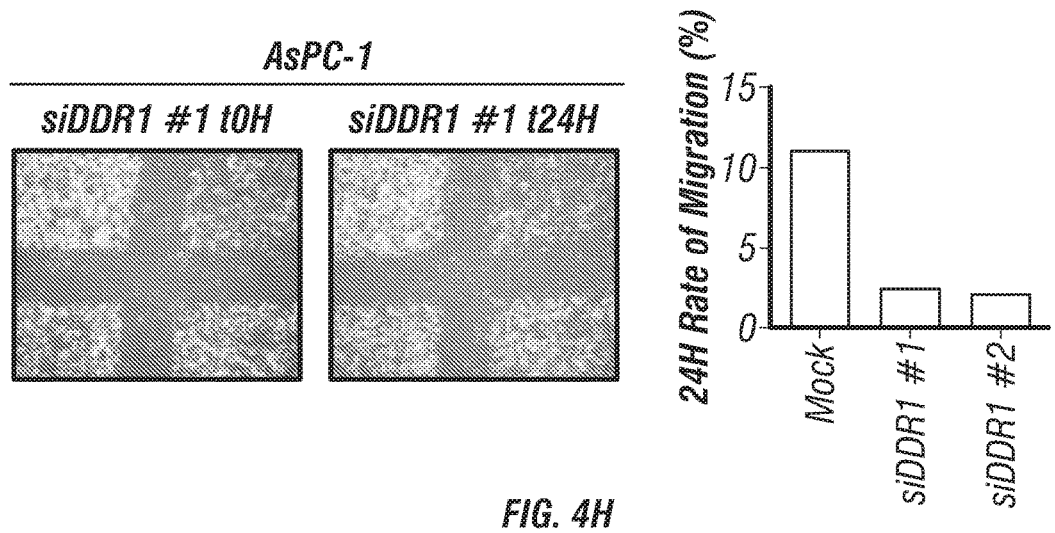

To determine if collagen signaling via DDR1 directly affects pancreatic cancer cell biology, the expression of genes involved in collagen signaling in human PDA cell lines (AsPC-1 and PANC-1) was determined by PCR. Each cell line expressed similar levels of DDR1, PEAK1, INTEGRIN α1 (ITG α1), INTEGRIN β1 (ITG β1) COLLAGEN I α1 (COL I α1), and COLLAGEN I α2 (COL I α2) (FIG. 4A). The level of collagen expressed by AsPC-1 and PANC-1 cells was determined by a Sircol assay (FIG. 4B) and confirmed that AsPC-1 cells expressed high levels of collagen. These results corresponded to the high endogenous activation of DDR1 (FIG. 4C) found in AsPC-1 cells. Addition of exogenous soluble collagen enhanced the phosphorylation of DDR1, SRC, and PEAK1 in PANC-1 cells but did not affect the level of DDR1 signaling in AsPC-1 cells (FIGS. 4C & 4D). Immunofluorescence was used to visualize DDR1 signaling in a cellular context. AsPC-1 and PANC-1 cells were plated on plastic or collagen and phosphorylated PEAK1 was assessed. In this context collagen stimulated PEAK1 activation in each cell line (FIG. 4D). The downstream effectors of DDR1 are ill-defined (Valiathan et al., 2012 and Leitinger, 2014); however, the phosphorylated PYK2 and PEAK1 was found to co-immunoprecipitated with DDR1 from AsPC-1 cells. The absence of integrin αv and β1 in the DDR1 IP suggested that DDR1 mediated activation of these effectors is independent of integrin activation (FIG. 4E). To further define the contribution of DDR1 to collagen signaling AsPC-1 cells were stimulated with collagen after siRNA-mediated knockdown of DDR1. Loss of DDR1 expression abrogated the activation of PYK, SRC, PEAK1 and AKT1 (FIG. 4F-4G), as well as cell migration (FIG. 4H). These data supported that collagen-mediated activation of DDR1 induced a signal pathway that included PYK2, SRC, PEAK1 and AKT1, which in turn are potentially responsible for collagen-induced pathways, including chemoresistance (Mahadevan and Von Hoff, 2007 and Chauhan et al., 2013), that promote tumor progression.

Figure 5A:
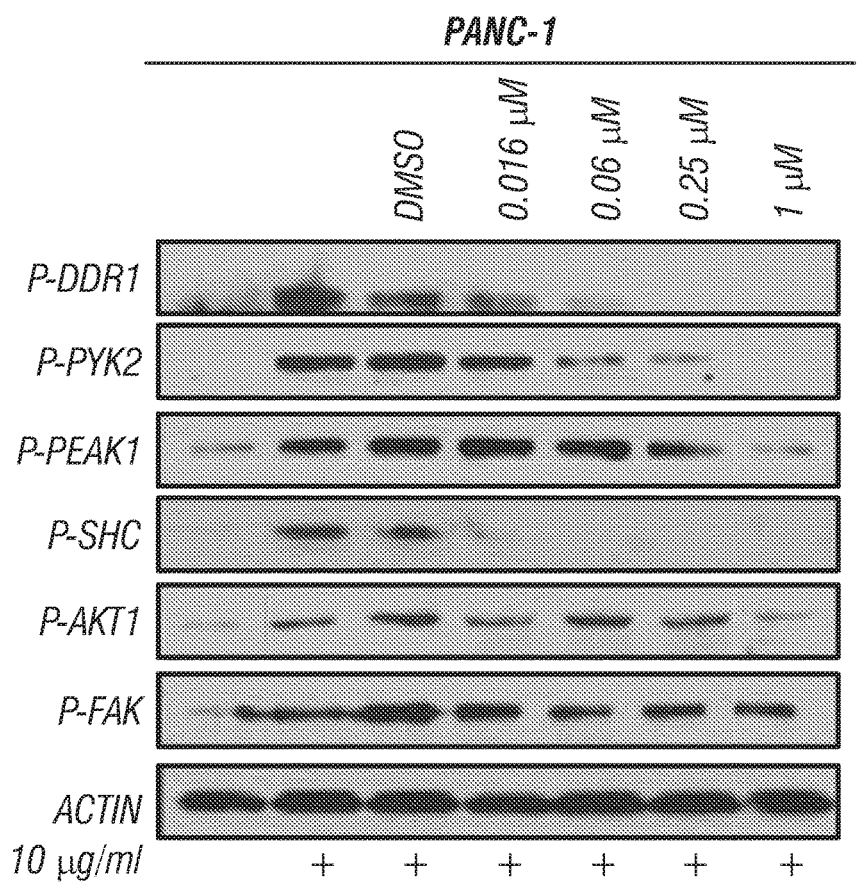
Figure 5C:
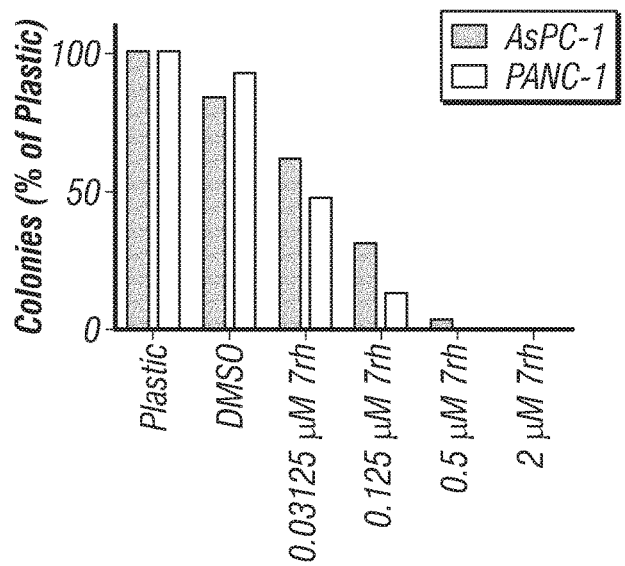
Figure 5D:
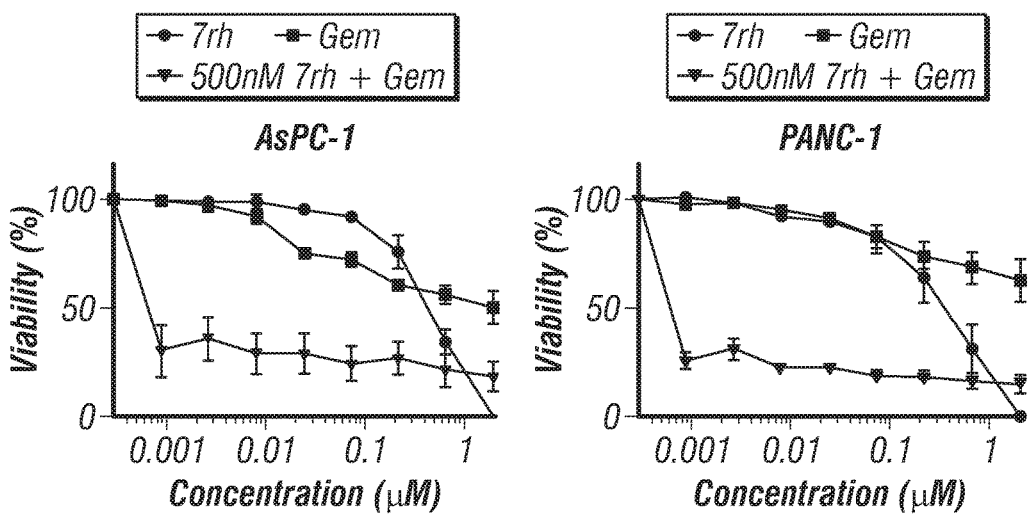

To demonstrate that DDR1 participates in chemoresponse in PDA the effect of the small molecule kinase inhibitor 3-(2-(Pyrazolo[1,5-a]pyrimidin-6-yl)-ethynyl) 7rh benzamide (7rh) (Gao et al., 2013) on collagen-induced signaling in PANC-1 cells was evaluated. 7rh has high specificity for DDR1 versus other related kinases ($IC_{50}$: DDR1, 6.8 nM; DDR2, 101.4 nM; Bcr-Abl, 355 nM) based on previously published cell-free kinase assays (Gao et al., 2013). 7rh inhibited DDR1-mediated signaling induced by soluble collagen (10 μg/mL) in PANC-1 cells in a concentration-dependent manner (FIG. 5A). At pharmacologically-relevant concentrations 7rh inhibited activation of PYK2, PEAK1, SHC, and AKT1. However, 7rh did not affect the activation of focal adhesion kinase (FAK), an effector that has not been previously associated with DDR1-induced signaling (Shintani et al., 2008). Inhibition of the DDR1 signaling with 7rh also reduced cell migration (FIG. 5B) and colony formation (FIG. 5C) in a concentration-dependent manner.

Figures 5D, 6:
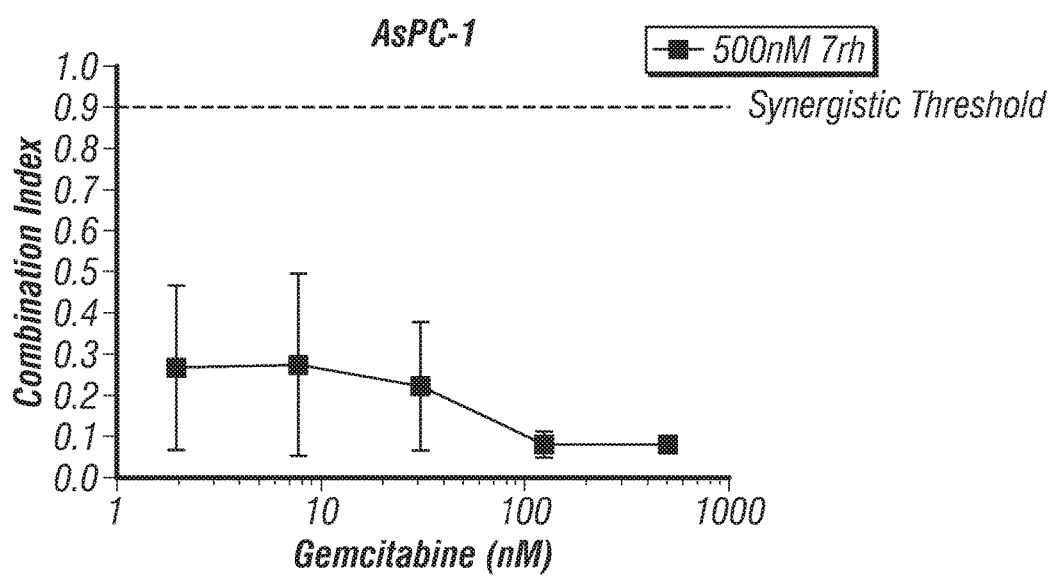
Figure 6:
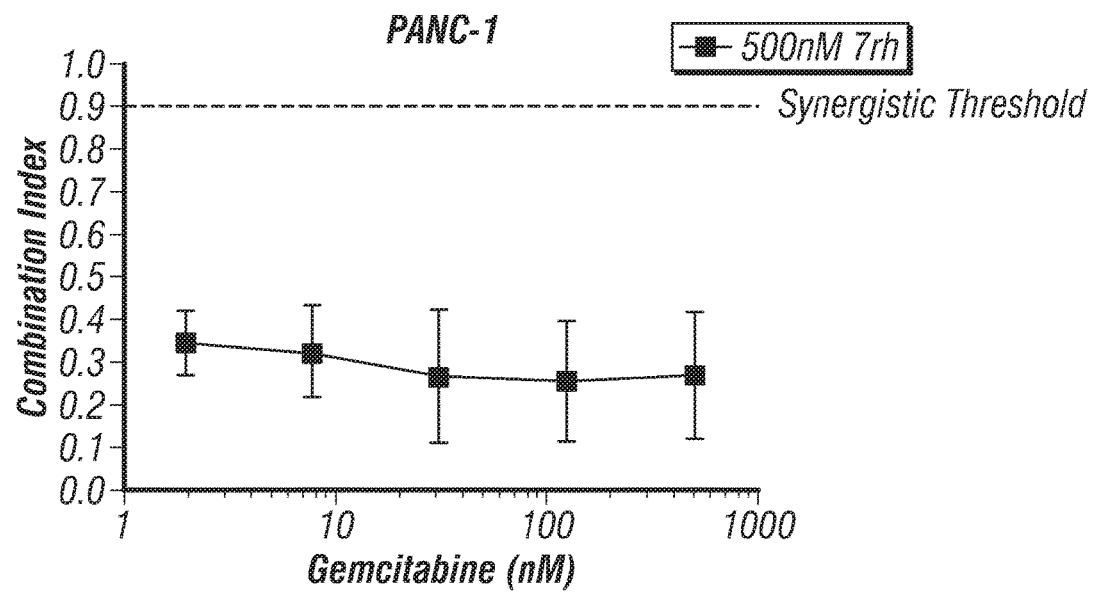
FIG. 6: Synergistic analysis of 7rh combined with gemcitabine. The combination index of 7rh (500 nM) with gemcitabine (2-2000 nM) was calculated via online CompuSyn Synergistical Analysis software (www.combosyn.com) (Chou, 2006). A combination index (CI) less than or equal to 0.9 is synergistic.
Figure 7A:
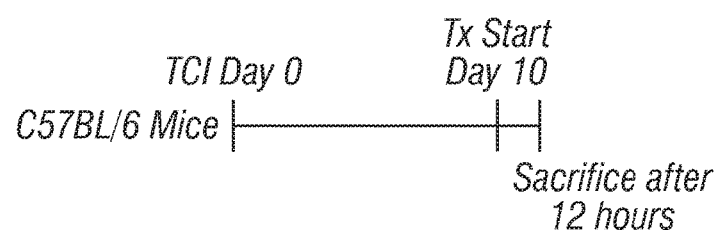
FIGS. 7A-E: 7rh reduces collagen-mediated signaling in a concentration-dependent manner in vivo.
Figure 7B:
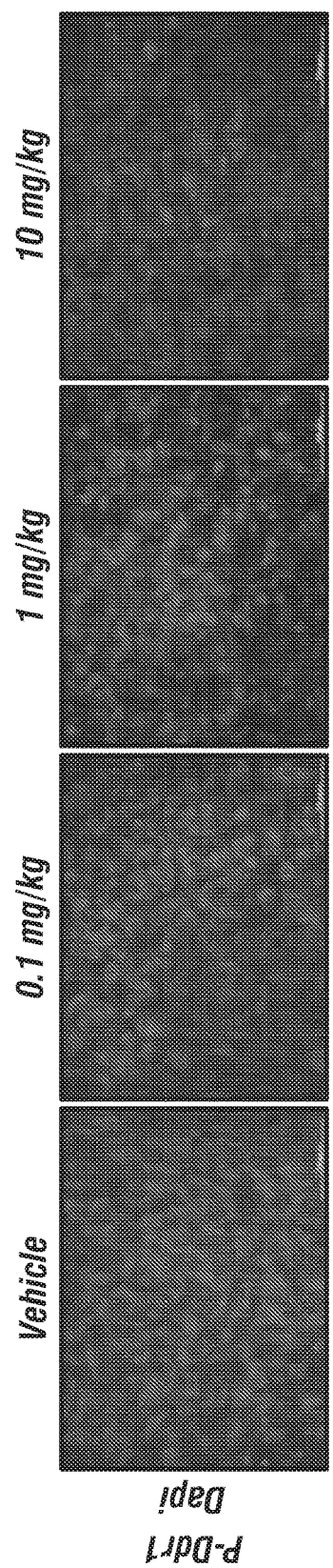
Figure 7C:
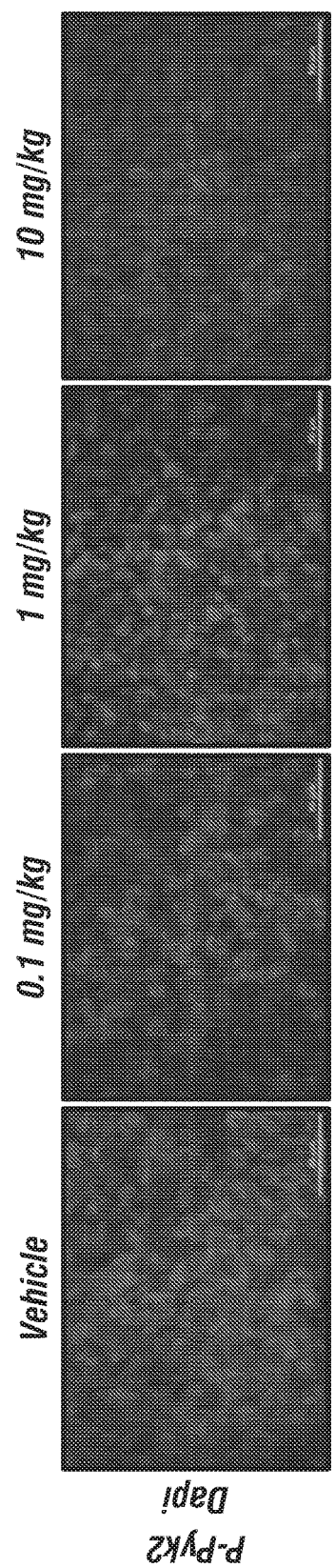
Figure 7D:
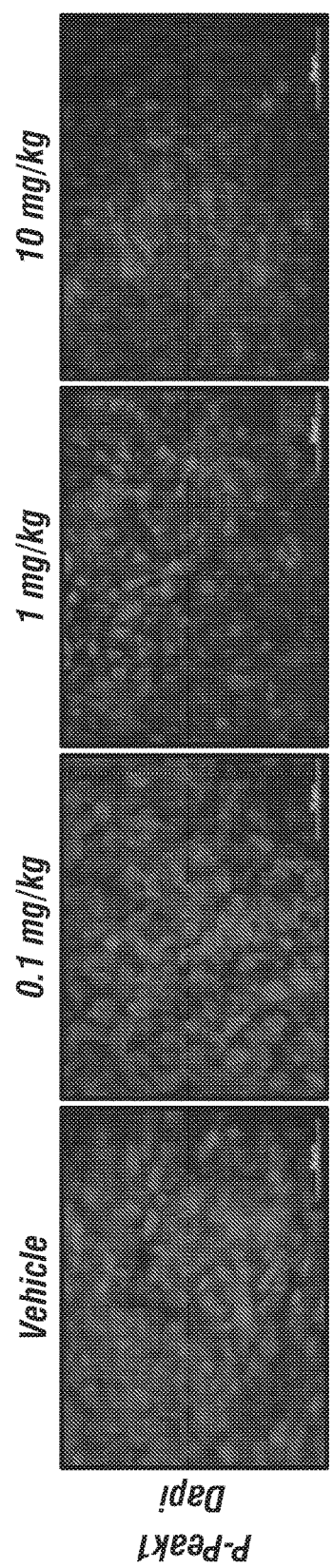
Figure 7E:
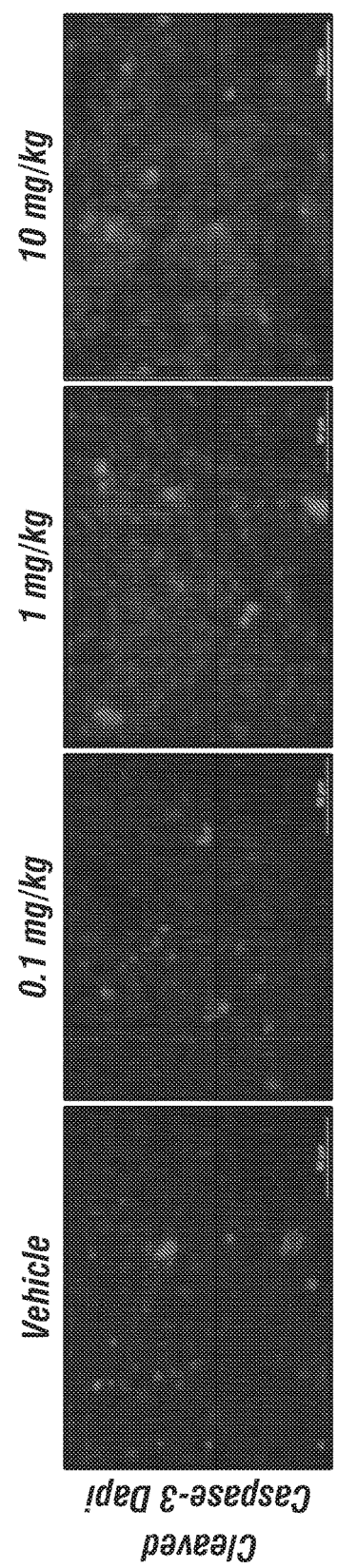
Figure 7E:
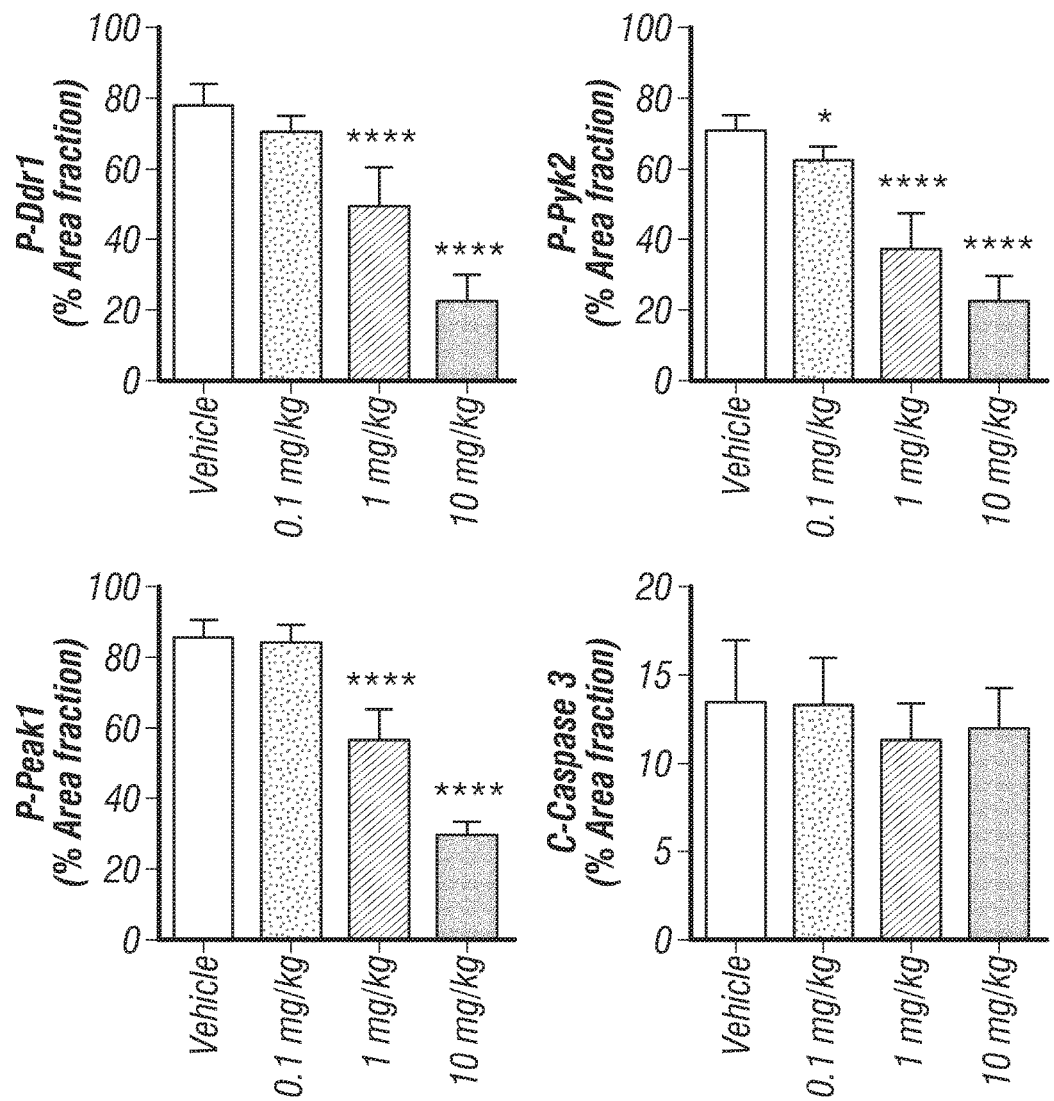

Chemoresistance is a major challenge in the treatment of patients with PDA. Given the effect of 7rh on PDA colony formation and migration the effect of 7rh in combination with gemcitabine, a chemotherapy agent commonly used for the treatment of PDA, was evaluated. The efficacy of 7rh alone or in combination with gemcitabine was tested by MTS assay in AsPC-1 and PANC-1 cells plated on plastic or collagen (Table 2). In cells plated on plastic, 7rh reduced cell viability with an $IC_{50}$ of 490 nM and 380 nM in AsPC-1 and PANC-1 cells, respectively. However, 7rh at 500 nM dramatically decreased the $IC_{50}$ of gemcitabine in each cell line from >2000 nM to 2 nM or less (FIG. 5D) strongly suggesting synergy between the two agents. Analysis with CompuSyn Synergistical Analysis software (Chou, 2006) indicated that 7rh at 500 nM was synergistic with gemcitabine in AsPC-1 and PANC-1 cells (FIG. 6). These findings highlight the therapeutic potential of DDR1 inhibition in combination with chemotherapy for PDA.

TABLE 2

Collagen shifts sensitivity of human PDA cell lines to therapeutic agents.

| Coating | 7rh (nM) | | Gemcitabine (nM) Avg $IC_{50}$s | | 250 nM 7rh + Gem Avg $IC_{50}$s | | 500 nM 7rh + Gem Avg $IC_{50}$s | |
|---|---|---|---|---|---|---|---|---|
| | Plastic (#) | Collagen (#) | Plastic (#) | Collagen (#) | Plastic (#) | Collagen (#) | Plastic (#) | Collagen (#) |
| ASPC-1 | 490 (6) | 550 (6) | 2000 (3) | 2000 (3) | 1725 (3) | 2000 (4) | 2.05 (2) | 2.7 (2) |
| PANC-1 | 380 (4) | 402 (4) | 2000 (4) | 2000 (3) | 16.4 (3) | 25.7 (3) | 0.035 (3) | 0.035 (3) |

C. 7rh Benzamide Inhibits Collagen-Mediated Signaling In Vivo

Figure 8A:
FIGS. 8A-G: 7rh inhibits Ddr1 activation in Pan02 tumors.
Figures 8B, 8C, 8D:
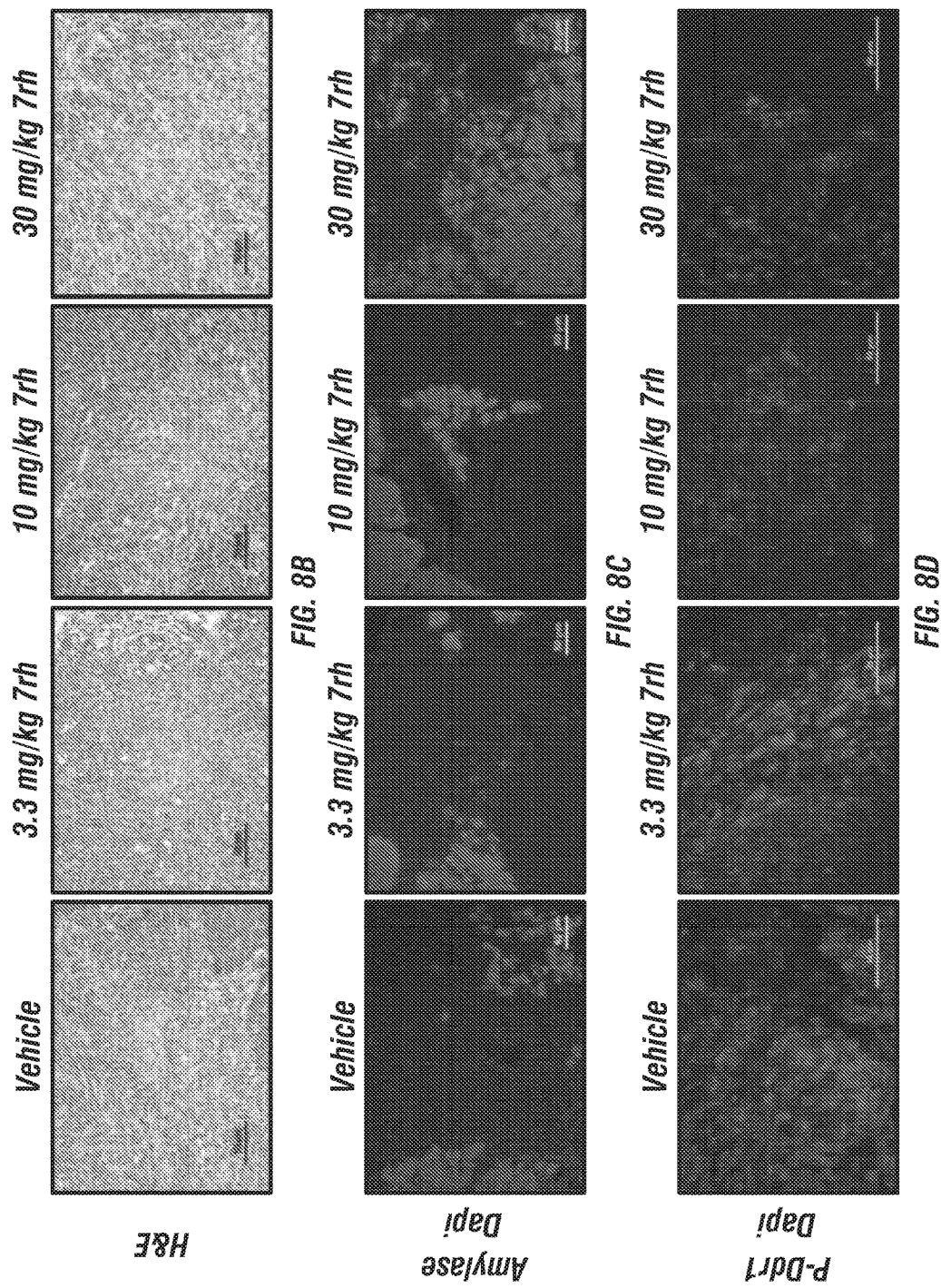
Figure 8E:
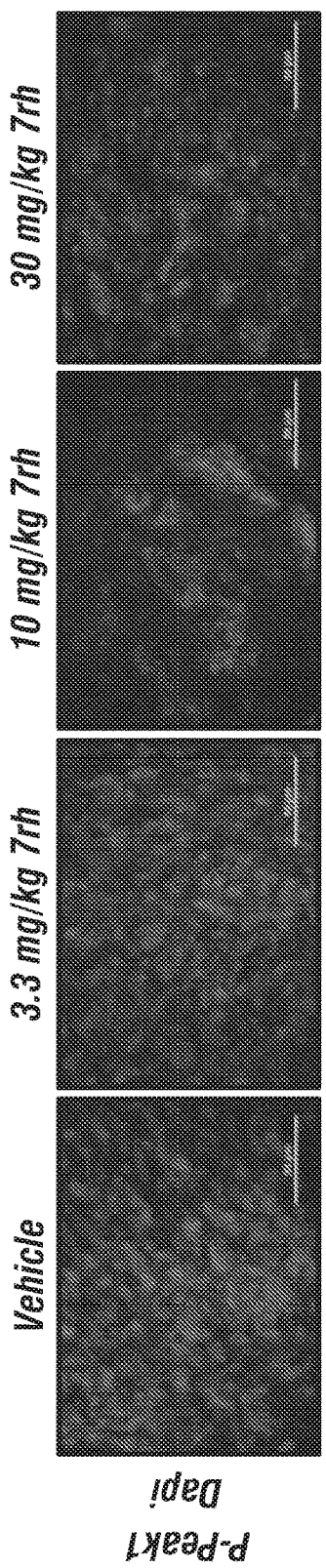
Figure 8F:
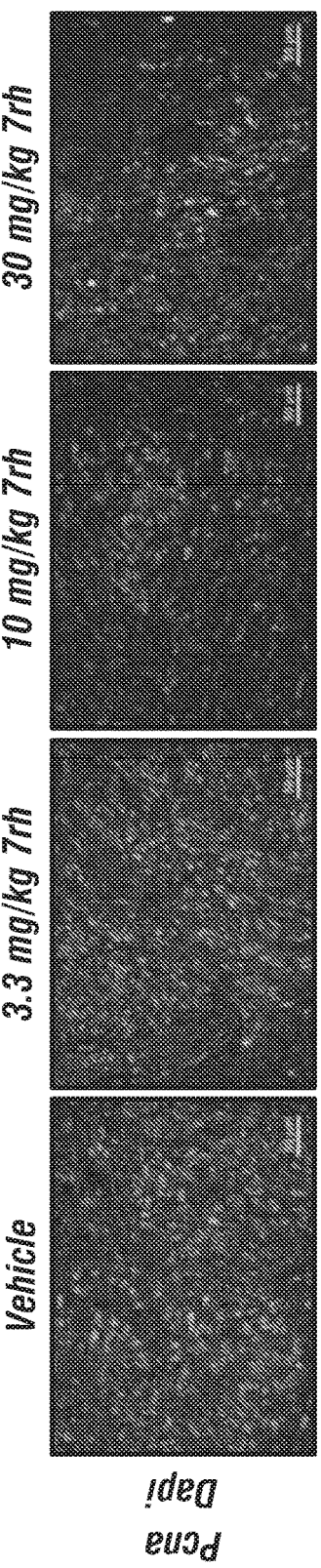
Figure 8F:
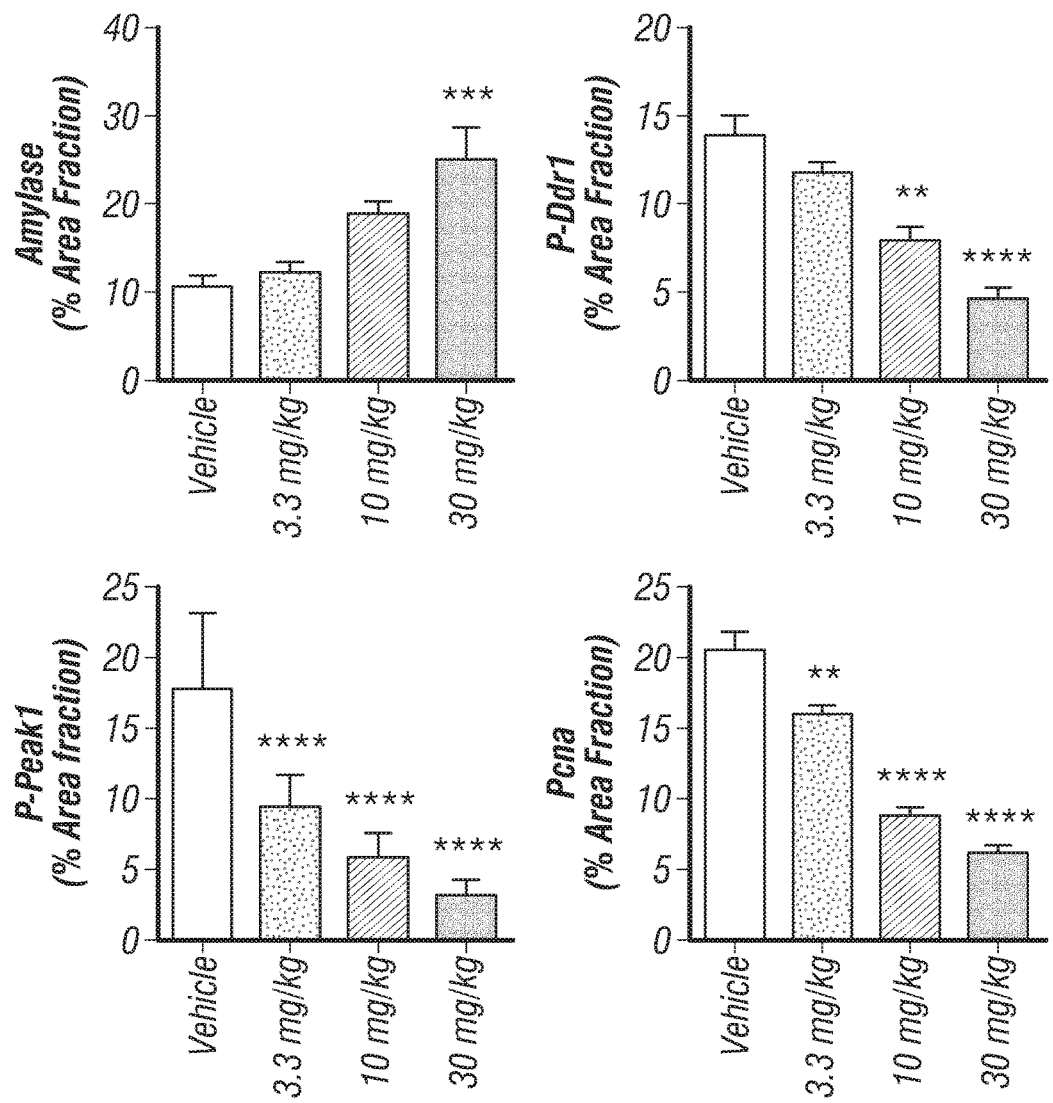
Figure 8G:
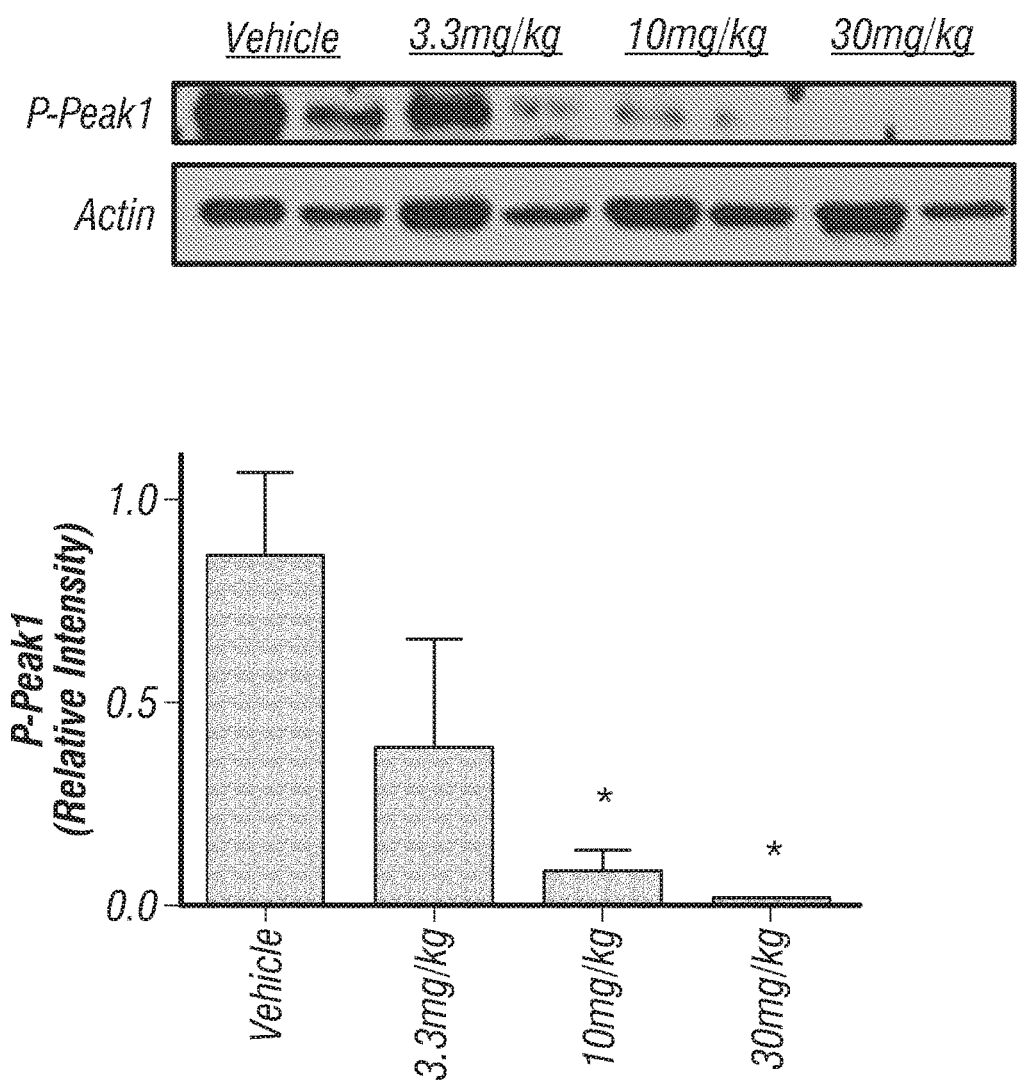
Figure 9A:
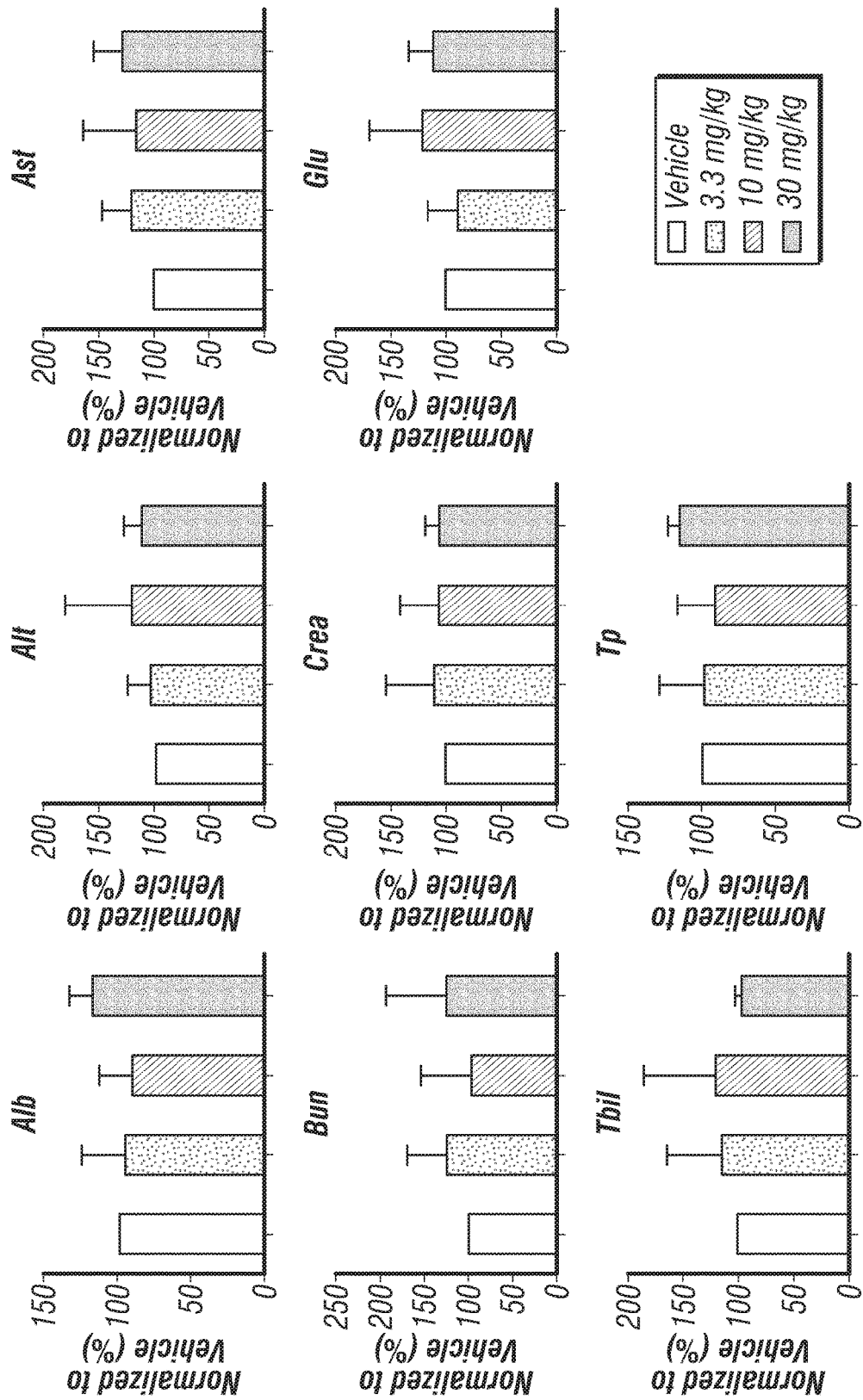
FIGS. 9A-B: Inhibition of Ddr1 with 7rh does not induce observable toxicity.
Figure 9B:
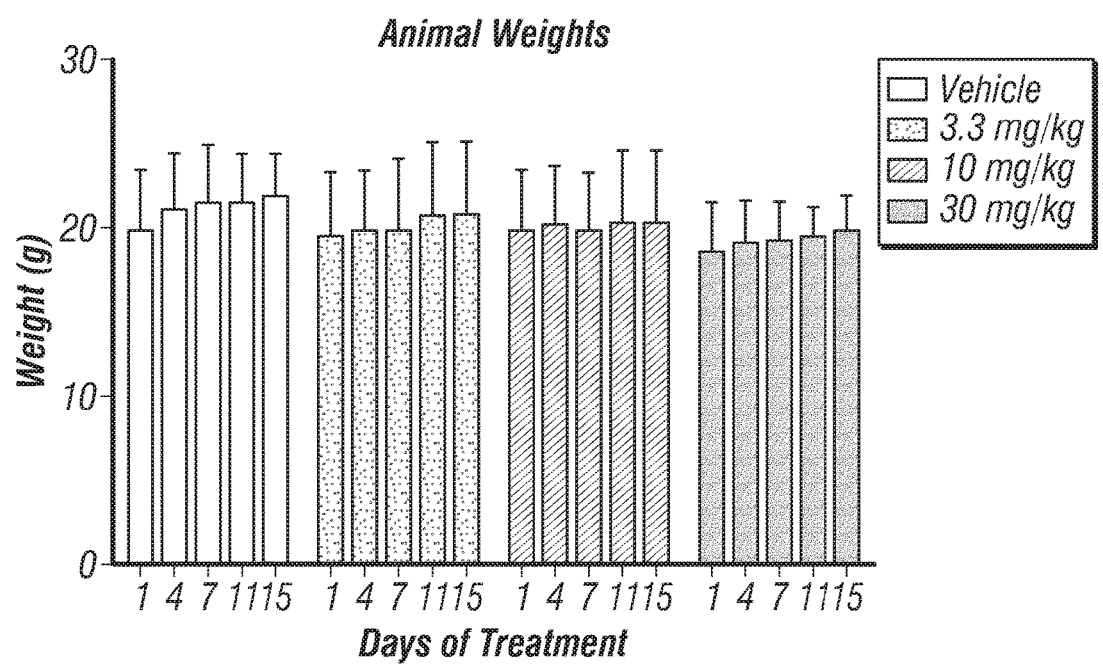
Figure 10A:
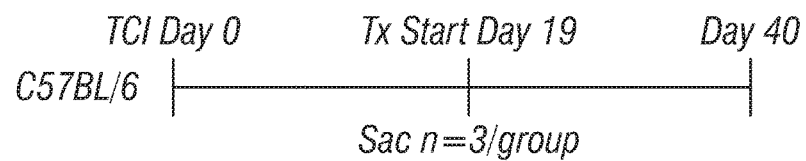
FIGS. 10A-I: 7rh reduced Ddr1-mediated tumorigenicity and signaling.
Figure 10B:
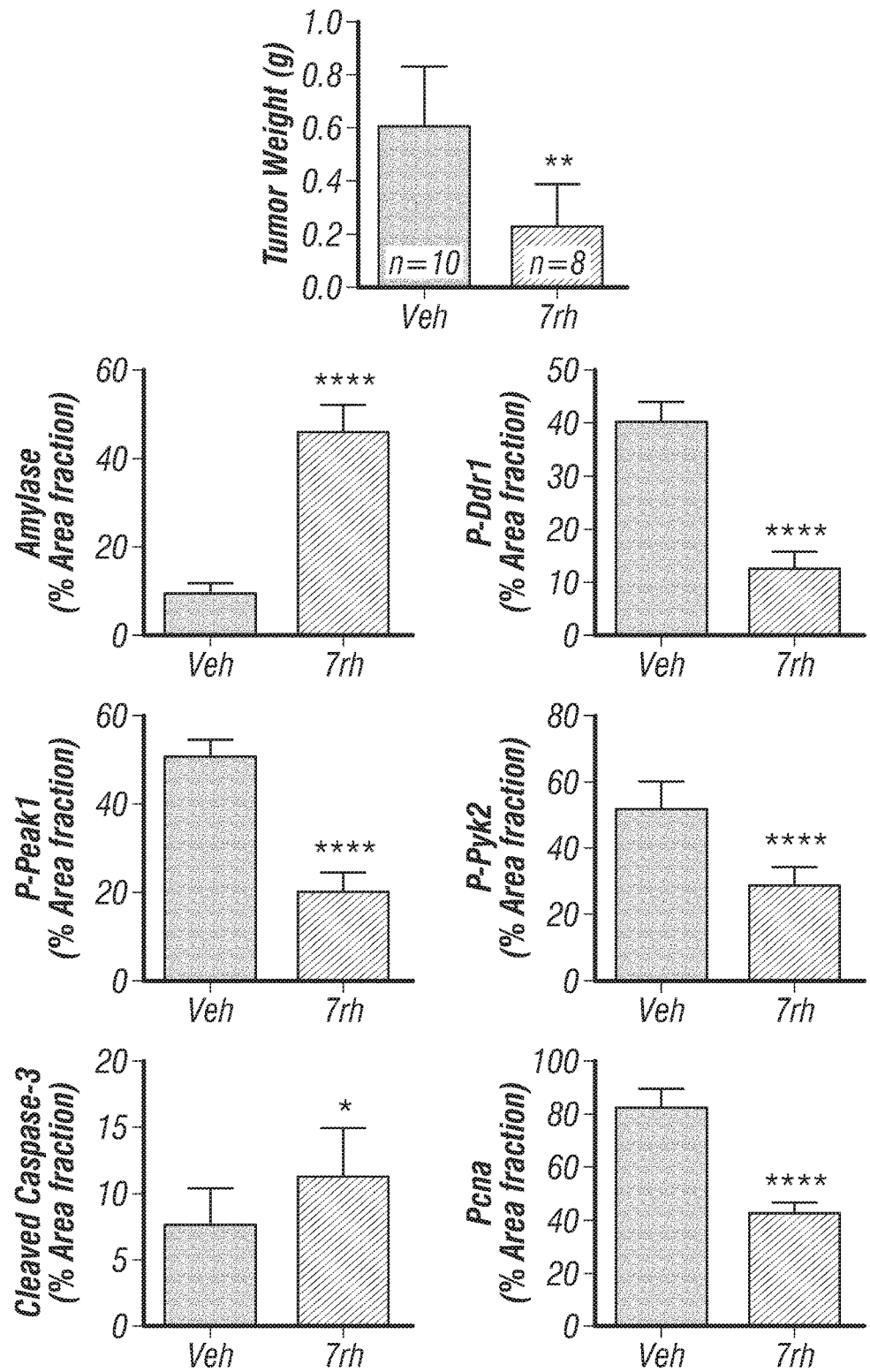
Figure 10C:
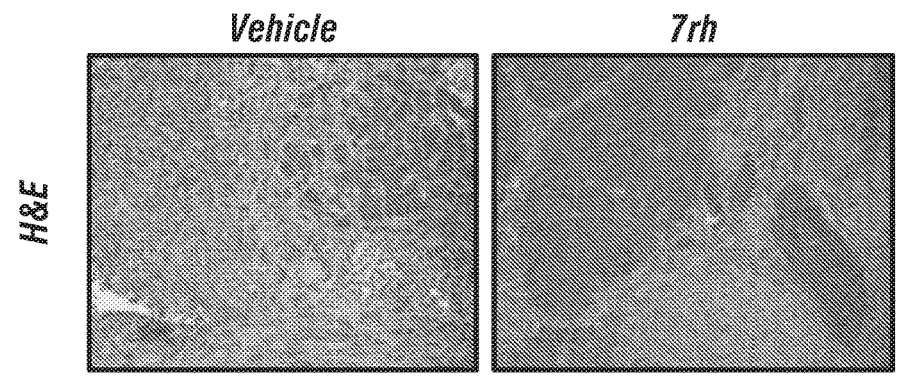
Figure 10D:
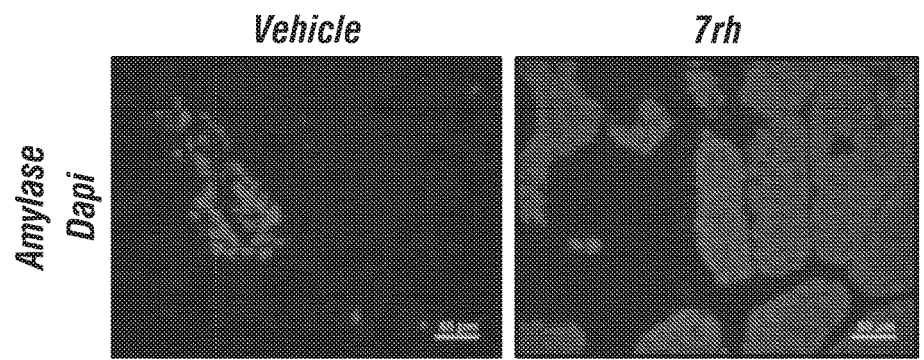
Figure 10E:
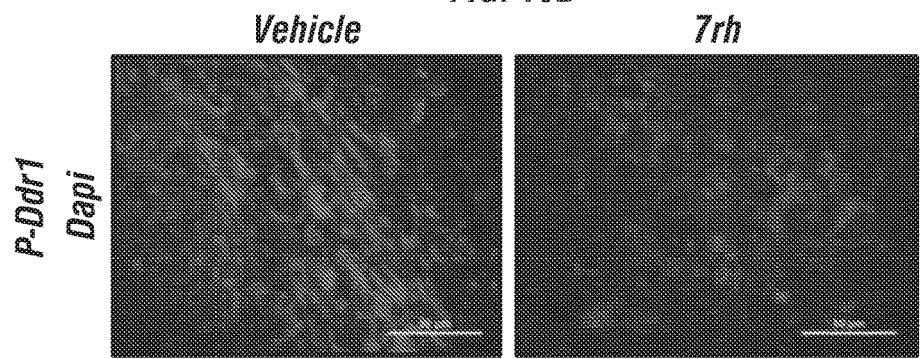
Figure 10F:
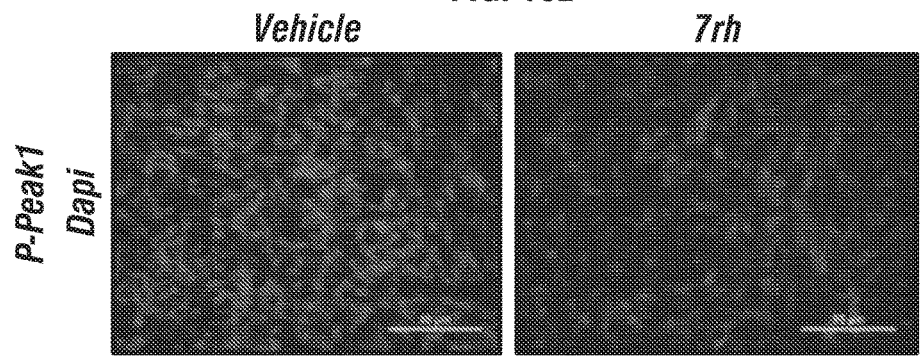
Figure 10G:
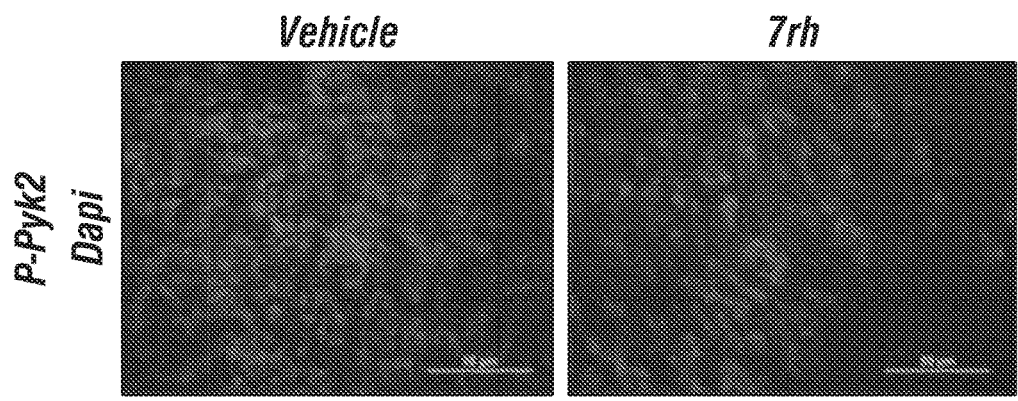
Figure 10H:
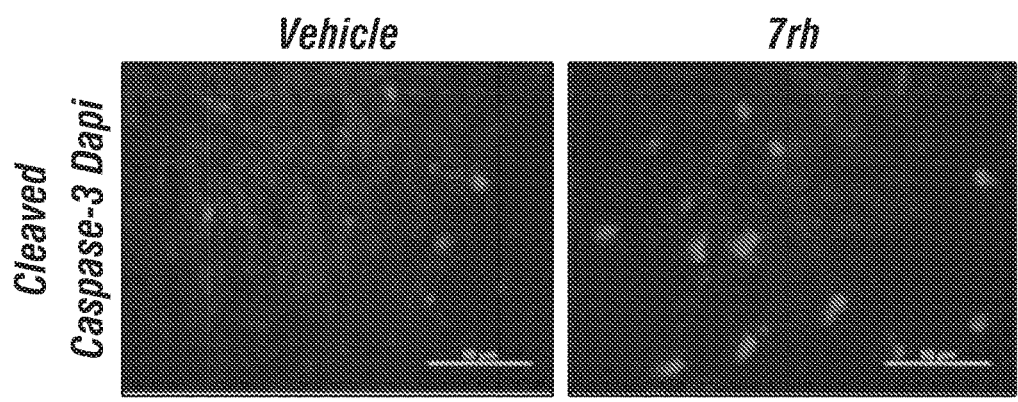
Figure 10I:
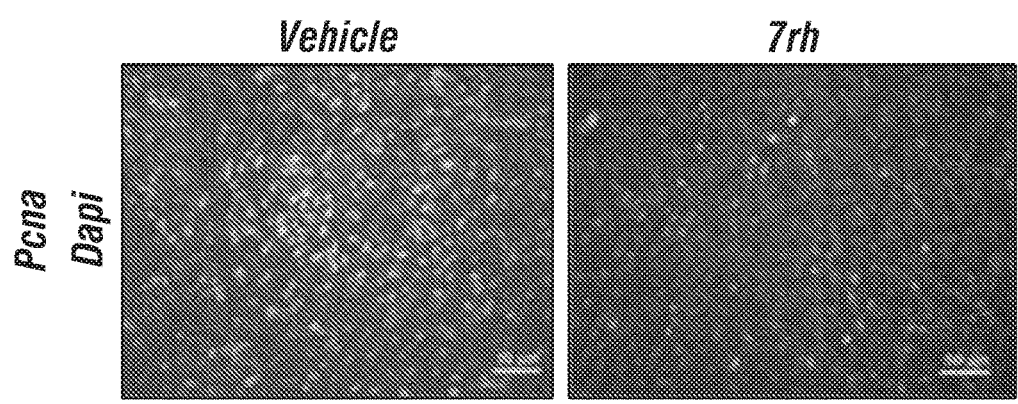

Prior pharmacokinetic studies (Gao et al., 2013) established the in vivo half-life of 7rh to be ~12 hr in rats. To determine an appropriate dose for therapy studies, mice bearing established orthotopic Pan02 pancreatic tumors were given a single dose of 0.1, 1, or 10 mg/kg of 7rh via oral gavage FIG. 7, Table 1). Tumor tissue was collected 12 hours post treatment and analyzed for DDR1 activity. 7rh at 1 mg/kg and 10 mg/kg significantly reduced the phosphorylation of Ddr1 as well as downstream effectors Pyk2 and Peak1, and resulted in an increased apoptotic index (Cleaved Caspase-3) (FIG. 7b-7e) as shown by immunohistochemical analysis. After demonstration that 7rh can reduce DDR1 activity in the tumor microenvironment, a single agent therapy experiment was performed using a titration of 7rh for 2 weeks. Mice bearing established orthotopic Pan02 tumors were treated with 7rh (3, 10, or 30 mg/kg, 3×/week) via oral gavage (FIG. 8, Table 1). 7rh at 10 mg/kg and 30 mg/kg resulted in an increase in normal pancreatic tissue as determined by H&E histology and expression of amylase, a marker of normal acinar tissue (FIG. 8B-8C). 7rh at these concentrations also significantly reduced the level of phosphorylated Ddr1 and Peak1 (FIG. 8D-8E), as well as proliferation noted by the reduction of Pcna levels (FIG. 8F). These findings were corroborated by western blot analysis of tumor lysates that showed a 7rh-dependent reduction of Peak1 phosphorylation (FIG. 8G). 7rh showed no apparent normal tissue toxicity as demonstrated by the maintenance of body weight and the lack of changes in serum metabolites specific for liver and kidney function. Metabolites analyzed included Alb (albumin), Alt (liver transaminases), Ast (aspartate transaminase), Bun (blood urea nitrogen), Crea (creatine), Glu (glucose), Tbil (total bilirubin), and Tp (plasma total protein) (FIG. 9A-9B). Next, the inventors performed a single agent therapy experiment with a fixed concentration of 7rh. Mice bearing established orthotopic Pan02 tumors were treated with 7rh (25 mg/kg, 3×/week) (FIG. 10, Table 1). Therapy was initiated 19 days post tumor cell injection and continued until experiment day 40, at which point animals were sacrificed (FIG. 10A). 7rh significantly reduced primary tumor weight (FIG. 10B). Histological analysis of pancreata from these animals showed that 7rh slowed progression of disease (FIG. 11C). This is consistent with increased amylase expression (FIG. 10D) and a significant decrease in Ddr1, Peak1, and Pyk2 activation (FIG. 10E-10G) in animals receiving 7rh. This was concordant with enhanced apoptosis (Cleaved Caspase-3, FIG. 10H) and reduced proliferation (Pcna, FIG. 10I) in the presence of 7rh therapy.

Figures 11D, 11E, 11F:
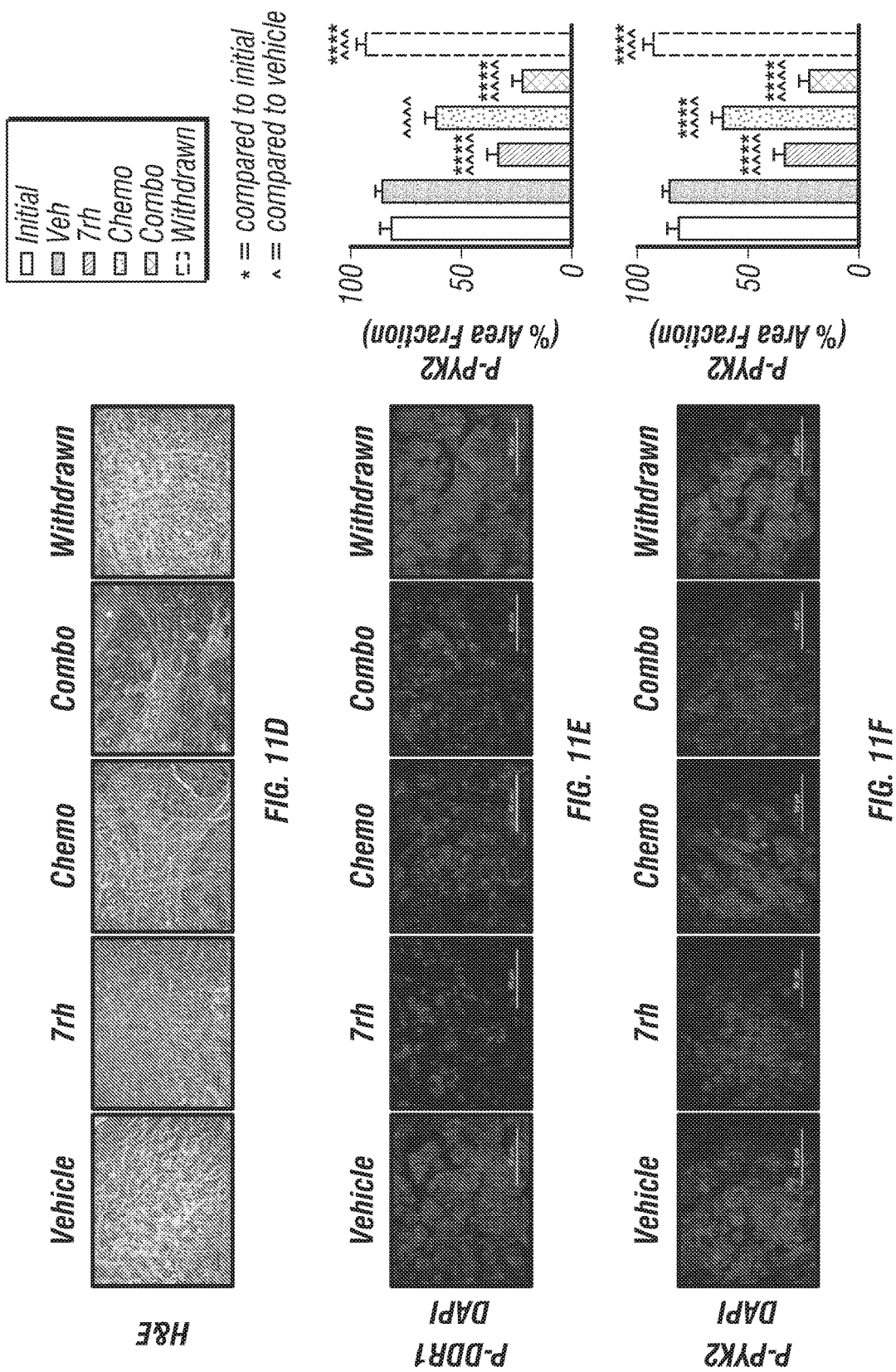
FIGS. 11A-G, I-L: 7rh in combination with chemotherapy improves survival of mice bearing human PDA xenografts.
Figure 11G:
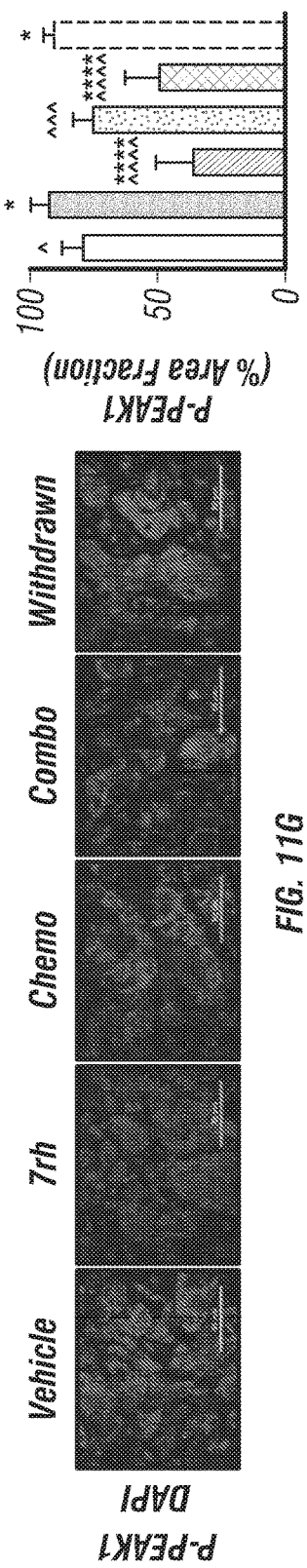
Figure 11I:
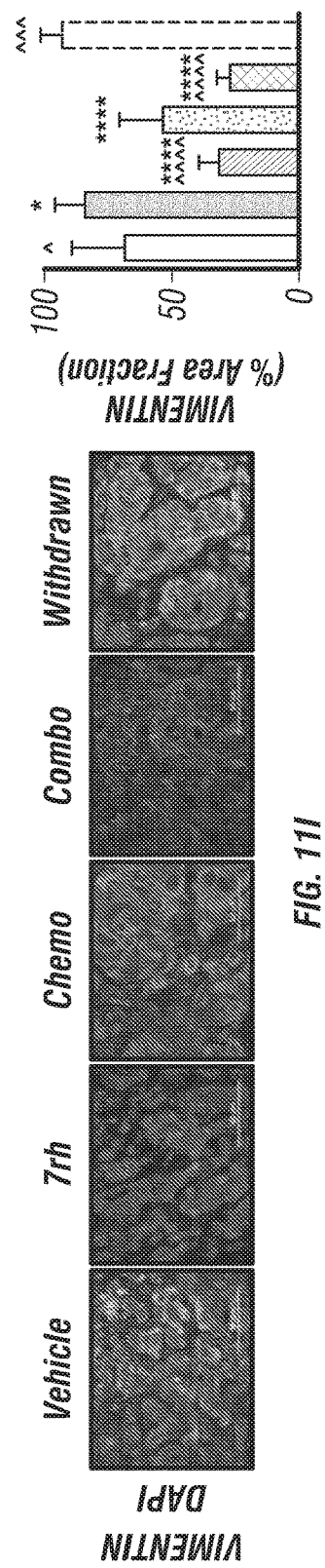
Figure 11J:
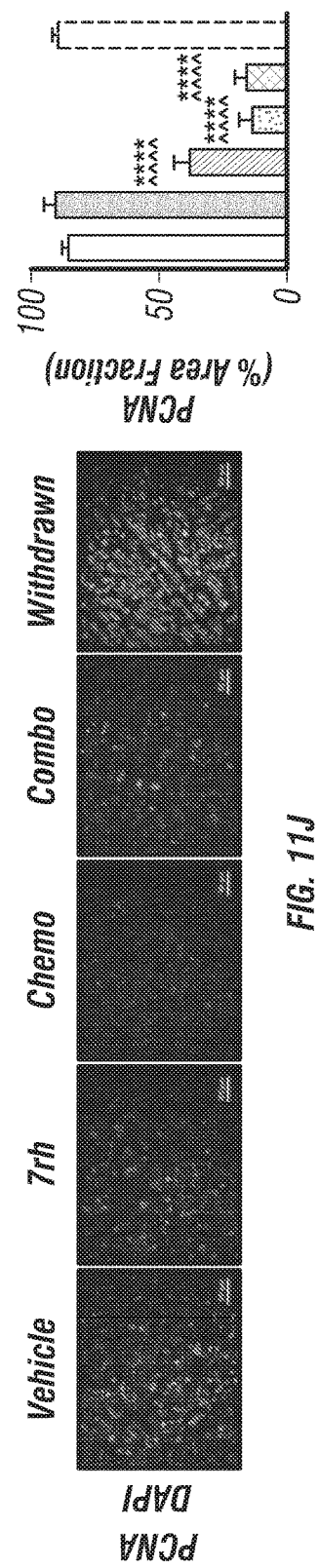
Figure 11K:
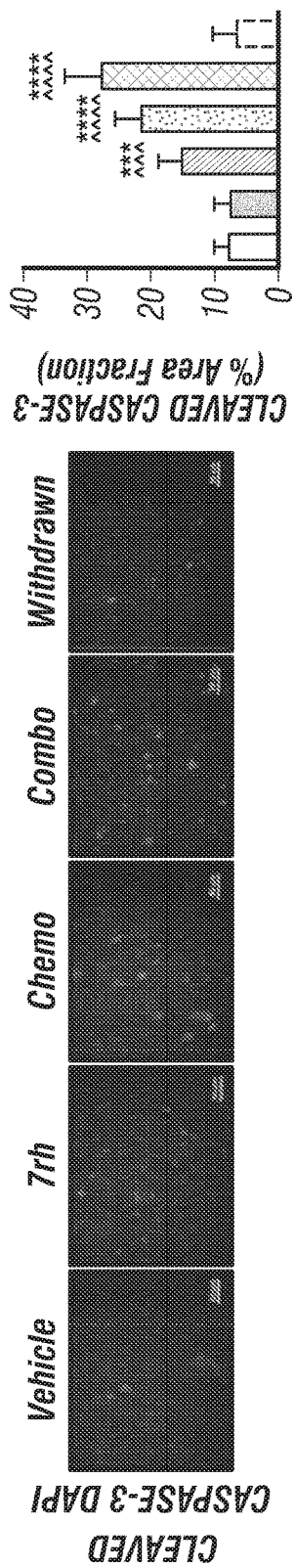
Figure 11L:
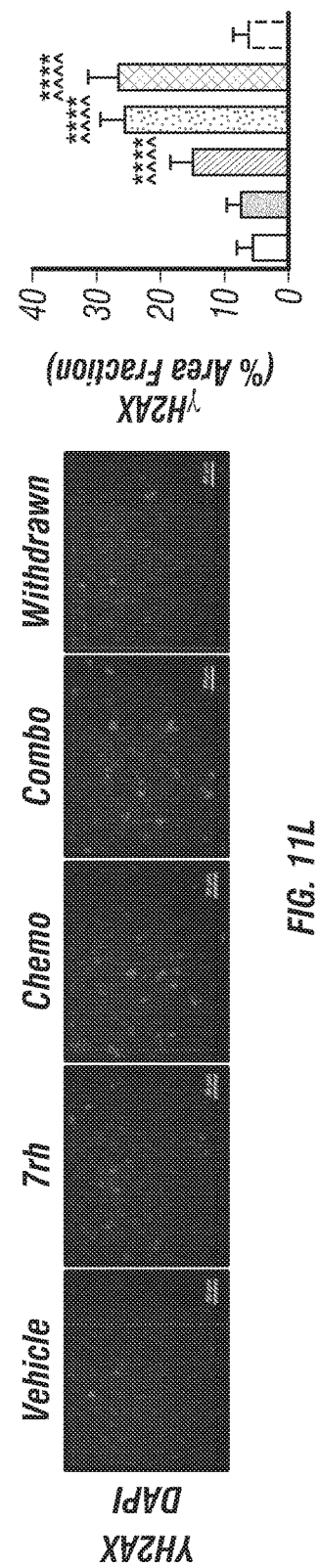

To assess if 7rh enhanced the efficacy of chemotherapy in vivo, the inventors combined 7rh with the standard of care chemotherapy of PDA (gemcitabine and nab-paclitaxel) in a xenograft model of PDA (FIG. 11A, Table 1) Immunocompromised animals bearing orthotopic AsPC-1 tumors were treated with vehicle, 7rh monotherapy (25 mg/kg, 3×/week), the standard of care regimen (chemo: gemcitabine, 15 mg/kg, 2×/week; nab-paclitaxel, 5 mg/kg, 2×/week), or the combination (combo) of 7rh and chemotherapy (FIG. 11A, Table 1). Therapy was initiated 27 days post tumor cell injection and 3 animals from each cohort were sacrificed on day 28 (one day post therapy induction) to document tumor burden at the start of therapy (initial group). Each regimen was continued until individual animals became moribund, at which point the moribund animals were sacrificed. The combination of 7rh+chemotherapy significantly enhanced the median overall survival to 98 days, compared to chemotherapy, 7rh, or vehicle at 73, 57, and 54.5 days respectively. After the median survival was achieved for the combination group, therapy was withdrawn at day 102 to assess the consequence of therapy removal (withdrawn group) (FIG. 11B-11C, FIG. 12). Tumor tissue from each group was analyzed by histology and immunohistochemistry. Combination therapy resulted in more normal pancreatic tissue (H&E), a significant reduction in collagen signaling (P-DDR1, P-PYK2, P-PEAK1), a reduction in VIMENTIN expression as well as cell proliferation (PCNA), and enhanced apoptosis (cleaved CASPASE-3) and DNA damage ($\gamma$H2AX) (FIG. 11D-G, I-L). Withdrawal of therapy from the combination group resulted in restoration of cell proliferation, VIMENTIN expression and collagen signaling to levels similar to that observed in vehicle treated animals. Additionally, the inventors noted that 7rh alone or in combination with chemotherapy reduced trichrome staining suggesting a reduction in fibrosis (FIG. 13A). Tumor weight vs survival days was plotted (FIG. 12B) and indicated that therapy with 7rh, chemotherapy, or the combination reduced primary tumor growth compared to treatment with vehicle. Animal weight was monitored throughout the experiment and no therapy-induced changes in body weight were noted (FIG. 12C).

To determine if the therapeutic efficacy of 7rh combinatorial therapy extended to more rigorous in vivo models, the inventors moved to a genetically engineered mouse model (GEMM) of PDA. KPC (LSL-Kras$^{G12D/+}$; LSL-Trp53$^{R172H/+}$; p48$^{Cre/+}$) mice were enrolled into therapy cohorts at 4 months of age (FIG. 13, Table 1), a time point the inventors have found where greater than 90% of animals have established PDA. Treatment arms were the same as the AsPC-1 xenograft experiment and contained 12 animals/cohort. An additional 9 animals were sacrificed at the start of therapy to document mean tumor burden at the initiation of the experiment. Treatment with the combination regimen enhanced median of survival to 208 days compared to treatment with chemotherapy, 7rh, or vehicle at 180, 159, and 144 days respectively (FIGS. 13B & 13C) Immunohistochemical analyses of tumor tissue harvested at the time of sacrifice demonstrated that inhibition of Ddr1 with 7rh suppressed collagen signaling (P-Ddr1 and P-Peak1), reduced Vimentin expression and cell proliferation (Pcna) while increasing apoptosis (cleaved Caspase-3) and DNA damage ($\gamma$H2ax) (FIGS. 13D-13J). Chemotherapy with gemcitabine and nab-paclitaxel also reduced collagen signaling and Vimentin expression as well as decreasing the number of Pcna positive cells. Additionally, treatment with 7rh alone, chemotherapy alone or the combination induced a reduction in trichrome staining (FIG. 14A). Tumor weight vs survival days was plotted (FIG. 14B) and indicated that therapy with 7rh, conventional chemotherapy, or the combination reduced primary tumor growth compared to treatment with vehicle. Animal weight was not adversely affected by therapy (FIG. 14C). These data demonstrate that Ddr1 inhibition can increase the efficacy of standard of care chemotherapy in robust preclinical models of PDA.

Example 44—Discussion

Based upon the data provided herein, the contribution of collagen-mediated DDR1 signaling to PDA progression was evaluated. The inventors demonstrated that DDR1 and downstream effectors are expressed and activated in human and mouse PDA. Additionally, a novel small molecule inhibitor, 7rh benzamide (Gao et al., 2013), was evaluated effectively abrogated DDR1 signaling thereby reducing liquid colony tumor cell formation, tumor cell migration, and sensitized human PDA cell lines to gemcitabine in vitro. Further, 7rh was found to inhibit its target and has significant therapeutic efficacy in vivo at doses that are free from observable tissue toxicity. Finally, 7rh significantly improved the efficacy of standard of care chemotherapy in robust mouse models of PDA. Overall these data highlight that collagen signaling through DDR1 is a critical and pharmacologically targetable pathway in PDA.

Physiological chemoresistance can result from the accumulation of ECM proteins in the tumor microenvironment, a common characteristic of PDA. Dysregulation of ECM-driven signaling can contribute to the hostile programs of cancer cells (Valiathan et al., 2012). This fibrotic network contributes to the development of a complex tumor microenvironment that promotes PDA development, invasion, metastasis and resistance to chemotherapy (Li et al., 2012). However, the ECM-mediated signaling pathways that drive these programs are unclear.

The matricellular protein Sparc (secreted protein acidic and rich in cysteine) was found previously to reduce collagen I signaling through Ddr1 and that loss of Sparc accelerated PDA progression with a concordant increase in Ddr1 signaling (Aguilera et al., 2014). Furthermore, prior reports on the expression of SPARC in pancreatic tumor cells demonstrated that there is a reduction in SPARC expression by promoter hypermethylation in a high frequency of pancreatic tumor cells and other epithelial cancer cells (Sato et al., 2003 and Cheetham et al., 2008). Additionally, it was reported that restoration of SPARC expression enhanced radiosensitivity and chemosensitivity in pre-clinical models of colon cancer (Tai et al., 2005) and that SPARC expression enhanced chemoresponse in cancer patients (Von Hoff et al., 2011 and Lindner et al., 2015). Thus there was compelling evidence that loss of tumor cell expression of SPARC correlated with tumor progression and poor chemoresponse. Without wishing to be bound by any theory, it is believed that these observations can be explained by the fact that SPARC inhibits collagen-induced DDR1 activation. This is consistent with reports that collagen signaling is associated with chemoresistance in PDA cell lines (Mahadevan and Von Hoff, 2007 and Erkan et al., 2008) and that DDR1 confers resistance to chemotherapy and mediates pro-survival signals (Cader et al., 2013; Ongusaha et al., 2003 and Das et al., 2006).

These studies relied on syngeneic, xenograft and genetic models of PDA. Pan02 (also known as Panc02) cells were utilized because this cell line grows in C57Bl/6 immunocompetent animals, a useful system to evaluate initial toxicity and efficacy of DDR1 inhibition with 7rh. AsPC-1 cells, a commonly used human PDA cell line, were employed because these cells express high levels of endogenous DDR1 activation in vitro and grow robustly in vivo. The KPC model of PDA was also used, which incorporates two common genetic lesions present in human PDA (e.g., KRAS activation and p53 loss). Without wishing to be bound by any theory, it is believed that this model is well-suited for endpoint and survival studies as mice develop advanced PDA with 100% penetrance at approximately 3-4 months of age and tumor progression recapitulates many of the characteristics of human PDA (Hingorani et al., 2005).

DDR1 is up-regulated in fibrotic diseases and contributes to the initiation and progression of fibrosis (Kerroch et al., 2012). Reduced collagen deposition in tumors from mice treated with 7rh were observed, thus inhibition of DDR1 might improve response to chemotherapy in a cell autonomous manner and also improve drug delivery without disrupting the function of cancer associated fibroblasts. DDR1 inhibition has also been shown to reduce tumorigenicity in multiple tumor models (Shintani et al., 2008; Kim et al., 2011; Valencia et al., 2012 and Li et al., 2015). Silencing DDR1 by siRNA has been shown to reduce metastatic activity in lung cancer models (Miao et al., 2013 and Valencia et al., 2012) and enhance chemosensitivity to genotoxic drugs in breast cancer cells (Das et al., 2006). Additionally, DDR1 expression and activity is reported to correlate with worse outcome in a cohort of gastric cancer patients. This study shows 7rh-mediated inhibition of DDR1 in gastric cancer cells reduced tumorigenic characteristics in vitro and tumor growth in vivo.

Several small molecule inhibitors (imatinib, nilotinib and dasatinib) that target Breakpoint Cluster Region-Abelson kinase (BCR-ABL) also potently inhibit DDR1/DDR2 activity (Day et al., 2008 and Rix et al., 2007). Thus, the potential activity of imatinib and vinorelbine in a phase I/II trial in metastatic breast cancer patients (Maass et al., 2014), as well as dasatinib in numerous clinical trials in solid tumors (Roskoski, 2015), could be due in part to the inhibition of DDRs. Dasatinib in particular has demonstrated promising therapeutic efficacy in lung cancer cells (Ding et al., 2008) and squamous cell carcinoma (SCC) patients (Pitini et al., 2013) harboring gain-of-function DDR2 mutations.

The data suggest that inhibition of collagen-mediated DDR1 activity can improve the efficacy of standard chemotherapy of pancreatic cancer.

Example 45—Kinase Inhibition of Other Compounds

TABLE 3

$IC_{50}$ (nM) values of part of compounds on various kinases inhibition

| Example number | Compound number | $IC_{50}$ (nM unless otherwise noted) | | | |
|---|---|---|---|---|---|
| | | DDR1 | DDR2 | Bcr-Abl | c-Kit |
| 1 | D2095 | 38.3 | 1.8 μM | 2.1 μM | >10 μM |
| 2 | D2217 | 444.5 | 5.8 μM | 1.4 μM | >10 μM |
| 3 | D2210 | 441.5 | 8.0 μM | 664.1 | >10 μM |
| 4 | D2211 | 328.0 | 4.3 μM | >10 μM | >10 μM |
| 5 | D2568 | 571.5 | 3.6 μM | 4.5 μM | 8.7 μM |
| 6 | D2103 | 70.9 | 1.2 μM | 6.1 μM | >10 μM |
| 7 | D2102 | 223 | 4.5 μM | >10 μM | >10 μM |
| 8 | D2198 | 65.9 | 914.7 | >10 μM | >10 μM |
| 9 | D2274 | 159 | 1.1 μM | >10 μM | >10 μM |
| 10 | D2276 | 36.7 | 449 | >10 μM | >10 μM |
| 11 | D2188 | 132.4 | 2.2 μM | >10 μM | >10 μM |
| 12 | D2190 | 19.9 | 334 | 546.5 | >10 μM |
| 13 | D2199 | 191 | 10 μM | >10 μM | >10 μM |
| 14 | D2197 | 25.6 | 604 | >10 μM | >10 μM |
| 15 | D2193 | 50.5 | 1.4 μM | >10 μM | >10 μM |
| 16 | D2187 | 35.7 | 647.0 | 7.2 μM | >10 μM |
| 17 | D2275 | 39.1 | 527 | >10 μM | >10 μM |
| 18 | D2201 | 193.4 | 4.5 μM | >10 μM | >10 μM |
| 19 | D2194 | 166.5 | 2.2 μM | >10 μM | >10 μM |
| 20 | D2573 | 222.0 | 2.3 μM | >10 μM | >10 μM |
| 21 | D2192 | 254 | 6.7 μM | >10 μM | >10 μM |
| 22 | D2215 | 71.6 | 457.0 | >10 μM | >10 μM |
| 23 | D2474 | 31.4 | 1.2 μM | 10 μM | >10 μM |
| 24 | D2473 | 18 | 671.8 | 6.7 μM | >10 μM |
| 25 | D2475 | 29.6 | 861.6 | 10 μM | >10 μM |
| 26 | D2202 | 19.4 | 432 | 7.2 μM | >10 μM |
| 27 | D2214 | 48.8 | 1.4 μM | >10 μM | >10 μM |
| 28 | D2350 | 66.6 | 939.5 | 4.3 μM | >10 μM |
| 29 | D2476 | 44.6 | 1.4 μM | 10 μM | >10 μM |
| 30 | D2574 | 544.5 | 7.6 μM | >10 μM | >10 μM |
| 31 | D2347 | 89.0 | 1.1 μM | 10 μM | >10 μM |
| 32 | D2196 | 20.6 | 306.5 | 4.8 μM | >10 μM |
| 33 | D2195 | 79.9 | 945 | >10 μM | >10 μM |
| 34 | D2213 | 85.3 | 2.0 μM | >10 μM | >10 μM |
| 35 | D2191 | 209.4 | 3.7 μM | >10 μM | >10 μM |
| 36 | D2212 | 353.8 | 7.8 μM | >10 μM | >10 μM |
| 37 | D2099 | 294.3 | 4.2 μM | >10 μM | >10 μM |
| 38 | D2200 | 42.6 | 514.5 | >10 μM | >10 μM |
| 39 | D2100 | 630.5 | >10 μM | >10 μM | >10 μM |
| 40 | D2164 | 66.2 | 1.4 μM | >10 μM | >10 μM |

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the disclosure. All variations and modifications apparent to those skilled in the art are deemed to be within the spirit, scope, and concept of the disclosure as defined by the appended claims.

REFERENCES

The following references to the extent that they provide exemplary procedural or other details supplementary to those set forth herein, are specifically incorporated herein by reference.

Aguilera et al., Cancer Res, 74(4): p. 1032-44, 2014.
Apte et al., Pancreas, 29(3): p. 179-87, 2004.
Cader et al., Blood, 122(26): p. 4237-45, 2013.
Cerami et al., Cancer Discov, 2(5): p. 401-4, 2012.
Chauhan et al., Nat Commun, 4: p. 2516, 2013.
Chou, Pharmacol Rev, 58(3): p. 621-81, 2006.
Das et al., Cancer Res, 66(16): p. 8123-30, 2006.
Day et al., Eur J Pharmacol, 599(1-3): p. 44-53, 2008.
Dineen et al., Cancer Res, 70(7): p. 2852-61, 2010.
Ding et al., Nature, 455(7216): p. 1069-75, 2008.
Erkan et al., Clin Gastroenterol Hepatol, 6(10): p. 1155-61, 2008.
Furuyama et al., Nat Genet, 43(1): p. 34-41, 2011.
Gao et al., J Med Chem, 56(8): p. 3281-95, 2013.
Gao et al., Sci Signal, 6(269): p. pl1, 2013.
Gyorffy et al., PLoS One, 8(12): p. e82241, 2013.
Hingorani et al., Cancer Cell, 7(5): p. 469-83, 2005.
Kerroch et al., FASEB J, 26(10): p. 4079-91, 2012.
Kim et al., J Biol Chem, 286(20): p. 17672-81, 2011.
Leitinger, Int Rev Cell Mol Biol, 310: p. 39-87, 2014.
Li et al., J Med Chem, 2015.
Lindner et al., Ann Oncol, 26(1): p. 95-100, 2015.
Maass et al., Oncology, 87(5): p. 300-10, 2014.
Mahadevan and Von Hoff, Mol Cancer Ther, 6(4): p. 1186-97, 2007.
Miao et al., Med Oncol, 30(3): p. 626, 2013.
Ongusaha et al., EMBO J, 22(6): p. 1289-301, 2003.
Pitini et al., Lung Cancer, 82(1): p. 171-2, 2013.
Rix et al., Blood, 110(12): p. 4055-63, 2007.
Roskoski, Pharmacol Res, 94: p. 9-25, 2015.
Seymour et al., Dev Biol, 323(1): p. 19-30, 2008.
Shintani et al., J Cell Biol, 180(6): p. 1277-89, 2008.
Tai et al., J Clin Invest, 115(6): p. 1492-502, 2005.
Valencia et al., Clin Cancer Res, 18(4): p. 969-80, 2012.
Valiathan et al., Cancer Metastasis Rev, 31(1-2): p. 295-321, 2012.
Von Hoff et al., J Clin Oncol, 29(34): p. 4548-54, 2011.

What is claimed is:

1. A compound of the formula:

(I)

[structure: tetrahydroisoquinoline core with substituents $R_1$ on N, $R_2$, $R_3$, $R_3'$, $(R_6)_n$ on fused benzene ring, linked through group $A$ to phenyl bearing $R_4$, $R_5$, and $(R_7)_m$]

wherein:

A is $-NR_8C(O)-$ or $-C(O)NR_8-$; wherein:

$R_8$ is hydrogen, alkyl$_{(C \leq 6)}$, or substituted alkyl$_{(C \leq 6)}$;

$R_1$ is aryl$_{(C \leq 12)}$, heteroaryl$_{(C \leq 12)}$, or a substituted version of either of these groups;

$R_2$, $R_3$, and $R_3'$ are each independently hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$;

$R_4$ is hydrogen, alkyl$_{(C \leq 12)}$, cycloalkyl$_{(C \leq 12)}$, aryl$_{(C \leq 12)}$, substituted alkyl$_{(C \leq 12)}$, substituted cycloalkyl$_{(C \leq 12)}$, or substituted aryl$_{(C \leq 12)}$;

$R_5$ is $-X-R_9$, wherein:

X is a covalent bond, alkanediyl$_{(C \leq 8)}$, or substituted alkanediyl$_{(C \leq 8)}$;

$R_9$ is amino or heterocycloalkyl$_{(C \leq 12)}$, heteroaryl$_{(C \leq 12)}$, alkylamino$_{(C \leq 12)}$, dialkylamino$_{(C \leq 12)}$, or a substituted version of any of these groups; or a group of the formula:

wherein:
R$_{10}$ is hydrogen, alkyl$_{(C≤12)}$, cycloalkyl$_{(C≤12)}$, substituted alkyl$_{(C≤12)}$, or substituted cycloalkyl$_{(C≤12)}$; and
p and q are each 0, 1, or 2;
R$_6$ and R$_7$ are each independently amino, cyano, halo, hydroxy, hydroxysulfonyl, nitro, sulfonamide; or substituted or unsubstituted alkyl$_{(C≤8)}$, acyl$_{(C≤8)}$, alkoxy$_{(C≤8)}$, amido$_{(C≤8)}$, acyloxy$_{(C≤8)}$, alkylamino$_{(C≤8)}$, or dialkylamino$_{(C≤8)}$; and
m and n are each independently 0, 1, 2, or 3;
or a pharmaceutically acceptable salt thereof.

2. The compound of claim 1, wherein the compound is further defined as:

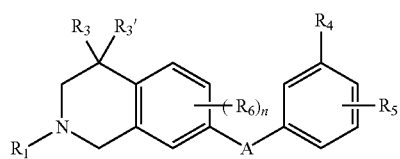

(II)

wherein: A, R$_1$, R$_3$, R$_3'$, R$_4$, R$_5$, R$_6$, and n are as defined above;
or a pharmaceutically acceptable salt thereof.

3. The compound of claim 1, wherein the compound is further defined as:

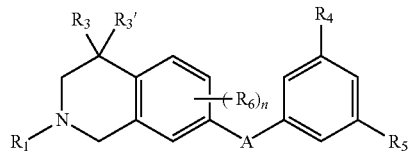

(III)

wherein: A, R$_1$, R$_3$, R$_3'$, R$_4$, R$_5$, R$_6$, and n are as defined above;
or a pharmaceutically acceptable salt thereof.

4. The compound according to claim 1, wherein R$_1$ is heteroaryl$_{(C≤12)}$.

5. The compound according to claim 1, wherein R$_3$ is alkyl$_{(C≤12)}$.

6. The compound according to claim 1, wherein R$_3$ is hydrogen.

7. The compound according to claim 1, wherein R$_3'$ is hydrogen.

8. The compound according to claim 1, wherein R$_4$ is alkyl$_{(C≤12)}$ or substituted alkyl$_{(C≤12)}$.

9. The compound according to claim 1, wherein R$_4$ is cycloalkyl$_{(C≤12)}$ or substituted cycloalkyl$_{(C≤12)}$.

10. The compound according to claim 1, wherein R$_4$ is aryl$_{(C≤12)}$.

11. The compound according to claim 1, wherein m is 0.

12. The compound according to claim 1, wherein m is 1.

13. The compound according to claim 1, wherein R$_7$ is alkyl$_{(C≤8)}$ or substituted alkyl$_{(C≤8)}$.

14. The compound according to claim 1, wherein R$_7$ is halo.

15. A compound of the formula:
4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide;
N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(3-((4-methylpiperazin-1-yl)methyl)-5-(trifluoromethyl)phenyl)-2-(pyridin-3-yl)-1,2,3,4-tetrahydroisoquinoline-7-carboxamide;
N-(3-((4-methylpiperazin-1-yl)methyl)-5-(trifluoromethyl)phenyl)-2-(quinolin-3-yl)-1,2,3,4-tetrahydroisoquinoline-7-carboxamide;
4-methyl-N-(3-((4-methylpiperazin-1-yl)methyl)-5-(trifluoromethyl)phenyl)-2-(pyridin-3-yl)-1,2,3,4-tetrahydroisoquinoline-7-carboxamide;
4,4-dimethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;
N-(4-chloro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide;
4-methyl-N-(4-methyl-3-((4-methylpiperazin-1-yl)methyl)-5-(trifluoromethyl)phenyl)-2-(pyrimidin-5-yl)-1,2,3,4-tetrahydroisoquinoline-7-carboxamide;
4-methyl-N-(3-(2-(4-methylpiperazin-1-yl)ethyl)-5-(trifluoromethyl)phenyl)-2-(pyrimidin-5-yl)-1,2,3,4-tetrahydroisoquinoline-7-carboxamide;
4-methyl-N-(3-(4-methylpiperazin-1-yl)-5-(trifluoromethyl)phenyl)-2-(pyrimidin-5-yl)-1,2,3,4-tetrahydroisoquinoline-7-carboxamide;
4-methyl-N-(4-((4-methylpiperazin-1-yl)methyl)-3-(trifluoromethyl)phenyl)-2-(pyrimidin-5-yl)-1,2,3,4-tetrahydroisoquinoline-7-carboxamide;
4-methyl-2-(pyrimidin-5-yl)-N-(3-(trifluoromethyl)phenyl)-1,2,3,4-tetrahydroisoquinoline-7-carboxamide;
4-methyl-N-(3-((4-methyl-1,4-diazepan-1-yl)methyl)-5-(trifluoromethyl)phenyl)-2-(pyrimidin-5-yl)-1,2,3,4-tetrahydroisoquinoline-7-carboxamide;
N-(3-ethyl-5-((4-methylpiperazin-1-yl)methyl)phenyl)-4-methyl-2-(pyrimidin-5-yl)-1,2,3,4-tetrahydroisoquinoline-7-carboxamide;
N-(3-isopropyl-5-((4-methylpiperazin-1-yl)methyl)phenyl)-4-methyl-2-(pyrimidin-5-yl)-1,2,3,4-tetrahydroisoquinoline-7-carboxamide;
N-(3-((4-ethylpiperazin-1-yl)methyl)-5-(trifluoromethyl)phenyl)-4-methyl-2-(pyrimidin-5-yl)-1,2,3,4-tetrahydroisoquinoline-7-carboxamide;
4-methyl-N-(3-(morpholinomethyl)-5-(trifluoromethyl)phenyl)-2-(pyrimidin-5-yl)-1,2,3,4-tetrahydroisoquinoline-7-carboxamide;
4-methyl-N-(3-(piperidin-1-ylmethyl)-5-(trifluoromethyl)phenyl)-2-(pyrimidin-5-yl)-1,2,3,4-tetrahydroisoquinoline-7-carboxamide;
4-methyl-2-(pyrimidin-5-yl)-N-(3-(pyrrolidin-1-ylmethyl)-5-(trifluoromethyl)phenyl)-1,2,3,4-tetrahydroisoquinoline-7-carboxamide;
N-(3-((dimethylamino)methyl)-5-(trifluoromethyl)phenyl)-4-methyl-2-(pyrimidin-5-yl)-1,2,3,4-tetrahydroisoquinoline-7-carboxamide;

N-(3-cyclohexyl-5-((4-methylpiperazin-1-yl)methyl)phenyl)-4-methyl-2-(pyrimidin-5-yl)-1,2,3,4-tetrahydroisoquinoline-7-carboxamide;

N-(3-(((2-(dimethylamino)ethyl)(methyl)amino)methyl)-5-(trifluoromethyl)phenyl)-4-methyl-2-(pyrimidin-5-yl)-1,2,3,4-tetrahydroisoquinoline-7-carboxamide;

N-(3-(((R)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide;

N-(3-(((S)-3-(dimethylamino)pyrrolidin-1-yl)methyl)-5-(trifluoromethyl)phenyl)-4-methyl-2-(pyrimidin-5-yl)-1,2,3,4-tetrahydroisoquinoline-7-carboxamide;

4-methyl-N-(3-(4-methyl-1H-imidazol-1-yl)-5-(trifluoromethyl)phenyl)-2-(pyrimidin-5-yl)-1,2,3,4-tetrahydroisoquinoline-7-carboxamide;

N-(4-fluoro-3-((4-methylpiperazin-1-yl)methyl)-5-(trifluoromethyl)phenyl)-4-methyl-2-(pyrimidin-5-yl)-1,2,3,4-tetrahydroisoquinoline-7-carboxamide;

N-(3-tert-butyl-5-((4-methylpiperazin-1-yl)methyl)phenyl)-4-methyl-2-(pyrimidin-5-yl)-1,2,3,4-tetrahydroisoquinoline-7-carboxamide;

4-methyl-N-(5-((4-methylpiperazin-1-yl)methyl)biphenyl-3-yl)-2-(pyrimidin-5-yl)-1,2,3,4-tetrahydroisoquinoline-7-carboxamide;

3-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

N-(3-cyclopropyl-5-((4-methylpiperazin-1-yl)methyl)phenyl)-4-methyl-2-(pyrimidin-5-yl)-1,2,3,4-tetrahydroisoquinoline-7-carboxamide;

N-(3-cyclopentyl-5-((4-methylpiperazin-1-yl)methyl)phenyl)-4-methyl-2-(pyrimidin-5-yl)-1,2,3,4-tetrahydroisoquinoline-7-carboxamide;

N-(3-((4-cyclohexylpiperazin-1-yl)methyl)-5-(trifluoromethyl)phenyl)-4-methyl-2-(pyrimidin-5-yl)-1,2,3,4-tetrahydroisoquinoline-7-carboxamide;

4-ethyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

4-methyl-2-(pyrimidin-5-yl)-N-(3-(thiomorpholinomethyl)-5-(trifluoromethyl)phenyl)-1,2,3,4-tetrahydroisoquinoline-7-carboxamide;

3-((4-methylpiperazin-1-yl)methyl)-N-(2-(pyrimidin-5-yl)-1,2,3,4-tetrahydroisoquinolin-7-yl)-5-(trifluoromethyl)benzamide;

(S)-4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

(R)-4-methyl-N-(3-((4-methylpiperazin-1-yl)methyl)-5-(trifluoromethyl)phenyl)-2-(pyrimidin-5-yl)-1,2,3,4-tetrahydroisoquinoline-7-carboxamide;

(S)—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide;

(R)—N-(4-methyl-2-(pyrimidin-5-yl)-1,2,3,4-tetrahydroisoquinolin-7-yl)-3-((4-methylpiperazin-1-yl)methyl)-5-(trifluoromethyl)benzamide;

or a pharmaceutically acceptable salt thereof.

16. A pharmaceutical composition comprising:
(a) a compound according to claim 1; and
(b) a pharmaceutically acceptable carrier.

17. A method of treating a disease or disorder in a patient in need thereof comprising administering to the patient a therapeutically effective amount of a compound according to claim 1, wherein said disease or disorder is mediated by DDAR activation.

18. A method of inhibiting discoidin domain receptor (DDR) protein comprising contacting the protein with a compound according to claim 1 in an amount sufficient to inhibit the protein.

19. A method of treating cancer in a patient in need thereof comprising administering to the patient a therapeutically effective amount of:
(a) a compound according to claim 1; and
(b) a second chemotherapeutic compound.

* * * * *